US011365179B2

United States Patent
Hassfeld et al.

(10) Patent No.: US 11,365,179 B2
(45) Date of Patent: Jun. 21, 2022

(54) METHOD FOR THE PREPARATION OF A 2,4,5-TRISUBSTITUTED 1,2,4-TRIAZOLONE

(71) Applicants: BAYER AKTIENGESELLSCHAFT, Leverkusen (DE); BAYER PHARMA AKTIENGESELLSCHAFT, Berlin (DE)

(72) Inventors: Jorma Hassfeld, Düsseldorf (DE); Stefan Nikolaus Gradl, Berlin (DE); Philipp Rubenbauer, Bensheim (DE); Henricus Nicolaas Sebastiaan Van Der Haas, Nijmegen (NL); Reinerus Gerardus Gieling, Beuningen (NL)

(73) Assignees: BAYER AKTIENGESELLSCHAFT, Leverkusen (DE); BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 17/046,143

(22) PCT Filed: Apr. 3, 2019

(86) PCT No.: PCT/EP2019/058389
§ 371 (c)(1),
(2) Date: Oct. 8, 2020

(87) PCT Pub. No.: WO2019/197239
PCT Pub. Date: Oct. 17, 2019

(65) Prior Publication Data
US 2021/0032212 A1    Feb. 4, 2021

(30) Foreign Application Priority Data

Apr. 10, 2018  (EP) ..................... 18166552
Dec. 17, 2018  (EP) ..................... 18212916

(51) Int. Cl.
*C07D 249/12*  (2006.01)
*C07D 405/12*  (2006.01)
*A61P 35/00*  (2006.01)
*A61K 31/4196*  (2006.01)

(52) U.S. Cl.
CPC ......... *C07D 249/12* (2013.01); *C07D 405/12* (2013.01); *C07B 2200/13* (2013.01)

(58) Field of Classification Search
CPC ................ C07D 249/12; C07D 405/12; C07B 2200/13; A61P 35/00; A61K 31/4196
See application file for complete search history.

(56) References Cited

U.S. PATENT DOCUMENTS

| 4,089,958 | A  | 5/1978  | Freed et al.  |
| 6,444,613 | B1 | 9/2002  | Feurer et al. |
| 10,815,215 | B2 | 10/2020 | Gradl et al. |
| 10,968,216 | B2 | 4/2021  | Gradl et al. |
| 11,130,745 | B2 | 9/2021  | Gradl et al. |
| 2016/0251341 | A1 | 9/2016 | Short |
| 2021/0188846 | A1 | 6/2021 | Gradl et al. |

FOREIGN PATENT DOCUMENTS

| CN | 103006645 A | 4/2013 |
| DE | 2156472 A1  | 5/1972 |
| WO | 1998002422 A1 | 1/1998 |
| WO | 1999054315 A2 | 10/1999 |
| WO | 2010077686 A1 | 7/2010 |
| WO | 2011129133 A1 | 10/2011 |
| WO | 2013186692 A1 | 12/2013 |
| WO | 2014089140 A1 | 6/2014 |
| WO | 2018077923 A1 | 5/2018 |

OTHER PUBLICATIONS

Donnez, J., "Uterine fibroid management: from the present to the future." Human reproduction update 22.6 (2016): 665-686.*
Maroun, J., "Multicenter phase II study of brequinar sodium in patients with advanced lung cancer." Cancer chemotherapy and pharmacology 32.1 (1993): 64-66.*
Moore, M., "Multicenter phase II study of brequinar sodium in patients with advanced gastrointestinal cancer." Investigational new drugs 11.1 (1993): 61-65.*
Natale, R., "Multicenter phase II trial of brequinar sodium in patients with advanced melanoma." Annals of oncology 3.8 (1992): 659-660.*
Urba, S., "Multicenter phase II trial of brequinar sodium in patients with advanced squamous-cell carcinoma of the head and neck." Cancer chemotherapy and pharmacology 31.2 (1992): 167-169.*
Sawant, K.D., "Necessity of establishing chemical integrity of polymorphs of drug substance using a combination of NMR, HPLC, elemental analysis, and solid-state characterization techniques: case studies." Organic Process Research & Development 17.3 (2013): 519-532.*
Reis, R.A.G., "The dihydroorotate dehydrogenases: past and present." Archives of biochemistry and biophysics 632 (2017): 175-191.*

(Continued)

*Primary Examiner* — John M Mauro
(74) *Attorney, Agent, or Firm* — Melissa Hunter-Ensor; Scott Goncher; Greenberg Traurig, LLP

(57) ABSTRACT

The present invention provides methods for the preparation of Compound (I): Compound (I), the use of intermediates for the preparation of said compound and its crystalline form A.

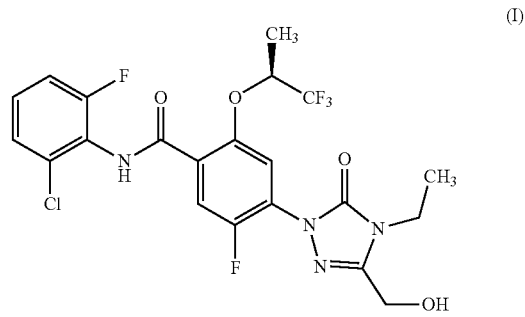

20 Claims, 7 Drawing Sheets

(56) References Cited

OTHER PUBLICATIONS

Figure 1:
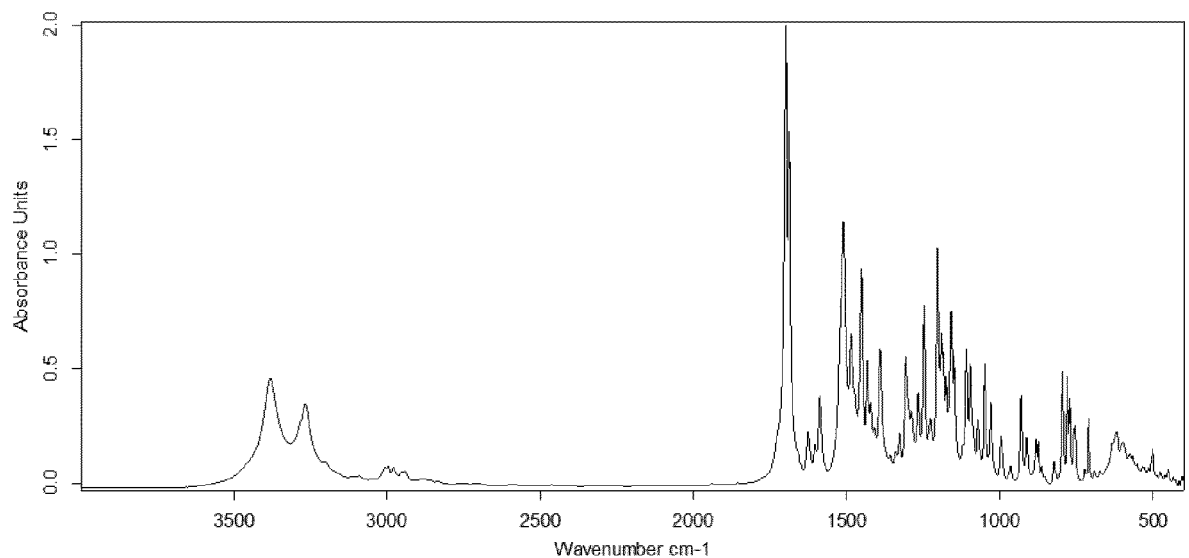

Munier-Lehmann et al., "On Dihydroorotate Dehydrogenases and Their Inhibitors and Uses," Journal of Medicinal Chemistry, Apr. 25, 2013, vol. 56, No. 8, pp. 3148-3167.
International Search Report issued in corresponding International Patent Application No. PCT/EP2019/058389, dated May 27, 2019 (4 pages).
Aiello et al., "Vascular Endothelial Growth Factor in Ocular Fluid of Patients with Diabetic Retinopathy and Other Retinal Disorders," The New England Journal of Medicine, Dec. 1, 1994, vol. 331, No. 22, pp. 1480-1487.
Dexter et al., "Activity of a Novel 4-Quinolinecarboxylic Acid, NSC 368390 [6-Fluoro-2-(2'-fluoro-1,1'-biphenyl-4-yl)-3-methyl-4-quinolinecarboxylic Acid Sodium Salt], against Experimental Tumors," Cancer Research, Nov. 1985, vol. 45, pp. 5563-5568.
Greene et al., "Protection for the Hydroxyl Group, Including 1,2- and 1,3-Diols," Protective Groups in Organic Synthesis, Third Edition, ISBNs: 0-471-16019-9 (Hardback); 0-471-22057-4 (Electronic), 1999, pp. 49.
Huang et al., "CPEC induces erythroid differentiation of human myeloid leukemia K562 cells through CTP depletion and p38 MAP kinase," Leukemia, 2004, vol. 18, pp. 1857-1863.
Loffler et al., "Dihydroorotat-ubiquinone oxidoreductase links mitochondria in the biosynthesis of pyrimidine nucleotides," Molecular and Cellular Biochemistry, 1997, vol. 174, pp. 125-129.
Lopez et al., "Transdifferentiated Retinal Pigment Epithelial Cells Are Immunoreactive for Vascular Endothelial Growth Factor in Surgically Excised Age-Related Macular Degeneration-Related Choroidal Neovascular Membranes," Investigative Ophthalmology & Visual Science, Apr. 1996, vol. 37, No. 5, pp. 855-868.

\* cited by examiner

IR Spectrum of crystalline micronized Compound (I)

Diffractogram of crystalline micronized Compound (I)

TGA Curve of crystalline micronized Compound (I)

DSC Curve of crystalline micronized Compound (I)

IR Spectrum of amorphous Compound (I)

Diffractogram of amorphous Compound (I)

DSC Curve of amorphous Compound (I)

METHOD FOR THE PREPARATION OF A 2,4,5-TRISUBSTITUTED 1,2,4-TRIAZOLONE

This application is the U.S. national phase application, pursuant to 35 U.S.C. § 371, of PCT International Application Serial No.: PCT/EP2019/058389, filed Apr. 3, 2019, designating the United States and published in English, which claims the benefit of and priority to European Patent Application Nos. 18166552.2, filed Apr. 10, 2018 and 18212916.3, filed Dec. 17, 2018. All of the aforementioned applications are incorporated herein by reference in their entirety.

The present invention provides a method for the preparation of a 2,4,5-trisubstituted 1,2,4-triazolone compound, novel intermediate compounds and their use in the methods for the preparation of said 2,4,5-trisubstituted 1,2,4-triazolone compound.

BACKGROUND

Acute myeloid leukemia (AML) is the most common acute leukemia in humans with a 5 year survival of only about 30%. The chemotherapy standard of care for AML has not changed significantly over the last decades highlighting the need for novel therapies. Around 10% of AML belong to an acute promyelocytic leukemia (APL) subtype being treated with ATRA or arsenic trioxide leading to a dramatic increase of patient survival, with overall survival rates of over 70%, unfortunately a comparable differentiation therapy for the higher incidence of non-APL AMLs is still lacking. Therefore new therapies are of high interest and medical need.

There are several preclinical studies indicating the benefit of DHODH Inhibitors in haematological and solid cancer indications. Leflunomide was linked to leukemia differentiation and also Brequinar showed in vivo efficacy on leukemia mouse models (CPEC induces erythroid differentiation of human myeloid leukemia K562 cells through CTP depletion and p38 MAP kinase, Huang M. et al, Leukemia 2004, 18, 1857-1863; also Dexter D. L. et al, Cancer Research 1985, 45, 5563-5568).

DHODH is located in the mitochondria and the enzyme responsible for the 4th and rate limiting step in de novo pyrimidine synthesis converting dihydroorotate to orotate (Dihydroorotat-ubiquinone oxidoreductase links mitochondria in the biosynthesis of pyrimidine nucleotides, Löffler M. et al, Molecular and Cellular Biochemistry 1997, 174, 125-129).

As pyrimidine production is essential for DNA and RNA synthesis DHODH is highly important for cellular proliferation. The enzyme is considered an attractive drug target for cancer, immunological, parasitic and viral diseases.

Some 2,4,5-triazolone compounds are known from U.S. Pat. No. 6,444,613 B1, WO199802422, US 2016/0251341, WO2010/077686, WO 2013/186692. The DHODH inhibitor as disclosed herein has been found to effectively inhibit DHODH and thus seems to have valuable pharmacological properties to be developed to cover the gap for non-APL AML patients mentioned above.

From WO 99/54315, WO 11/129133, WO 2013/186692, WO 2014/089140 and WO2018/077923 (PCT/EP2017/077252) methods for the preparation of triazolone compounds are known, besides others the following routes are disclosed:

Synthetic Route 1

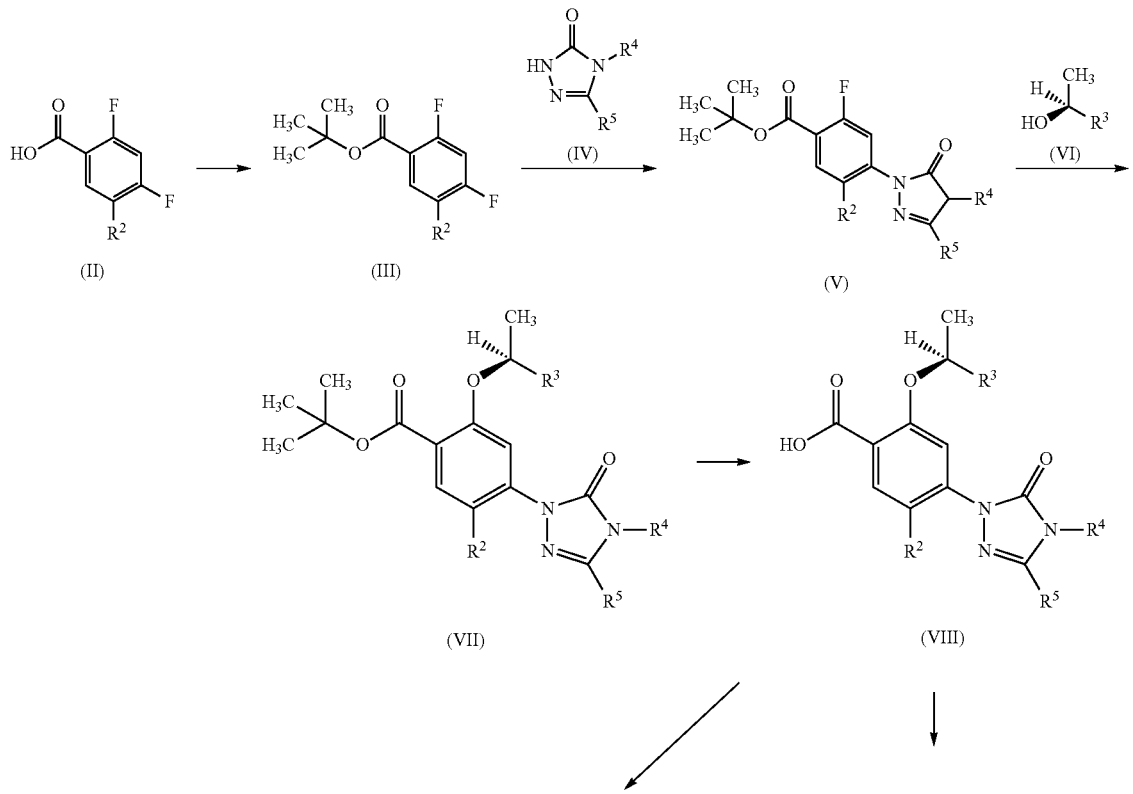

Scheme 1

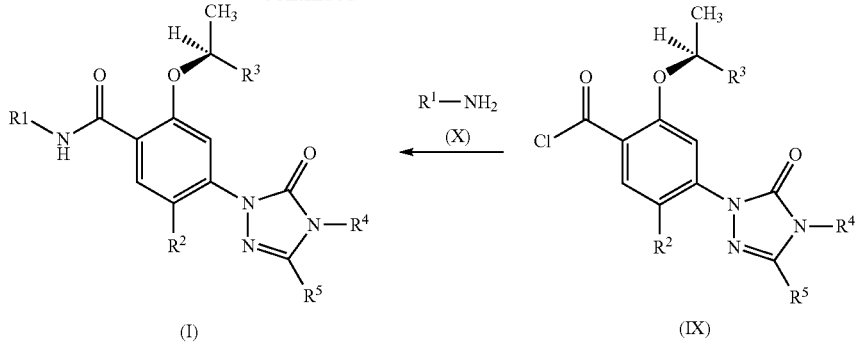

Compounds of general formulae (II), (IV), (VI) and (X) are either commercially available or can be prepared according to procedures available from the public domain.

tert-Butyl benzoates of general formula (III) can be prepared from benzoic acid derivatives of general formula (II) according to procedures available from the public domain, as understandable to the person skilled in the art. Alternatively, the tert-butyl benzoates of general formula (III) can be prepared from benzoic acid derivatives of general formula (II) by in situ formation of the the corresponding acid chlorides and subsequent reaction with tert-butanol. In situ formation of acid chlorides from benzoic acids of general formular (II) can be accomplished, for example by using oxalyl chloride or thionyl chloride, both reagents used in the presence of catalytic amount of N,N-dimethylformamide.

The formation of tert-butyl benzoates of general formula (V) can be accomplished by the reaction of triazolinones of general formula (IV) with tert-butyl benzoates of general formula (III) in the presence of a base. The use of 1,8-diazabicyclo[5.4.0]undec-7-ene as organic base in acetonitrile at 80° C. was considered preferable.

The formation of benzoic acids of general formula (VIII) can be accomplished by reaction of tert-butyl benzoates of general formula (V) with alcohols of general formula (VI) in the presence of a base, and subsequent saponification of the resulting ester of general formula (VII).

The reaction of tert-butyl benzoates of general formula (V) with alcohols of general formula (VI) can also result in transesterification, such as the tert-butoxide moiety of the tert-butyl benzoates of general formula (V) can be replaced by the alkoxide $R^3CH(CH_3)O$ moiety of the alcohols of general formula (VI). In order to obtain the benzoic acids of general formula (VIII), subsequent ester hydrolysis is required. Ester hydrolysis can be achieved by various methods which are well known to the person skilled in the art, for example by treatment of the esters with lithium hydroxide, sodium hydroxide or potassium hydroxide, in solvents, such as, for example water, 1,4-dioxane, ethanol or tetrahydrofuran or mixtures thereof.

The compounds of general formula (I) can be prepared by the reaction of the benzoic acids of general formula (VIII) with amines of general formula (X) either by in situ formation of the corresponding acid chlorides of general formula (IX) and subsequent reaction with amines of general formula (X), or by amide coupling of the benzoic acids of general formula (VIII) with amines of general formula (X).

Synthetic Route 2

Scheme 2

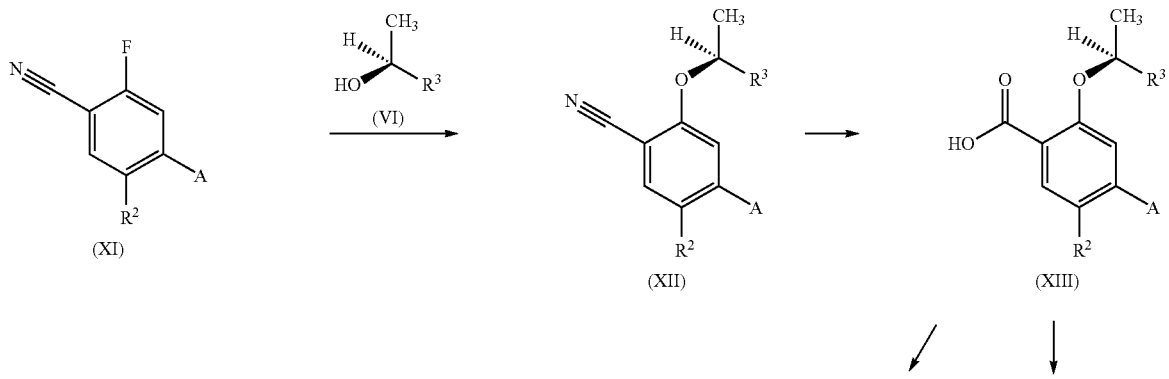

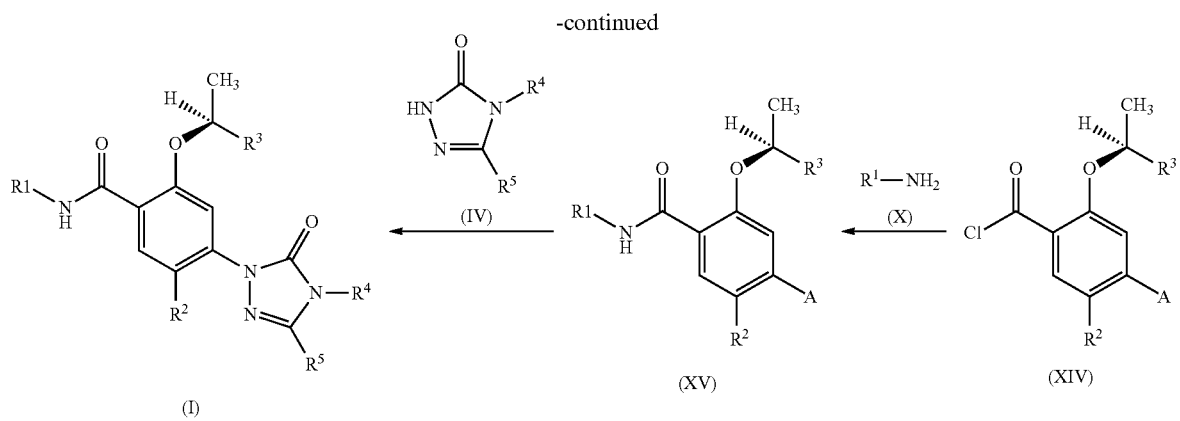

Again the starting material compounds of general formulae (XI), (IV), (VI) and (X) are either commercially available or can be prepared according to procedures available from the public domain, as understandable to the person skilled in the art.

Nitriles of general formula (XII) can be prepared from nitriles of general formula (XI) and with alcohols of general formula (VI) according to procedures available from the public domain, as understandable to the person skilled in the art. Alternatively, for alcohols of sufficiently high acidity the use of potassium carbonate was preferable.

The formation of benzoates of general formula (XIII) can be accomplished by hydrolysis of nitriles of general formula XII using strong acids or bases. sodium hydroxide in ethanol at 90° C. was indicated preferable.

The compounds of general formula (XV) can be prepared by the reaction of the benzoic acids of general formula (XIII) with amines of general formula (X) either by in situ formation of the the corresponding acid chlorides of general formula (XIV) and subsequent reaction with amines of general formula (X), or by amide coupling of the benzoic acids of general formula (XV) with amines of general formula (X).

Compounds according to the invention of general formula (I) can be prepared from halides of general formula (XV) and from triazolones of general formula (IV) using transition metals as catalysts.

Intermediates of general formula (XV) can be reacted with a suitable triazolone of general formula (IV), such as, for example 3-ethyl-4-methyl-1H-1,2,4-triazol-5(4H)-one, in the presence of a suitable base, such as, for example cesium carbonate, and a suitable palladium catalyst, such as for example (1E,4E)-1,5-diphenylpenta-1,4-dien-3-one-palladium, in the presence of a suitable ligand, such as for example (9,9-dimethyl-9H-xanthene-4,5-diyl)bis(diphenylphosphine), in a suitable solvent system, such as, for example, dioxane, in a temperature range from room temperature to the boiling point of the respective solvent, preferably the reaction is carried out at 100° C. to furnish compounds of general formula (I). Alternatively palladium catalysts can be used.

Synthetic Route 3:

Scheme 3

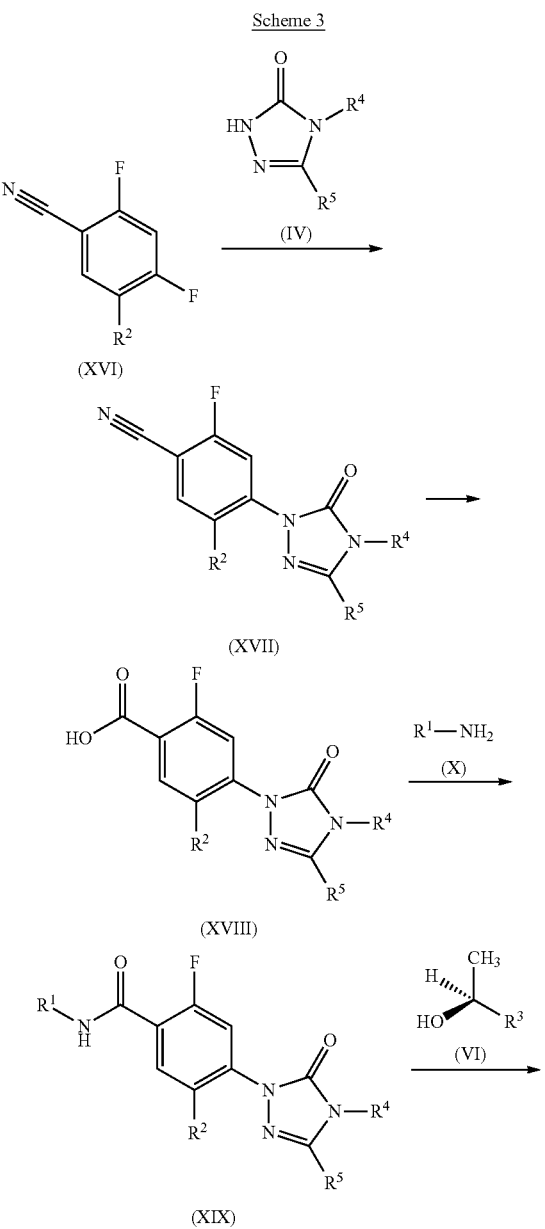

-continued

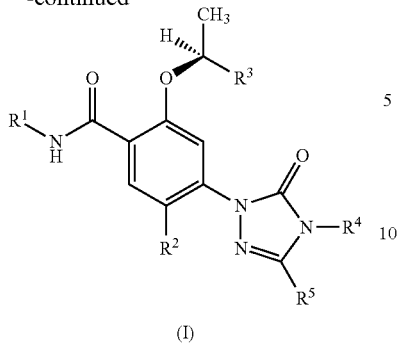

(I)

Compounds of general formulae (XVI), (IV), (VI) and (X) are either commercially available or can be prepared according to procedures available from the public domain, as understandable to the person skilled in the art.

Nitriles of general formula (XVII) can be prepared from nitriles of general formula (XVI) and triazolinones of general formula (IV) in the presence of a base. The use of potassium carbonate as base in acetonitrile at 80° C. was considered preferable.

The formation of benzoates of general formula (XVIII) can be accomplished by hydrolysis of nitriles of general formula XVII using strong acids or bases. The use of sodium hydroxide in ethanol at 85° C. was considered preferable.

The compounds of general formula (XIX) can be prepared by the reaction of the benzoic acids of general formula (XVIII) with amines of general formula (X) by amide coupling. Suitable coupling reagents are proposed.

The formation of compounds of of general formula (I) can be accomplished by reaction of amides of general formula (XIX) and alcohols of general formula (VI) in the presence of a base. Bases that can be employed for the reaction of amides of general formula (XIX) with alcohols of general formula (VI) are for example sodium hydride, sodium tert-butanolate, potassium tert-butanolate, or cesium carbonate. Sodium hydride was considered to be preferably used as organic base.

From WO2018/077923 (PCT/EP2017/077252) Compound (I) falling under the scope of formula (I) is known.

Compound (I) may be synthesized according to one of the routes mentioned above but all of these synthetic routes suffer from significant disadvantages which pose especially problems at larger scale:

For industrial implementation and the production of larger kilogram amounts, the preparative processes and routes described above are suitable to only a limited extent. Employing suitable building blocks to synthesize Compound (I), the most significant drawbacks can be summarized as follows:

Synthetic Route 1:
Substitution with the unprotected hydroxy-substituted triazolone (IV) in the first step gave a mixture of compounds.
The second nucleophilic substitution step is very slow, even under the most convenient conditions for the substitution with trifluoroisopropanol (VI) in the second step (a reaction for 24 h with potassium phosphate as a base and DMSO as a solvent at a temperature of 90° C.). However, this reaction was accompanied by hydrolysis of the tert-butyl ester in the starting material (V) as well as the reaction product (VII).

Standard reagents for acid chloride formation, for example oxalyl chloride or thionyl chloride easily form hydrogen chloride which leads to (partial) deprotection of acid-labile protecting groups and potientially chlorination of the free hydroxy group. In addition, the use of N,N-dimethylformamide as catalysts in combination with these reagents leads to formation of N,N-dimethylcarbamoyl chloride, a known carcinogen, that needs to be controlled and even may not be purged to the extent that is needed for pharmaceutical products according to the appropriate regulatory guidelines.

All synthetic intermediates were obtained as oil. Hence, impurities could only be purged by extensive purification efforts such as chromatography. This leads to additional effort, cost and significant reduction of yield—especially on industrial scale.

Synthetic Route 2:

Starting material (XI) is comparatively more expensive to a trifluoro-substituted starting material. In case of chiral trifluoroisopropanol (xxx6), starting material (VI) is very expensive but introduced in the first synthetic steps. This leads to significant cost due to material loss in the subsequent steps and thus represents an economically unfavorable process.

Standard reagents for acid chloride formation, for example oxalyl chloride or thionyl chloride in combination with the use of N,N-dimethylformamide as catalyst leads to formation of N,N-dimethylcarbamoyl chloride, a known carcinogen, that needs to be controlled and even may not be purged to the extent that is needed for pharmaceutical products according to the appropriate regulatory guidelines.

Palladium-mediated coupling of (IV) and (XV) by the use of an expensive homogenous catalyst (ligand and precious metal) and leads to a complex reaction product mixture on the final stage. Hence, these impurities could only be purged by extensive purification effort such as preparative reverse phase HPLC separation. This leads to significant effort, waste generated and cost—especially on industrial scale. In addition, Palladium levels in the final product needs to be controlled and even may not be purged to the extent that is needed for pharmaceutical products according to the appropriate regulatory guidelines.

Synthetic Route 3:

Usability of synthetic route 3 is of limited industrial use due to very low conversion of mono-substituted amide (XIX) to the desired product (I) due to comparatively low electrophilicity of the amide, which leads to side product formation and extensive purification efforts. This leads to additional effort, cost and very significant reduction of yield—especially on industrial scale.

It was therefore desirable to develop a new synthesis, which circumvents these disadvantages and is suitable for large scale production.

Thus, the object of the present invention is to provide a method for preparation of Compound (I) which was not provided by the state of the art and at the same time does not suffer from the disadvantages as outlined above.

Compound (I)

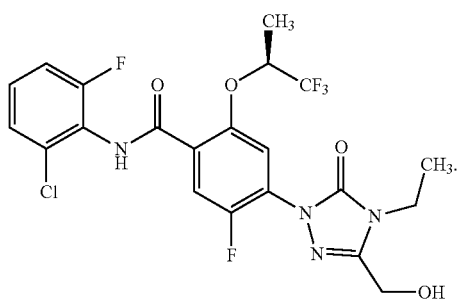

The process as described in more detail below is neither covered nor are the intermediates as claimed disclosed in the state of the art It has thus been found that the methods to prepare 2,4,5-trisubstituted 1,2,4-triazolone Compound (I), N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, as described herein not only differ from the methods as disclosed in the state of the art but are unexpectedly advantageous, well reproducable and result in high yields and quality.

DESCRIPTION OF THE INVENTION

In accordance with a first aspect, the present invention provides methods for the preparation of the DHODH inhibitor Compound (I), N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide or a tautomer, an N-oxide, a salt, a salt of a tautomer or a salt of an N-oxide thereof comprising the step of allowing an intermediate compound of formula (A7):

(A7.1)

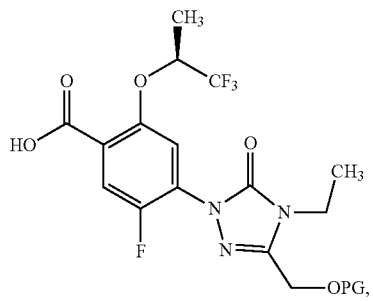

wherein PG is a protecting group selected from Tetrahydropyranyl (THP), Tetrahydrofuranyl (THF), 1-Ethoxyethyl (EE), tert-Butyl (t-Bu), tert-Butoxymethyl, Methoxyethoxymethyl (MEM), to react with a compound of formula (xxx7):

(xxx7)

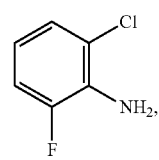

optionally in a suitable aprotic solvent, by addition of a suitable base, optionally under activation of the carboxylic acid group or by generation of an intermediate acid chloride using a suitable reagent, and either adding a reagent for cleaving the protecting group or isolating compound (A9)

(A9.1)

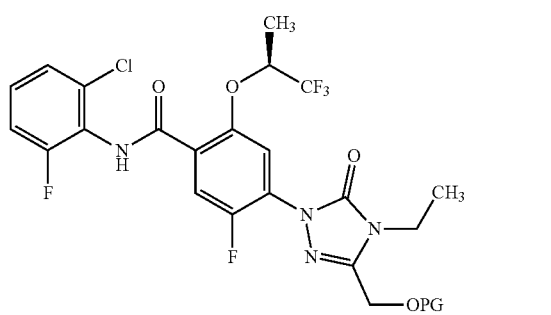

and subsequently adding a reagent for cleaving the protecting group, thereby providing Compound (I):

Compound (I)

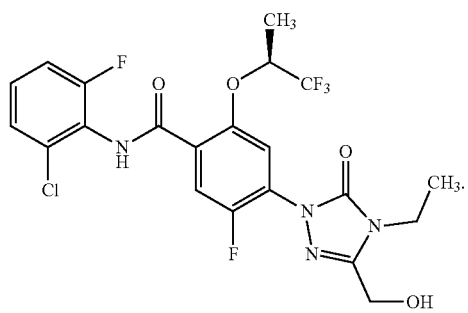

In accordance with a second aspect, the present invention provides methods for the preparation of the DHODH inhibitor Compound (I), according to the following Scheme 4:

Scheme 4
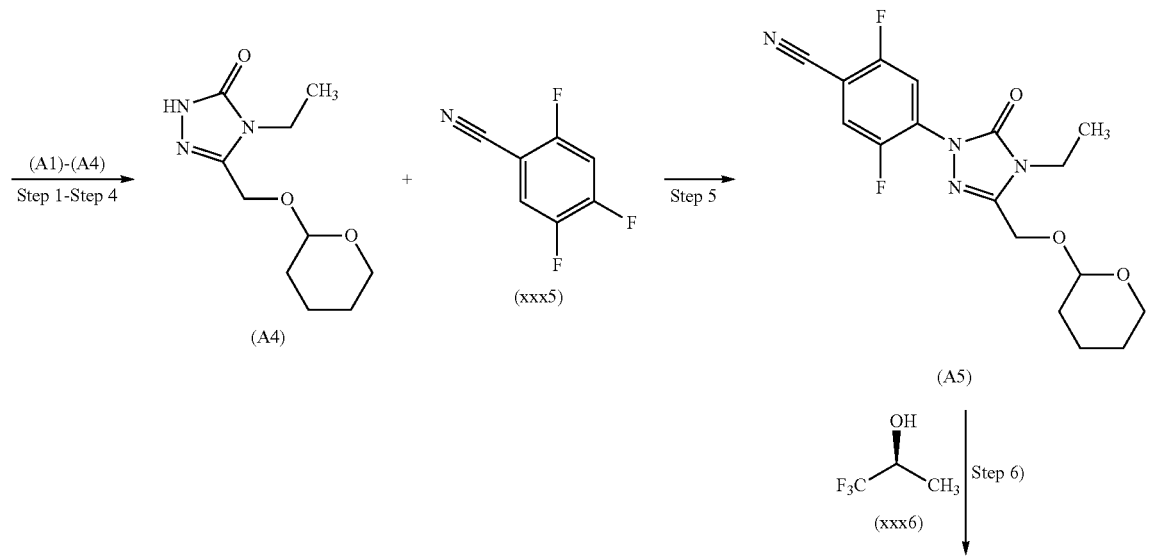
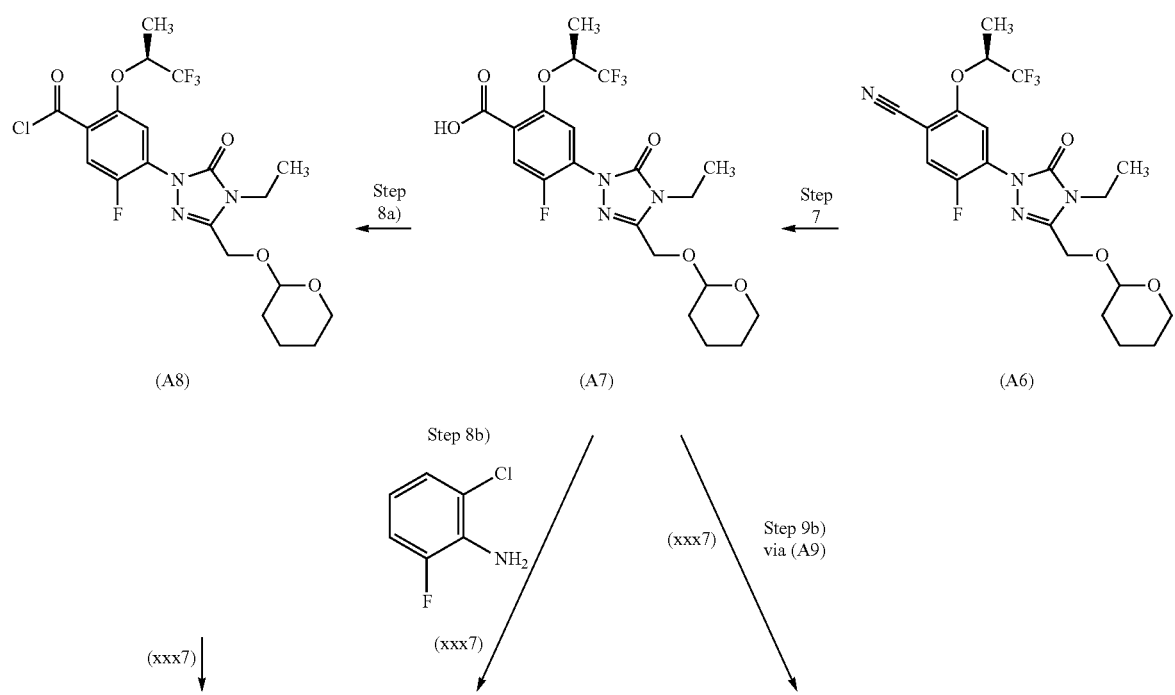

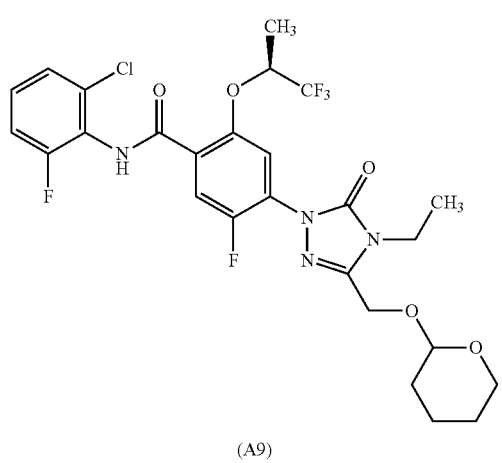

(A9)

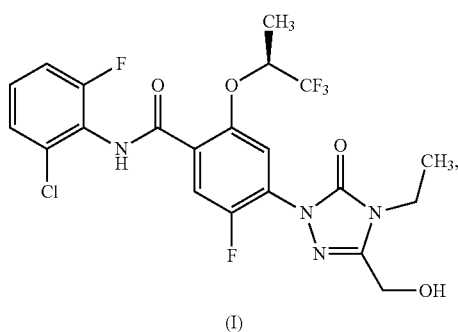

(I)

optionally further converting Compound (I) into an N-oxide, a salt or a salt of an N-oxide.

In an embodiment of the second aspect the invention provides a method of preparing Compound (I) according to the disclosure of the examples.

In accordance with an embodiment of the first and the second aspect, the present invention provides methods for the preparation of Compound (I) comprising the step of allowing an intermediate compound of formula (A7):

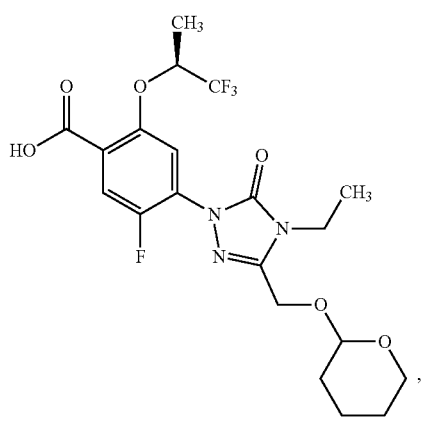

to react with a compound of formula (xxx7):

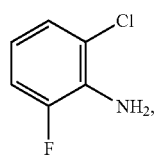

optionally in a suitable solvent, optionally under activation of the carboxylic acid group or generation of an intermediate acid chloride using a suitable agent, optionally cleavage of the protecting group, thereby providing Compound (I):

Compound (I)

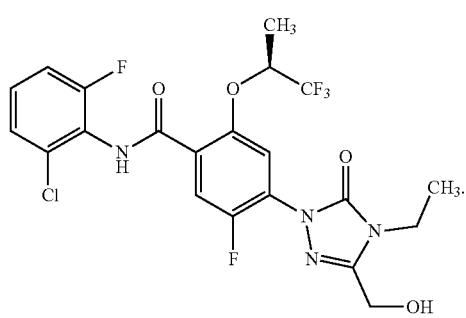

In a third aspect the invention provides a crystalline form of Compound (I), N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, which is the crystalline form A, a process for its preparation and pharmaceutical compositions comprising said crystalline form and its use for the treatment of hyperproliferative disorders, especially cancer.

Definitions

Where the plural form of the word compounds, salts, polymorphs, hydrates, solvates and the like, is used herein, this is taken to include also a single compound, salt, polymorph, isomer, hydrate, solvate or the like.

For any ranges being defined herein it is meant to include both the lower and the upper limit within the range.

The term "activation of the carboxylic acid group" means addition of any reagent facilitating amide coupling which is known by the skilled person, such as e.g. COMU® (1-Cyano-2-ethoxy-2-oxoethylidenaminooxy)dimethyl-amino-morpholino-carbenium hexafluorophosphate), HATU (O-(7-Azabenzotriazole-1-yl)-N,N,N',N'-tetramethyluronium-hexafluorphosphate), HBTU (2-(1H-benzotriazole-1-yl)-1,1,3,3-tetramethyluronium-hexafluorophosphate), TBTU (2-(1H-benzotriazole-1-yl)-1,1,3,3-tetramethyluronium tetrafluoroborate), carbonyl diimidazole, carbodiimides, 2-chloro-1-methylpyridinium iodide, propylphosphonic anhydride (T3P®) and reference is made to Montalbetti et al; Tetrahedron, 61(205), 10827-10852.

The term "crystallization" means any procedure known to the person with ordinary skill to let a product initially obtained as an oil or a mixture containing side products to crystallize, e.g. by dissolving, cooling, or adding another solvent in which the product is not soluble, or adding some crude crystals or evaporating part of the solvent.

The term "recrystallization" means that a solid had been obtained already but the solid was e.g. dissolved again and cooled, adding another solvent in which the product is not soluble, or evaporating part of the solvent.

The term "internal temperature" means the temperature as measured from inside a reaction mixture.

The term "purification" includes destillation, crystallization, recrystallization and chromatography.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

The term "room temperature" is meant to be within a range of 20°-24° C.

The term "short period of time" in the context of a chemical synthesis means 5-30 min, preferably 10-20 min.

The term "suitable agents" in the context of the preparation of an intermediate acid chloride (A8) includes but is not limited to, phosphoryl chloride, Ghosez's reagent (1-chloro-N,N,2-trimethyl-1-propenylamine).

The term "sulfonic acids" includes for example methanesulfonic acid, p-toluenesulfonic acid, Dowex resin.

The term "usual work-up" or "isolation" means isolating the reaction product from the reaction mixture by methods of a person skilled in the art comprising but not limited to steps like e.g. separating organic phase from aqueous phase, drying the organic phase with e.g. alkali sulfates such as sodium sulfate or potassium sulfate, or magnesium sulfate or calcium sulfate, filtering and evaporating the solvent to obtain crude product, dissolving again the crude product and cooling down to crystallize and optionally add further steps of purification. If these steps are expressly mentioned, the method may be part of the invention.

Unless otherwise noted, generally acceptable aprotic solvents for the process (where necessary) may be, for example, ethers such as diethyl ether, tert-butyl methyl ether, tetrahydrofuran (THF), 1,4-dioxane or 1,2-dimethoxyethane, hydrocarbons such as benzene, toluene, xylene, hexane or cyclohexane, halogenated hydrocarbons such as dichloromethane, trichloromethane, carbon tetrachloride, 1,2-dichloroethane, trichloroethylene or chlorobenzene, or other solvents such as acetone, acetonitrile, ethyl acetate, pyridine, dimethylsulfoxide (DMSO), N,N-dimethyl-formamide (DMF) or N methylpyrrolidinone (NMP). It is also possible to use mixtures of these solvents.

DETAILED DESCRIPTION

In general there are several possibilities for the order of possible reaction steps to add the substituents of the central phenyl ring moiety resulting in the final compound of formula (I) illustrated as follows:

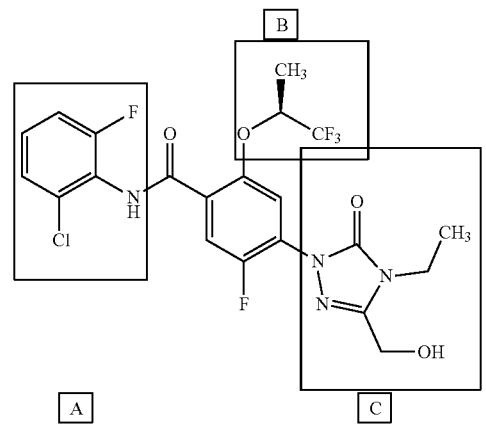

One could start with component A to the central phenyl moiety, then adding component B and subsequently component C or starting with addition of component B, adding component C and finally component A etc. Some routes are already known as outlined above in the background section. The route as disclosed in the invention has not yet been disclosed in the state of the art.

The object of the invention is achieved by the provision of the following method as described herein.

As a very general description illustrating the principle of the synthesis route of the invention, a suitably hydroxy-protected compound (A4) (component C) is added to the central tetra substituted phenyl ring, 3,4,5-trifluorobenzonitrile, then the alcohol substituent (component B) is added resulting in an intermediate compound of formula (A6) which is oxidized to arrive at compound (A8) and subsequently forming the amide with the dihalogenated second phenyl ring (component A).

Description of the Synthesis Route According to Scheme 4 in More Detail:

The intermediate compound A4 needed for the first step of the synthesis of Scheme 4 described above is prepared by the route as illustrated in Scheme 5

Ia). Synthesis of Intermediate (A4):

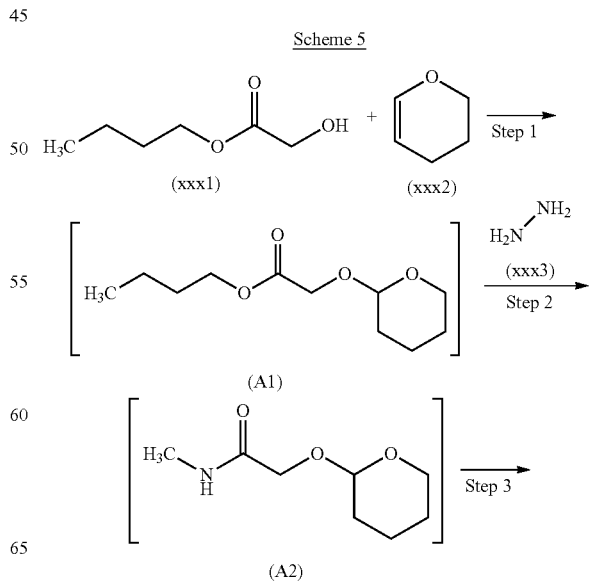

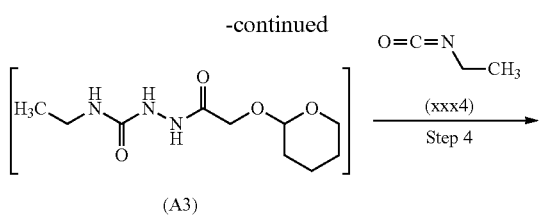

(A3)

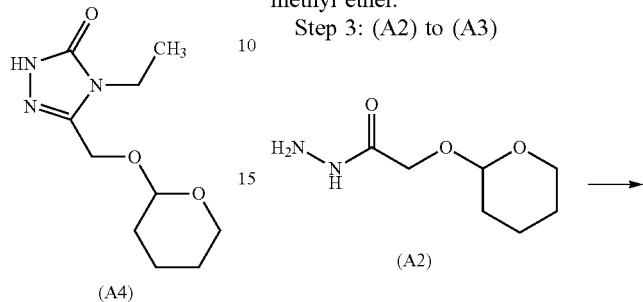

(A4)

Step 1: (xxx1) to (A1):

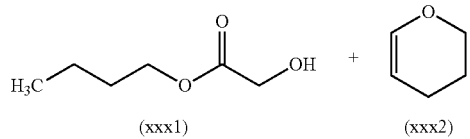

(xxx1)        (xxx2)

Butyl-hydroxyacetate was reacted with 3,4-dihydro-2H-pyran under appropriate acidic conditions, e.g. p-toluenesulfonic acid, pyridinium p-toluenesulfonate (PPTS), hydrochloric acid, preferably p-toluenesulfonic acid, (or other suitable agents as described in: Protective Groups in Organic Synthesis ISBNs: 0-471-16019-9 (Hardback); 0-471-22057-4 (Electronic), pp. 49) in an aprotic solvent, e.g. toluene, dichloromethane, preferably dichloromethane at a temperature range of 20°-41° C. The crude product (A1) as obtained by usual drying process and evaporation of the organic phase may be purified by destillation in vacuum (boiling point 79°-85° C. at ca. 0.5 mbar) or may preferably be used as crude product for the following reaction step.

In a preferred embodiment a reactor is charged with dichloromethane, butyl-hydroxyacetate is added at room temperature, subsequently 4-toluolsulfonic acid is added at room temperature and subsequently 3,4-dihydro-2H-pyran is added and the reaction mixture is stirred and cooled to room temperature.

Step 2: (A1) to (A2)

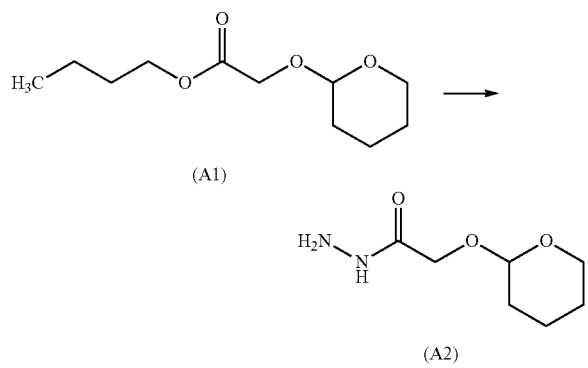

A1 is reacted with hydrazine hydrate at slight reflux conditions. The reaction can optionally be optionally run in a suitable solvent, e.g. methanol, n-butanol. The mixture subsequently is cooled to room temperature and preferably directly introduced into the next step. The product (A2, see also DE 2156472) may optionally be obtained by aqueous work-up with a suitable solvent, e.g. toluene, tert-butyl methyl ether.

Step 3: (A2) to (A3)

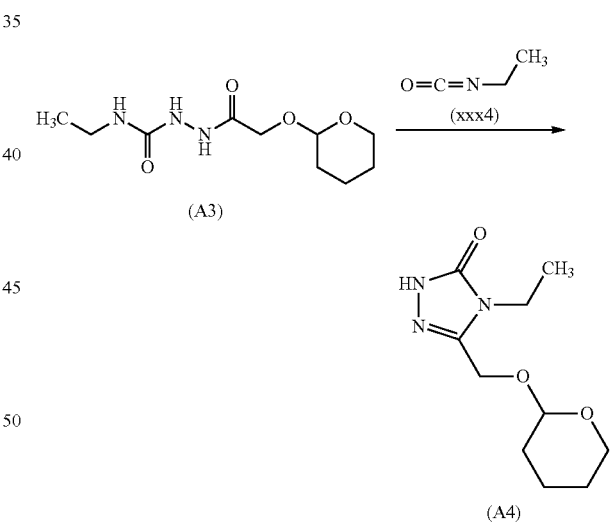

An aqueous mixture is produced of the crude product (A2) and water and is cooled to about 8°-15° C. Ethylisocyanate is added slowly. Then the reaction mixture is allowed to warm to room temperature and the thus resulting mixture is directly used for the following step or may be isolated by filtration.

Step 4: (A3) to (A4)

To the crude reaction mixture as obtained under Step 3 an aqueous solution of sodium hydroxide, preferably a solution containing 50% sodium hydroxide, is added slowly keeping the temperature of the mixture at room temperature. After complete addition the reaction mixture is heated, preferably to 75°-79° C., most preferably to 79° C. (reflux). At end of reaction time the mixture is cooled to room temperature, its pH is adjusted to neutral (pH ca. 6-8), preferably to pH=7.3 by addition of a strong protic acid such as HCl, $HNO_3$, sulfonic acids, $CH_3COOH$ and $H_2SO_4$, preferably 1N hydrochloric acid. A suitable solvent is added, preferably dichloromethane, and the suspension is stirred for an additional short period of time and subsequently a usual work-up is performed. The resulting residue is dissolved in e.g. cyclohexane, diisopropyl ether, preferably diisopropyl ether and slowly cooled to 20°-25° C. Surprisingly the product crystallizes well and can be isolated by filtration, while relevant impurities remain in the mother liquor and are thus separated.

Intermediate (A4) is new and thus one aspect of the invention is the intermediate (A4) as well as its use for the preparation of Compound (I).

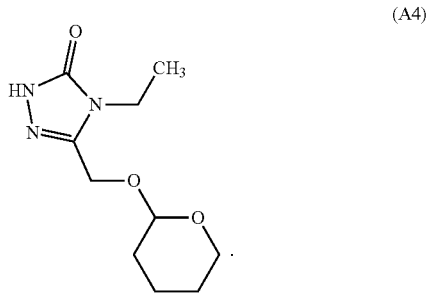 [SMILES: CCn1c(COC2CCCCO2)n[nH]c1=O]

Ib) Alternative Route Options Towards Intermediate (A4):

Alternatively the intermediate compound of formula A4 can be prepared following Scheme 6:

The schemes and procedures described above illustrate the alternative synthetic routes to the intermediate compound (A4), the starting material in the synthesis route of scheme 4 for the preparation of Compound (I).

A:

Phenyl chloroformate is reacted with ethylamine in a suitable solvent, e.g. water in order to produce phenylethylcarbamate which subsequently is reacted with hydrazine in order to obtain N-ethylhydrazinecarboxamide. This crude reaction product can be reacted with either hydroxyacetic acid or a hydroxyacetic acid ester such as e.g. hydroxyacetic acid methyl ester, hydroxyacetic acid ethyl ester, hydroxyacetic acid propyl ester, hydroxyacetic acid butyl ester, in a suitable solvent, e.g. 2-propanol to obtain N-ethyl-2-glycoloylhydrazinecarboxamide which can be cyclized to 4-ethyl-5-(hydroxymethyl)-2,4-dihydro-3H-1,2,4-triazol-3-one (sodium hydroxide, water). By subsequent reaction with 3,4-dihydro-2H-pyran under conditions as disclosed above (e.g. dichloromethane (DCM), HCl) compound (A4) is obtained.

B:

Phenylethylcarbamate can be reacted with 2-(tetrahydro-2H-pyran-2-yloxy)acetohydrazide (A2) which is obtained by Step 2 as disclosed above to obtain compound (A3) which in turn can be reacted with ethylisocyanate as disclosed in step 3 to produce compound (A4).

C:

N-ethylhydrazinecarboxamide as obtainable by route A can be reacted with butyl (tetrahydro-2H-pyran-2-yloxy)

Scheme 6

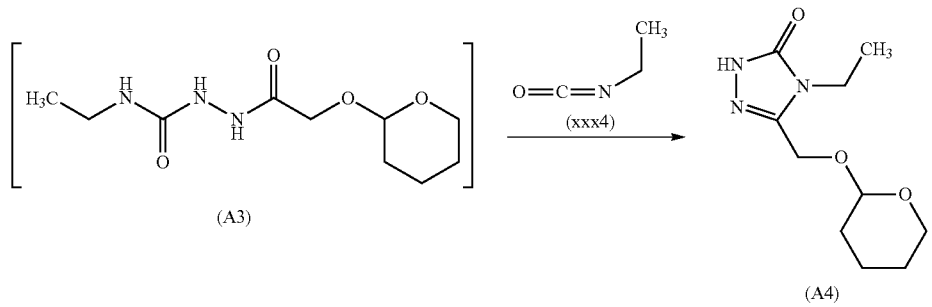

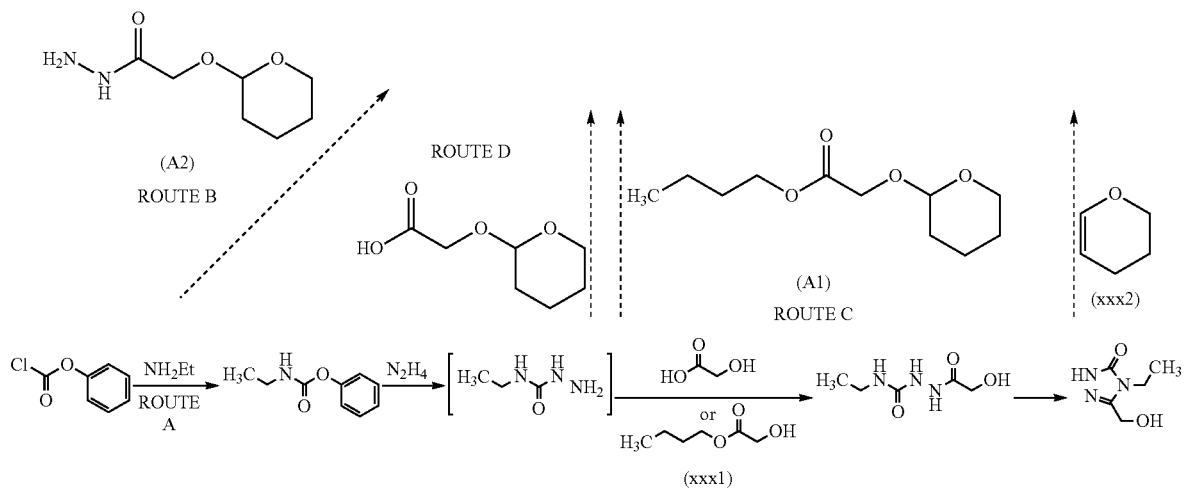

acetate (A1) as obtained by step 1 to obtain compound (A3) which in turn can be reacted with ethylisocyanate as disclosed in step 3 to produce compound (A4).

D:

N-ethylhydrazinecarboxamide as obtainable by route A can be reacted with (tetrahydro-2H-pyran-2-yloxy)acetic acid to obtain compound (A3) which in turn can be reacted with ethylisocyanate as disclosed in step 3 to produce compound (A4).

II. Synthesis of Compound (I) by Using Intermediate Compound (A4)

Step 5: (A4) to (A5)

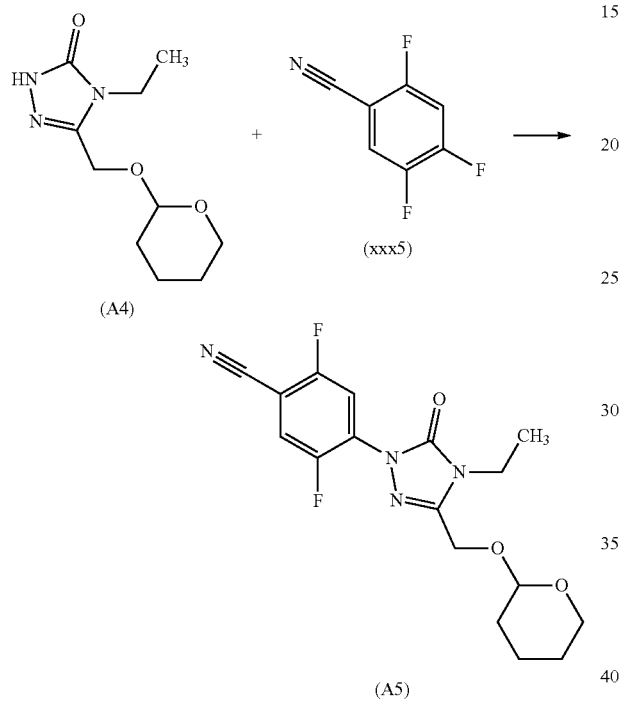

(A4)

(xxx5)

(A5)

4-Ethyl-5-[(tetrahydro-2H-pyran-2-yloxy)methyl]-2,4-dihydro-3H-1,2,4-triazol-3-one (A4) was allowed to react with 2,4,5-trifluorobenzonitrile (CAS no. 98349-22-5, Sigma-Aldrich) in a polar aprotic solvent such as e.g. THF, DMSO, DMF, acetonitrile, preferably acetonitrile and a suitable base such as e.g. 1,8-diazabicyclo[5.4.0]undec-7-ene, potassium carbonate, cesium carbonate, potassium tert-butoxide, sodium hydride, potassium phosphate, preferably potassium phosphate was added. The mixture was stirred at 60°-82° C., preferably at 70°-73° C. for a time period of 18-28 h, preferably 20 h, and allowed to cool to room temperature. Water was added and the mixture again stirred for 10-20 min, preferably for 15 min. A work-up as known by a person with ordinary skill in the art was performed. The residue obtained was dissolved in ethanol, water was added and the solution stirred for a time period of 18-32 h, preferably 21 h, the solids isolated, dried to obtain 4-{4-ethyl-5-oxo-3-[(tetrahydro-2H-pyran-2-yloxy)methyl]-4,5-dihydro-1H-1,2,4-triazol-1-yl}-2,5-difluorobenzonitrile, optionally a purification can be achieved using preparative chromatography.

The search for suitable reagents and reaction conditions (base, solvent, temperature) for this reaction was crucial and a lot of failures were to be accepted, such as the reactivity of (xxx5) towards nucleophilic aromatic substitution had to be balanced towards high turnover at optimum selectivity for formation of (A5).

Substitution with an appropriately protected hydroxy-substituted triazolone was needed in order to give clean conversion to intermediate (A5) in good purity. THP was identified after substantial experimentation to serve as appropriate hydroxy protecting group throughout the synthesis (as discussed further below).

It was extraordinary crucial to obtain the product A5 as a solid and to be able to remove relevant impurities such as not reacted starting material (xxx5) and impurities resulting from undesired reactions of (A5) which remain in the mother liquor and which would otherwise result in complex impurity profiles on subsequent steps.

The work in order to find the conditions for this step disclosed herein was more than usual experimentation a person with ordinary skill is conducting.

Step 6: (A5) to (A6)

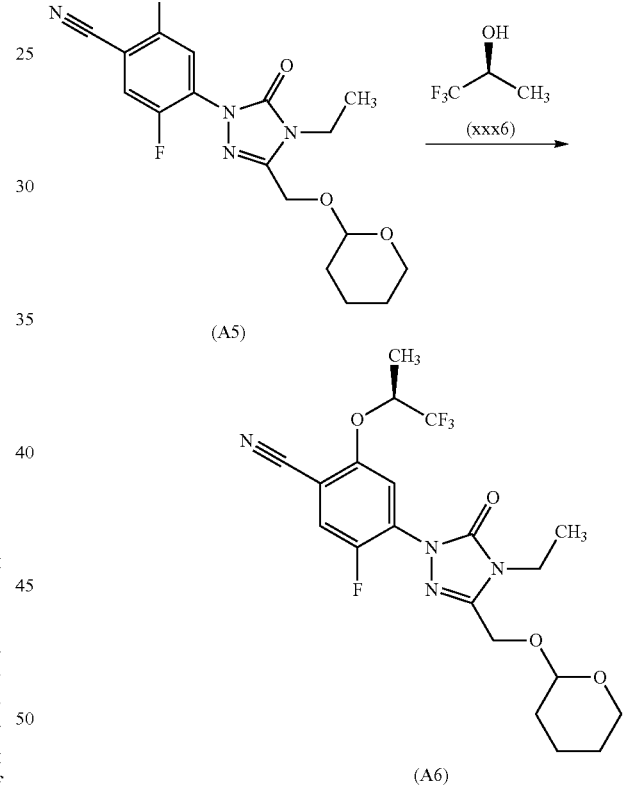

(A5)

(xxx6)

(A6)

The Intermediate compound (A5) was dissolved in a polar aprotic solvent, e.g. DMSO, acetonitrile, preferably in acetonitrile, (S)-1,1,1-trifluoro-2-propanol and potassium phosphate were added. The mixture was heated to 70°-90° C., preferably to 73° C. and stirred for a time period of 16 h-32 h, preferably for 24 h, then cooled to room temperature, water was added and the mixture stirred for an additional short period of time. The usual work-up was performed. The crude product was used for the following reaction step without further purification, optionally purification can be achieved using preparative chromatography.

Among the synthetic equivalents tested for the carboxylic acid substituents, such as carboxylic acid esters, only the benzonitrile (A5) exhibits sufficient reactivity and reaction selectivity in combination with high conversion towards (A6).

The search for suitable reagents and reaction conditions (base, solvent, temperature) for this reaction was crucial and a lot of failures were to be accepted, as the reactivity of (A5) and (xxx6) towards nucleophilic aromatic substitution is low, and high turnover and selectivity was desired. Again, the work in order to find the conditions for this step disclosed herein was more than usual experimentation a person with ordinary skill is conducting Step 7: (A6) to (A7)

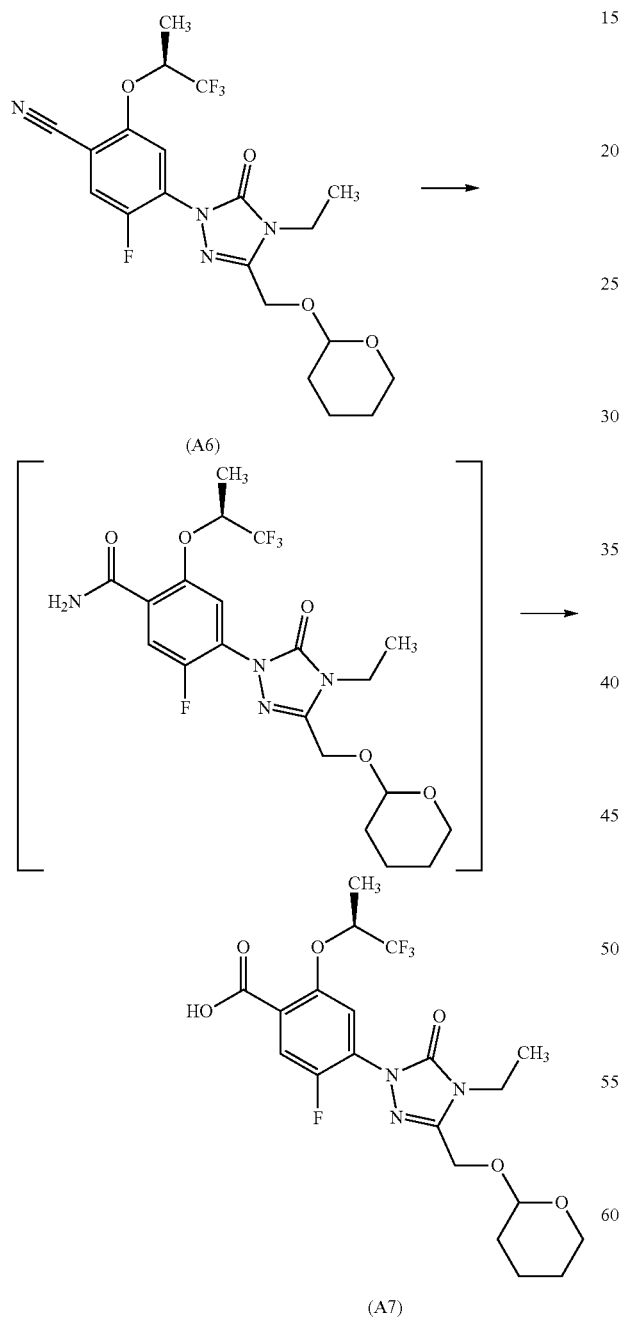

Crude (A6) was dissolved in a polar protic solvent, such as methanol, ethanol, propanol, preferably ethanol, an aqueous hydroxide solution formed by a strong base such as e.g. alkali hydroxides, such as sodium hydroxide, potassium hydroxide, or an other hydroxide such as e.g. alkaline earth hydroxides, such as calcium hydroxide or magnesium hydroxide, preferably sodium hydroxide, at a concentration of 1N-4N, preferably 2N, was added and the mixture stirred at 65°-80° C., preferably at 70° C., for a time period of 24 h-40 h, preferably for 28 h. After cooling to room temperature the mixture was acidified to pH3-6, preferably pH4 using a strong protic acid such as $HNO_3$, sulfonic acids, $CH_3COOH$, acetic acid, citric acid and $H_2SO_4$, hydrochloric acid, preferably hydrochloric acid, at any suitable concentration, specifically at a concentration equal to the concentration of the hydroxide solution used, preferably a 2N hydrochloric acid, and a suitable non-water miscible solvent was added, e.g. ethyl acetate, tert-butyl methyl ether, preferably tert-butyl methyl ether, and the mixture stirred for a short period of time. The usual work-up was performed. The residue was dissolved in diisopropyl ether at 55°-65° C., preferably 60° C., slowly cooled to room temperature and stirred for 14-18 h, preferably for 16 h. Tetrahydrofuran (THF) was added and the suspension cooled to 0°-5° C. and stirred for another time period of 50-70 min, preferably 1 h. The solids of (A7) were isolated and dried.

The search for a suitable reaction and work-up conditions for this reaction was crucial, and a lot of failures were to be accepted:
  Sufficient reaction time is needed to fully convert the benzamide intermediate to the desired product
  Efficient aqueous work-up is only possible at acidic pH, due to substantial aqueous solubility of (A7) at pH>6. Surprisingly, the product (A7) is stable under the preferred work-up conditions (pH4), while the THP protecting group is known to be unstable under acidic conditions
  It was extraordinary crucial to obtain the product (A7) as a solid to deplete remaining impurities from the previous process steps to reach sufficient quality of this key intermediate to the extent that is needed for achieving final product quality in line with pharmaceutical regulatory guidelines. The use of an unusual crystallization solvent mixture (diisopropyl ether, THF) surprisingly gave a solid product of appropriate quality while avoiding sticky residues as observed for diisopropyl ether without co-solvent.

Step 8a): (A7) to (A8) to (A9)
Method A

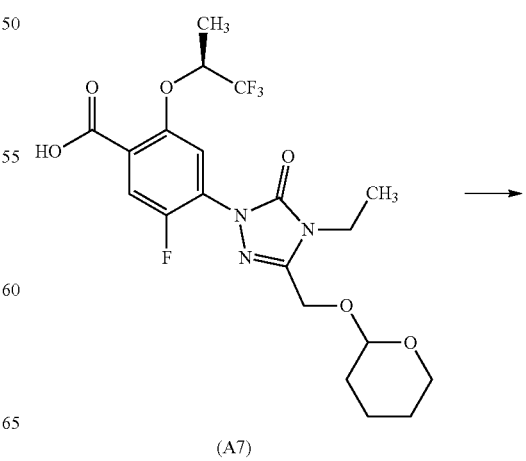

(A7)

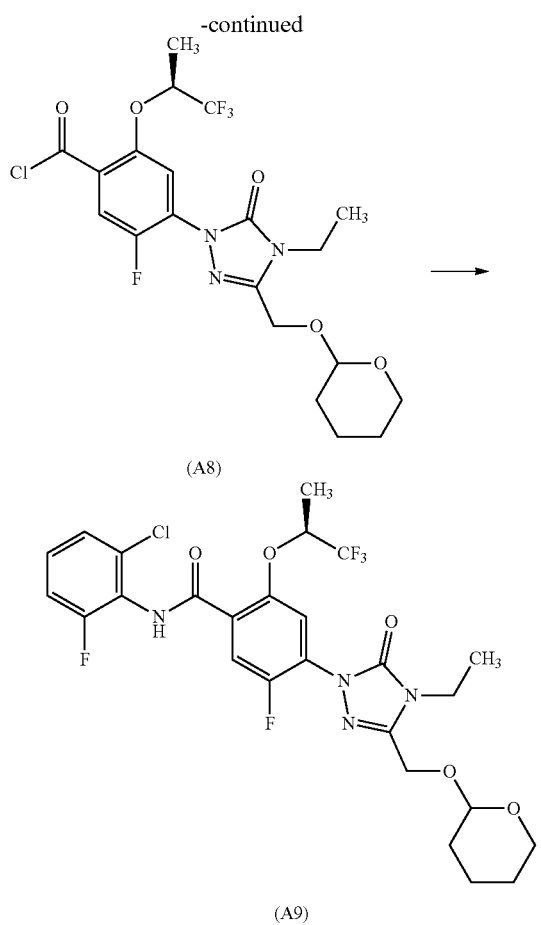

(A8)

(A9)

In a first vessel intermediate (A7) was dissolved in a suitable aprotic solvent, such as toluene, dichloromethane, preferably dichloromethane, at 0-25° C., preferably at room temperature. 1-Chloro-N,N,2-trimethyl-1-propenylamine was added and the mixture stirred for 30 min to 2 h, preferably 30 min. The so obtained crude product solution of (A8) was combined with a solution of the second vessel described below.

In a second vessel 2-chloro-6-fluoroaniline (1.2 to 10 molar equivalents to (A7), preferably 1.5 equivalents) was dissolved in a suitable aprotic solvent, such as dichloromethane, toluene, preferably dichloromethane. Pyridine was added and the mixture was cooled to 0°-5° C.

The contents of the first vessel was slowly added to the second vessel prepared as described and the resulting complete mixture stirred for about an hour, subsequently warmed up to room temperature, optionally by heating. To this mixture water was added, the mixture again stirred for a short period of time and a usual work-up performed. The crude product so obtained was diluted with dichloromethane and [a] filtered through silica gel. The filtrate was evaporated and the crude product (A9) used for the next step. Optionally, the crude product was [b] further purified by silica gel chromatography with n-heptane/ethyl acetate as eluent. The combined product-containing fractions were evaporated to obtain purified product (A9).

The search for a suitable reaction and work-up conditions in order to find the conditions for this step disclosed herein was extraordinary difficult and was more than usual experimentation a person with ordinary skill is conducting:

Only a very limited set of solvents is suitable for efficiently facilitating both desired transformations while avoiding formation of substantial amounts of undesired by-products.

Within the range of reagents tested, only the quite unusual reagent 1-Chloro-N,N,2-trimethyl-1-propenylamine was found to efficiently promote the desired transformation to (A8) while preserving the acid-labile THP protecting group upon scale-up.

The addition of an over-stoichiometric amount of 2-chloro-6-fluoroaniline and reaction at low temperature was crucial to avoid formation of an imide impurity formed by an undesired second acetylation of (A9) by (A8)

Step 8b): (A7) to (A9)

Method B (A7) was dissolved in a suitable aprotic solvent, such as e.g. acetonitrile, toluene/acetonitrile, dichloromethane, preferably dichloromethane, and pyridine and 2-chloro-fluoroaniline were added at room temperature. A suitable coupling agent (carboxylic acid activating agent), e. g. COMU®, propylphosphonic anhydride (T3P®), 2-Bromo-1-ethylpyridinium tetrafluoroborate, 2-Chloro-1-methylpyridinium iodide, preferably COMU® was added, the mixture was heated (30-40° C.), preferably 40° C. and stirred for 1-4 days, preferably 4 days. After cooling the usual work-up was performed and crude (A9) was obtained.

Surprisingly, only a limited set of solvents is suitable for efficiently facilitating both, activation of the carboxylic acid and coupling to 2-chloro-fluoroaniline to form (A9) while avoiding formation of substantial amounts of undesired by-products, as general compatibility of these coupling reagents to a wide range of aprotic solvents is tolerated as known by a skilled person.

Surprisingly, the desired transformation is efficiently facilitated by addition of the amide coupling agent as last component to the reaction mixture of carboxylic acid (A7), 2-chloro-fluoroaniline and base, as generally pre-activation would be preferred by a skilled person, such as the addition of COMU to carboxylic acid (A7) and base, then adding 2-chloro-fluoroaniline.

Surprisingly, within the range of bases tested, only pyridine was found to efficiently promote the desired transformation to (A9). Usually, amide coupling reactions proceed rather fast, within minutes to hours duration at room temperature. In case of the nucleophile 2-chloro-fluoroaniline, extraordinary long reaction times at 40° C. or below promoted the desired reaction, while the reaction at short standard reaction times and under standard conditions did not indicate significant turnover towards product.

Step 9a) (A9) to Compound (I)

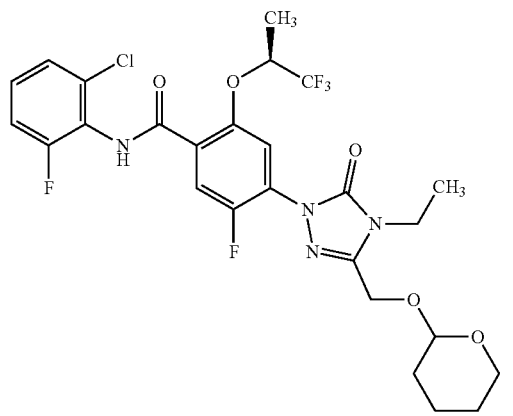

(A9)

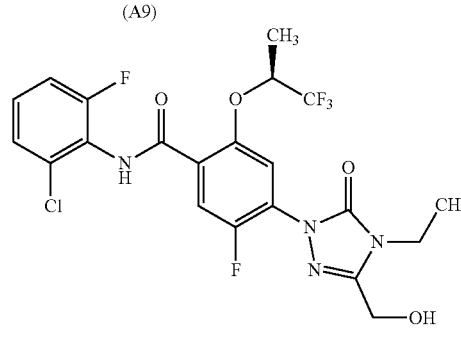

Compound (I)

Method A

Intermediate compound (A9) as obtained in Step 8a) was placed in a polar protic solvent, such as methanol, ethanol, propanol, preferably ethanol, (alternatively (A9) obtained from 8b) can be used), a strong protic acid was added, e. g. toluenesulfonic acid, acetic acid, sulfuric acid, hydrochloric acid, phosphorous acid, preferably 85% phosphorous acid was added and the mixture heated at 50°-60° C., preferably at 57°-60° C. for 1-24 h, more specifically for 16-21 h, preferably over night. The mixture was cooled to room temperature, a strong protic acid such as sulfonic acids, acetic acid, sulfuric acid, phosphoric acid, hydrochloric acid, preferably hydrochloric acid, at any suitable concentration, optionally a non-polar solvent such as diisopropylether was added as well as aqueous sodium chloride. The resulting mixture again was stirred for a short period of time. Usual work-up known by a skilled person was performed. The isolated crude solid was [a] suspended in a suitable solvent such as ethanol, n-butanol, acetone, diisopropyl ether, 2-butanone, preferably 2-butanone, heated to 55°-60° C., preferably to 60° C. and again filtered, the filter cake washed and the combined filtrates evaporated to yield Compound (I).

Optionally, the crude product was [b] further purified by silica gel chromatography with n-heptane/5-50% acetone as eluent. The combined product-containing fractions were evaporated to obtain purified Compound (I).

Step 9b) (A7) to Compound (I)

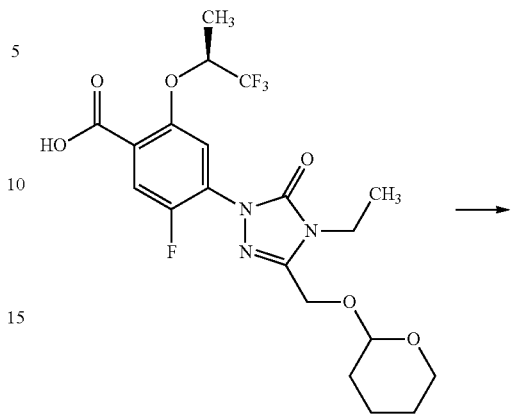

(A7)

[
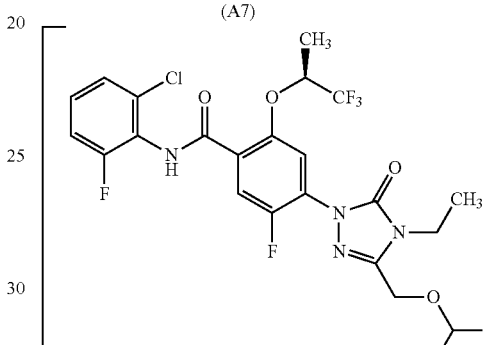

(A9)
]

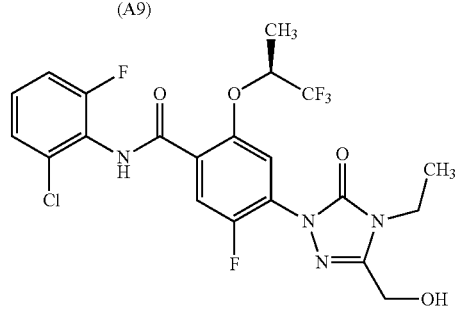

Compound (I)

Method B

Compound (A7) as obtained above from step 7 is suspended in a suitable aprotic solvent such as e. g. acetonitrile, dichloromethane, tetrahydrofuran preferably acetonitrile, and pyridine (3 or more molar equivalents to (A7), preferably 3.5 equivalents) and 2-chloro-6-fluoroaniline (1.2 to 10 molar equivalents to (A7), preferably 1.5 equivalents were added at room temperature. The solution was cooled to 0°-5° C. and phosphoryl chloride (1 or more molar equivalents to (A7), preferably 1.1 equivalents) was added over a short period of time. The reaction mixture was stirred for about 60 min, methanol and 85% phosphoric acid were added and the resulting mixture was heated to about 60° C. and stirred again, that time for about 2 h. Subsequently the solvent was removed, the remaining residue was cooled to room temperature and stirred for about 16 h. The resulting mixture was further cooled to 0°-5° C., stirred for additional 2 h and the solid isolated, optionally washed one or more times and dried. Optionally further purification could be achieved by suspending the solid in anhydrous ethanol, heating to 60° C., filtering, optionally washing the filter cake, combining the filtrates, removing part of the solvent by destillation, cooling the mixture, optionally seeding the the mixture and cooling further to about 0°-5° C. The Compound (I) was obtained as a solid.

- Surprisingly, the desired transformation is only efficiently facilitated by addition of the amide coupling agent to the carboxylic acid (A7) and to 2-chloro-fluoroaniline, as generally pre-activation to the acid chloride (A8) would be preferred by a skilled person to avoid undesired reactions. In this case, this generally preferred order of addition gives inferior results.
- Surprisingly, only the rather exotic amide coupling reagent phosphoryl chloride is suitable for efficiently facilitating both, activation of the carboxylic acid and coupling to 2-chloro-fluoroaniline to form (A9) while avoiding formation of substantial amounts of undesired by-products. For example, the common activating reagents thionyl chloride and oxalyl chloride do promote the desired reaction only to a limited extent (9-16% area of intermediate (A8) by HPLC method 1). Compared to standard amide coupling reagents as exemplified in Step 8b), method B, phosphoryl chloride is more active, cheap and readily available.
- Surprisingly, within the range of bases tested, only pyridine was found to efficiently promote the desired transformation to (A9).
- Surprisingly, only a limited set of solvents is suitable for efficiently facilitating both, activation of the carboxylic acid and coupling to 2-chloro-fluoroaniline to form (A9) while avoiding formation of substantial amounts of undesired by-products
- Direct conversion of the crude THP-protected intermediate (A9) solution was found to be crucial as the THP protection group is labile under a number of aqueous workup conditions, and (A9) could not be efficiently isolated as solid despite very intensive investigation.
- Crude Compound (I) was easily isolated in high yield in a one-pot reaction upon concentration of the reaction mixture, and an aqueous work-up with phase separations is not necessary. Surprisingly, aqueous workup to remove inorganic by-products is not needed. As Compound (I) precipitates from a range of bi-phasic workup mixtures at industrially useful concentrations, avoidance of water use was crucial for design of an efficient production process.
- An unusual high number of experiments had to be conducted for the final crystallization, as solid Compound (I) can be obtained from a range of solvents, but only a very limited set of solvents/conditions is suitable for efficient purging of structurally related process impurities.

Step 10 Micronization

Compound (I) as obtained by method A or method B in step 9a) or 9b) above is micronized.

In one embodiment of the invention the micronization is performed according to the conditions as disclosed in example 9, more specifically according to example 9-1 or 9-2.

One embodiment of the invention provides a process for the preparation of compound (I) as disclosed infra comprising a step where compound (I) is micronized.

One embodiment of the invention is Compound (I) in its micronized form.

A further embodiment of the invention is Compound (I) in its micronized form having a particle size of 0.1 µm-100 µm (X10-X90).

A further embodiment of the invention is Compound (I) in its micronized form having a particle size of 0.3 µm-100 µm (X10-X90).

A further embodiment of the invention is Compound (I) in its micronized form having a particle size of 0.3 µm-20 µm (X10-X90).

A further embodiment of the invention is Compound (I) in its micronized form having a particle size of 0.3 µm-5 µm (X10-X90).

A further embodiment of the invention is Compound (I) in its micronized form having a particle size of 0.6 µm-4 µm (X10-X90).

A further embodiment of the invention is Compound (I) in its micronized form having a particle size of 0.6 µm-3.8 µm (X10-X90).

A further embodiment of the invention is Compound (I) in its micronized form having a particle size of 0.6 µm-3 µm (X10-X90).

THP as hydroxy protecting group shows superior performance throughout the entire process. It supports results well reproducible transformations and allows for solid key intermediates that are easily isolated in high yield and excellent purity.

The choice for THP as hydroxy protecting group was not straightforward to a skilled person. Implementation of this protecting group in the given process required substantial experimentation due to the intrinsic instability under acidic conditions. In particular, partial hydroxy deprotection would be expected to lead to dehydroxy-chlorination upon acid chloride formation, undesirable alkylchloride by-products as process impurities and loss of yield.

Prior to selection of THP, the following protecting groups were considered:

- Benzyl (Bn): works comparable throughout the synthetic route to the final intermediate, but all attempts of deprotection on the final stage failed due to either substantial loss of the chloride upon hydrogenolysis attempts (e.g. Pd/C, $H_2$ or under transfer hydrogenation conditions) or decomposition under strongly acidic conditions.
- tert-Butyl-diphenylsilyl (TBDPS), acetyl (Ac), pivaloyl (Piv) can in principle be employed under the amide coupling conditions and can be deprotected under mild conditions (e.g. potassium carbonate in methanol), but these protecting groups are not stable towards the nucleophilic substitution conditions on earlier steps. In addition, benzoyl (Bz) was considered, but similar issues as for Piv and Ac were anticipated based on model reactions.
- The use of tert-Butyl (t-Bu), tert-Butoxymethyl, Methoxyethoxymethyl (MEM) ethers would in principle lead to more acid-stable intermediates, but synthesis and/or crystallization of these lipophilic intermediates and the much harsher deprotection conditions needed is deemed to be inferior to the current process.

Tetrahydrofuranyl (THF) and 1-Ethoxyethyl (EE) as protecting group with similar reactivity as THP, but slightly higher lability under acidic conditions.

In accordance with a first aspect, the invention provides a method of preparing Compound (I) comprising the step of allowing an intermediate compound of formula (A7):

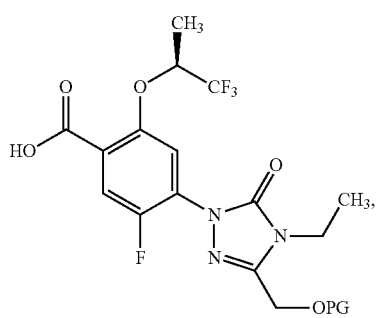

(A7.1)

wherein PG is a protecting group selected from Tetrahydropyranyl (THP), Tetrahydrofuranyl (THF), 1-Ethoxyethyl (EE), tert-Butyl (t-Bu), tert-Butoxymethyl, Methoxyethoxymethyl (MEM).

to react with a compound of formula (xxx7):

(xxx7)

optionally in a suitable aprotic solvent, by addition of a suitable base, optionally under activation of the carboxylic acid group or by generation of an intermediate acid chloride using a suitable reagent, and either adding a reagent for cleaving the protecting group or isolating compound (A9.1)

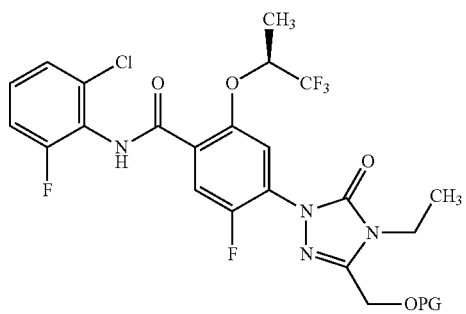

(A9.1)

and subsequently adding a reagent for cleaving the protecting group, thereby providing Compound (I):

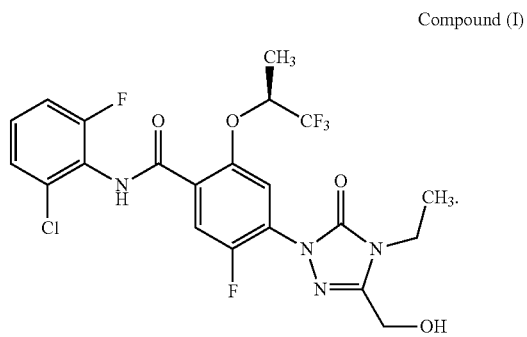 [SMILES: CCn1c(CO)nn(-c2cc(O[C@@H](C)C(F)(F)F)c(C(=O)Nc3c(F)cccc3Cl)cc2F)c1=O]

Compound (I)

In accordance with a second aspect, the invention provides methods of preparing Compound (I) according to Scheme 4 as described supra.

In accordance with an embodiment of the first and the second aspect, the invention provides a method of preparing Compound (I) comprising the step of allowing an intermediate compound of formula (A7):

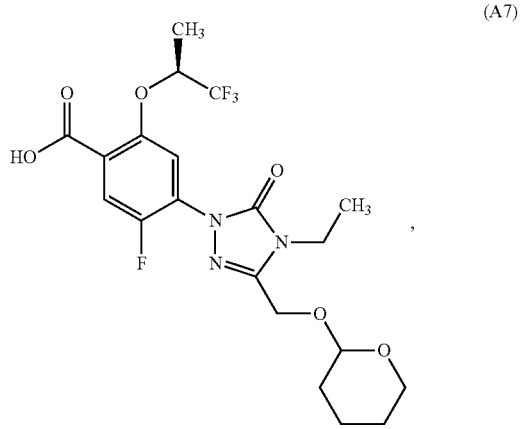 [SMILES: CCn1c(COC2CCCCO2)nn(-c2cc(O[C@@H](C)C(F)(F)F)c(C(=O)O)cc2F)c1=O]

(A7)

to react with a compound of formula (xxx7):

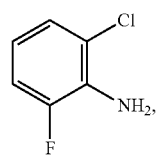

(xxx7)

optionally in a suitable aprotic solvent, such as acetonitrile, by addition of a suitable base, optionally under activation of the carboxylic acid group or by generation of an acid chloride using a suitable reagent, and either adding one or more reagents for cleaving the protecting group or isolating compound (A9)

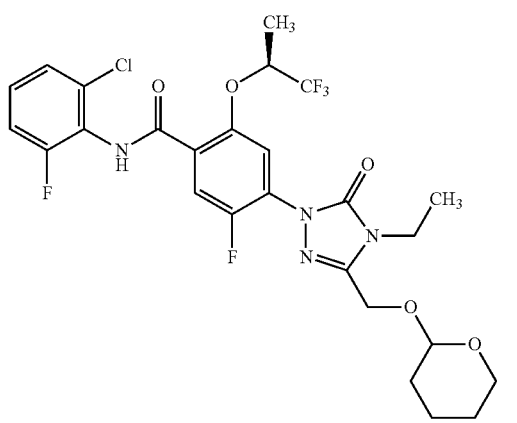

(A9)

and subsequently adding one or more reagents for cleaving the protecting group, thereby providing Compound (I):

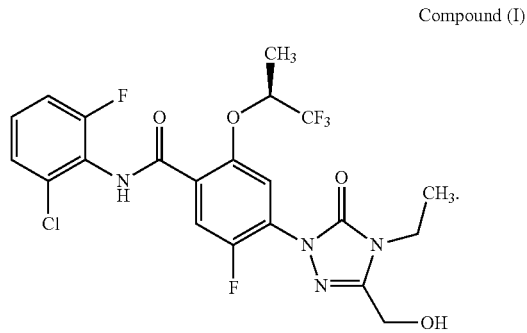 [SMILES: CCn1c(CO)nn(-c2cc(O[C@@H](C)C(F)(F)F)c(C(=O)Nc3c(F)cccc3Cl)cc2F)c1=O]

Compound (I)

In accordance with an embodiment of the first and the second aspect and any embodiment disclosed herein, the invention provides a method of preparing Compound (I) wherein PG is a tetrahydropyranylether and further comprising acidic conditions as reagents for cleaving the protecting group tetrahydropyranylether.

In accordance with an embodiment of the first and the second aspect and any embodiment disclosed herein, the invention provides a method of preparing Compound (I), wherein the acidic conditions for cleaving the THP ether are accomplished by addition of phosphoric acid and an alcohol, e.g. methanol, ethanol or 2-propanol.

In accordance with an embodiment of the first and the second aspect and any embodiment disclosed herein, the invention provides a method of preparing Compound (I), wherein the acidic conditions for cleaving the THP ether are accomplished by addition of phosphoric acid and methanol.

In accordance with an embodiment of the first and the second aspect and any embodiment disclosed herein, the invention provides a method of preparing Compound (I), comprising the step of allowing an intermediate compound of formula (A7) to react with a compound of formula (xxx7) giving a compound of formula (A9) wherein the suitable base is pyridine.

In accordance with an embodiment of the first and the second aspect and any embodiment disclosed herein, the invention provides a method of preparing Compound (I) comprising the step of allowing an intermediate compound of formula (A7) to react with a compound of formula (xxx7) giving a compound of formula (A9), further comprising activation of the carboxylic acid or generation of an acid chloride of formula (A8).

In accordance with an embodiment of the first and the second aspect and any embodiment disclosed herein, the invention provides a method of preparing Compound (I) comprising the step of allowing an intermediate compound of formula (A7) to react with a compound of formula (xxx7) giving a compound of formula (A9), further comprising generation of an acid chloride of formula (A8).

In accordance with an embodiment of the first and the second aspect and any embodiment disclosed herein, the invention provides a method of preparing Compound (I) wherein the reagent for activation of A7 is phosphoryl chloride.

In accordance with an embodiment of the first and the second aspect and any embodiment disclosed herein, the invention provides a method of preparing Compound (I) wherein the acid chloride or an activated acid is generated in situ.

In accordance with an embodiment of the first and the second aspect and any embodiment disclosed herein, the invention provides a method of preparing Compound (I) comprising isolating compound (A9) and subsequently cleaving the protecting group.

In accordance with an embodiment of the first and the second aspect and any embodiment disclosed herein, the invention provides a method of preparing Compound (I) comprising the step of allowing an intermediate compound of formula (A7) to react with a compound of formula (xxx7) giving Compound (I), whereby the reaction is carried out as a one-pot-reaction.

In accordance with an embodiment of the first and the second aspect and any embodiment disclosed herein, the invention provides a method of preparing Compound (I) comprising a one-pot reaction starting from compound (A7)

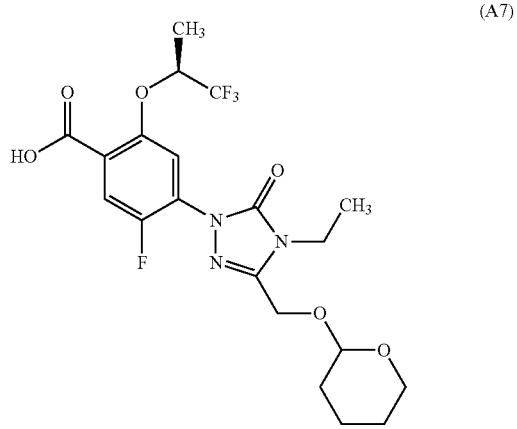 [SMILES: CCn1c(COC2CCCCO2)nn(-c2cc(O[C@@H](C)C(F)(F)F)c(C(=O)O)cc2F)c1=O]

(A7)

Compound (I)

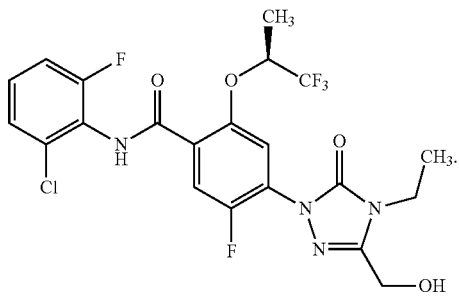

In accordance with an embodiment of the first and the second aspect and any embodiment disclosed herein, the invention provides a method of preparing Compound (I) further comprising a step for isolation of Compound (I).

In accordance with an embodiment of the first and the second aspect and any embodiment disclosed herein, the invention provides a method of preparing Compound (I) further comprising a step for purification of Compound (I).

In accordance with an embodiment of the first and the second aspect and any embodiment disclosed herein, the invention provides a method of preparing Compound (I), further comprising a micronization step.

In accordance with an embodiment of the first and the second aspect and any embodiment disclosed herein, the invention provides a method of preparing Compound (I) further comprising a step for isolation and purification of Compound (I).

In a further embodiment, the invention provides a method of preparing Compound (I), comprising a step of converting a compound of formula (A6)

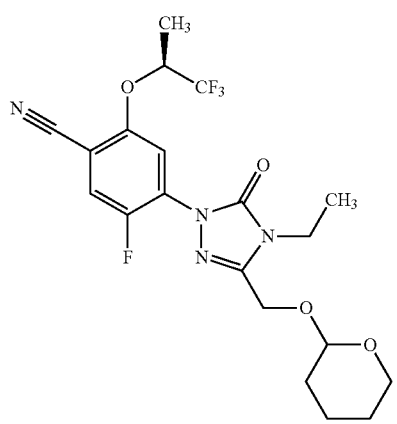

to a compound of formula (A7)

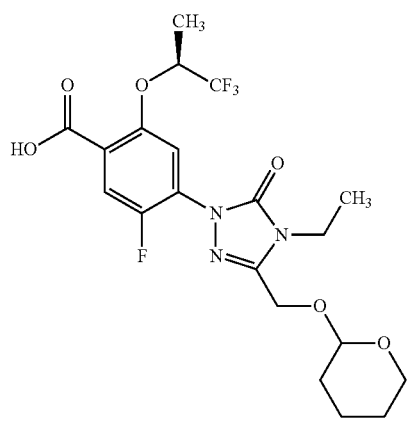

optionally in a polar protic solvent such as an alcohol and by further addition of an aqueous alkaline metal hydroxide or alkaline earth metal hydroxide solution and optionally isolating compound (A7).

In accordance with an embodiment of the first and the second aspect and any embodiment disclosed herein, the invention provides a method of preparing Compound (I), further comprising a step of converting a compound of formula (A6)

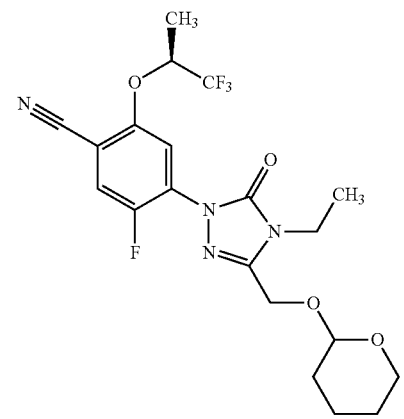

to a compound of formula (A7)

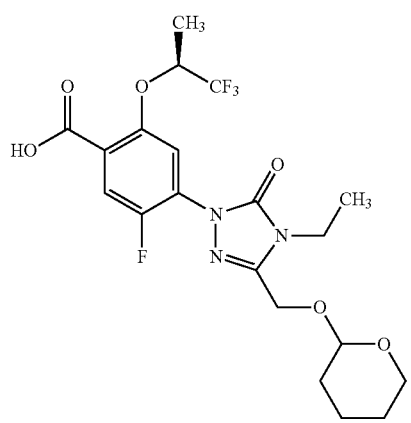

optionally in a polar protic solvent such as an alcohol and by further addition of an aqueous alkaline metal hydroxide or alkaline earth metal hydroxide solution and optionally isolating compound (A7).

In another embodiment, the invention provides a method of preparing Compound (I), comprising a step of reacting a compound (A5)

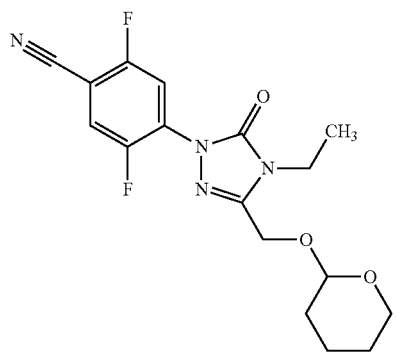

(A5)

with a compound (xxx6)

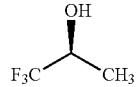

(xxx6)

optionally in a polar aprotic solvent, such as acetonitrile, and by addition of an alkaline metal phosphate, such as potassium phosphate, thereby giving a compound of formula (A6)

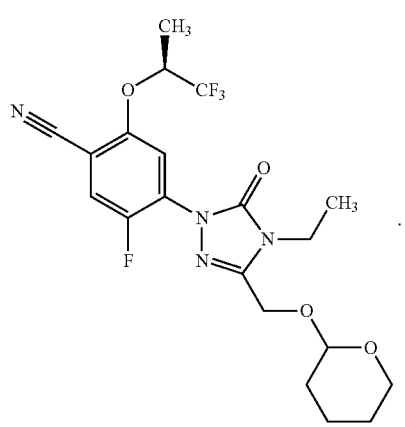

(A6)

In accordance with an embodiment of the first and the second aspect and any embodiment disclosed herein, the invention provides a method of preparing Compound (I), further comprising a step of reacting a compound (A5)

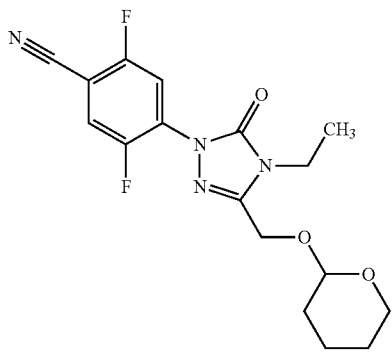

(A5)

with a compound (xxx6)

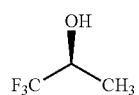

(xxx6)

optionally in a polar aprotic solvent, such as acetonitrile, and by addition of an alkaline metal phosphate, such as potassium phosphate, thereby giving a compound of formula (A6)

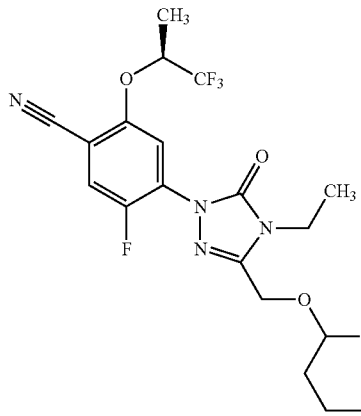

(A6)

In a further embodiment, the invention provides a method of preparing Compound (I), comprising a step of reacting a compound of formula (A4)

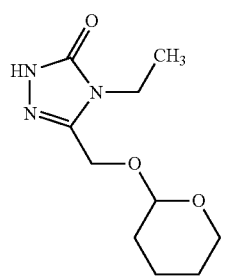

(A4)

optionally in a polar aprotic solvent, such as acetonitrile, with 2,4,5-trifluorobenzonitrile (xxx5)

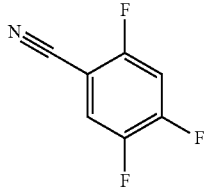
(xxx5)

thereby giving a compound of formula (A5)

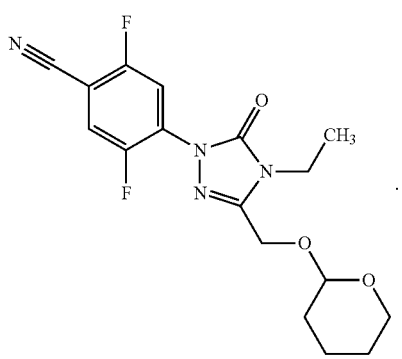
(A5)

In accordance with an embodiment of the first and the second aspect and any embodiment disclosed herein, the invention provides a method of preparing Compound (I), further comprising a step of reacting a compound of formula (A4)

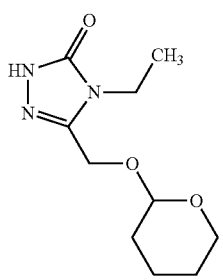
(A4)

optionally in a polar aprotic solvent, such as acetonitrile, with 2,4,5-trifluorobenzonitrile (xxx5)

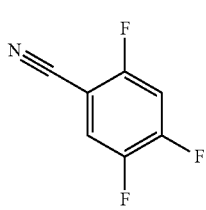
(xxx5)

thereby giving a compound of formula (A5)

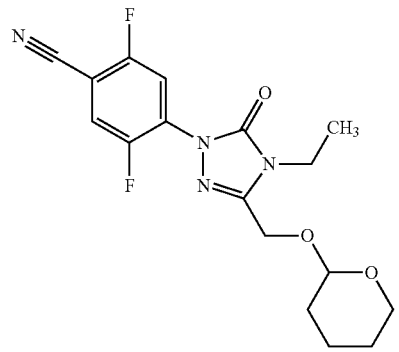
(A5)

In another embodiment, the present invention provides a method of preparing Compound (I), said method comprising the step of allowing an intermediate compound of formula (A7):

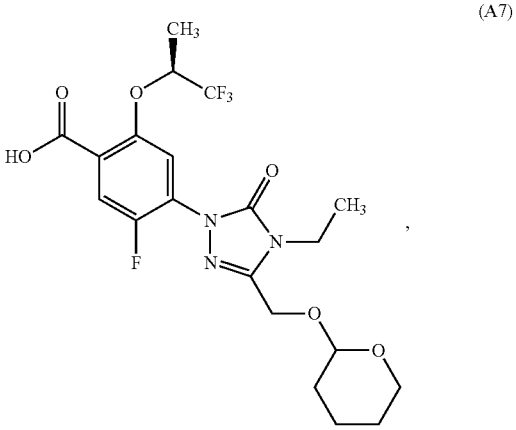 [SMILES: CCn1c(COC2CCCCO2)nn(-c2cc(O[C@@H](C)C(F)(F)F)c(C(=O)O)cc2F)c1=O]
(A7)

to react with a compound of formula (xxx7):

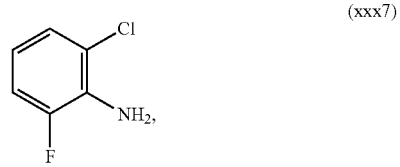
(xxx7)

optionally in a solvent, by addition of a suitable base, optionally under activation of the carboxylic acid group or by generation of an intermediate acid chloride using a suitable reagent, such as e.g. 1-Chloro-N,N,2-trimethyl-1-propenylamine, phosphoryl chloride, optionally isolating said acid chloride, optionally adding one or more reagents for cleaving the protecting group thereby giving Compound (I):

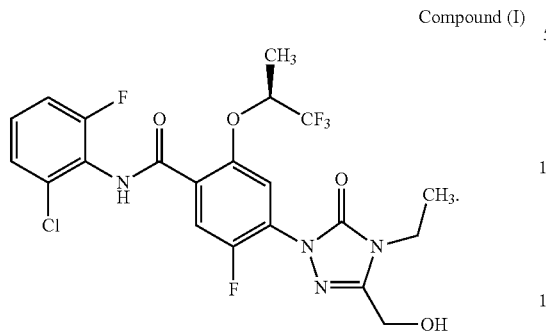

Compound (I)

In accordance with an embodiment of the second aspect, the present invention provides a method of preparing Compound (I), said method comprising the step of allowing an intermediate compound of formula (A7):

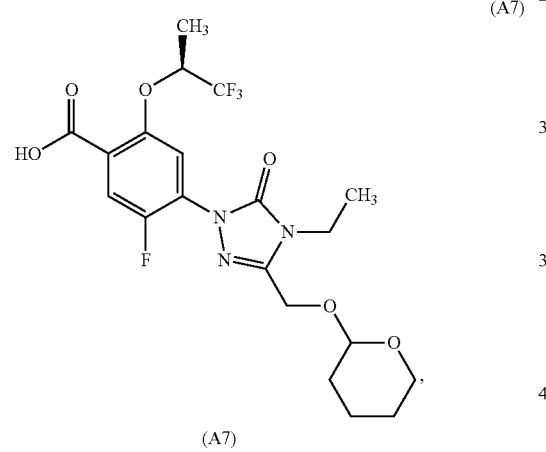

(A7)

to react with a compound of formula (xxx7):

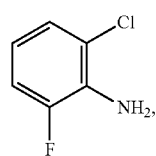

(xxx7)

optionally in a solvent, by addition of a suitable base, optionally under activation of the carboxylic acid group or by generation of an intermediate acid chloride using a suitable reagent, such as e.g. 1-Chloro-N,N,2-trimethyl-1-propenylamine, phosphoryl chloride, optionally isolating said acid chloride, optionally adding one or more reagents for cleaving the protecting group thereby giving Compound (I):

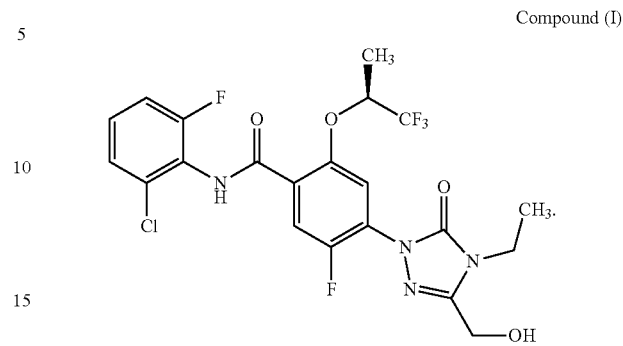

Compound (I)

In accordance with an embodiment of the second aspect, and any embodiments disclosed herein the present invention provides a method of preparing Compound (I), said method comprising the step of allowing an intermediate compound of formula (A7):

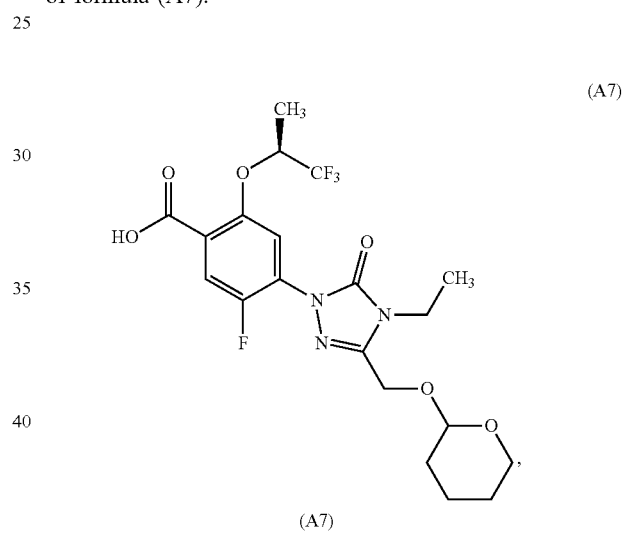

(A7)

to react with a compound of formula (xxx7):

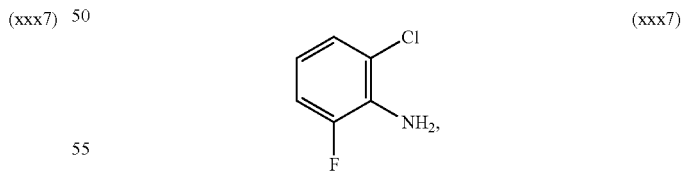

(xxx7)

optionally in a solvent, by addition of a suitable base, optionally under activation of the carboxylic acid group or by generation of an intermediate acid chloride using a suitable reagent, such as e.g. 1-Chloro-N,N,2-trimethyl-1-propenylamine, phosphoryl chloride, optionally isolating said acid chloride, optionally adding one or more reagents for cleaving the protecting group thereby giving Compound (I):

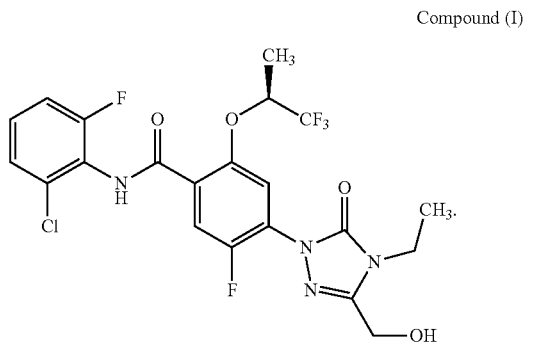 [SMILES: CCn1c(CO)nn(-c2cc(O[C@@H](C)C(F)(F)F)c(C(=O)Nc3c(F)cccc3Cl)cc2F)c1=O]

Compound (I)

It is the current finding that acidic conditions, as disclosed in "Protective Groups in Organic Synthesis" ISBNs: 0-471-16019-9 (Hardback); 0-471-22057-4 (Electronic), pp. 49 as being suitable for cleaving the protecting group THP, may be used for this step.

In another embodiment, the present invention provides a method of preparing Compound (I), said method comprising the step of allowing an intermediate compound of formula (A7):

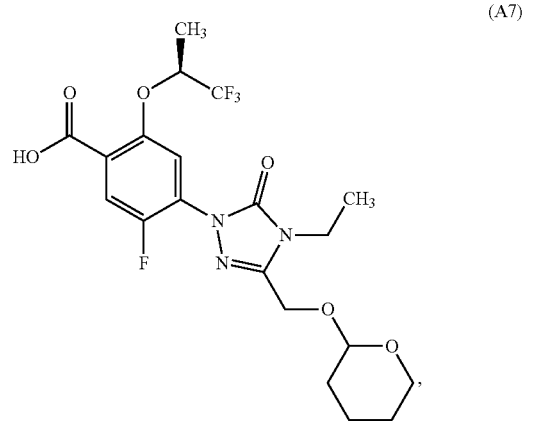 [SMILES: CCn1c(COC2CCCCO2)nn(-c2cc(O[C@@H](C)C(F)(F)F)c(C(=O)O)cc2F)c1=O ; ","]

(A7)

to react with a compound of formula (xxx7):

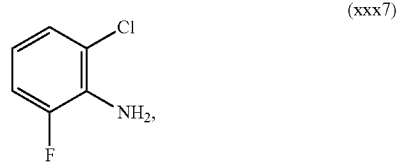

(xxx7)

optionally in a solvent, by addition of a suitable base, optionally under activation of the carboxylic acid group or by generation of an intermediate acid chloride using a suitable reagent such as e.g. COMU, 1-Chloro-N,N,2-trimethyl-1-propenylamine, phosphoryl chloride, optionally isolating said acid chloride, optionally adding one or more reagents for cleaving the protecting group thereby giving Compound (I):

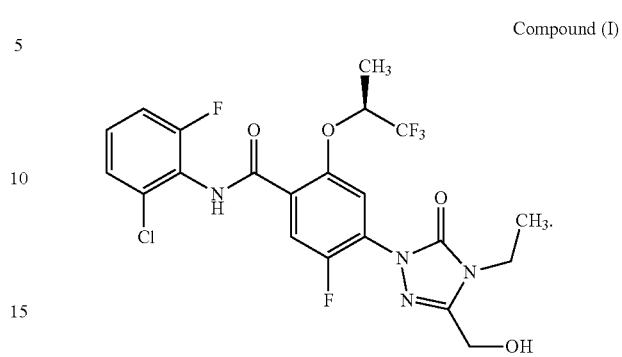

Compound (I)

In accordance with an embodiment of the first or the second aspect, the present invention provides a method of preparing Compound (I), said method comprising the step of allowing an intermediate compound of formula (A7):

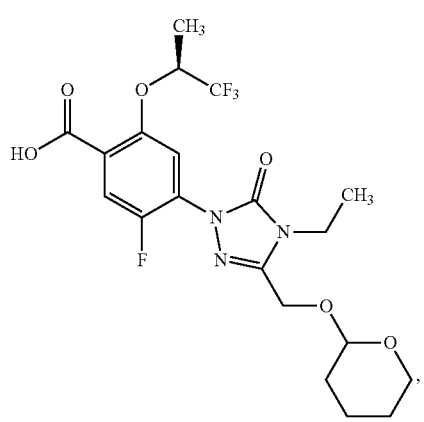

(A7)

to react with a compound of formula (xxx7):

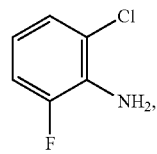

(xxx7)

optionally in a solvent, by addition of a suitable base, optionally under activation of the carboxylic acid group or by generation of an intermediate acid chloride using a suitable reagent such as e.g. COMU, 1-Chloro-N,N,2-trimethyl-1-propenylamine, phosphoryl chloride, optionally isolating said acid chloride, optionally adding one or more reagents for cleaving the protecting group thereby giving Compound (I):

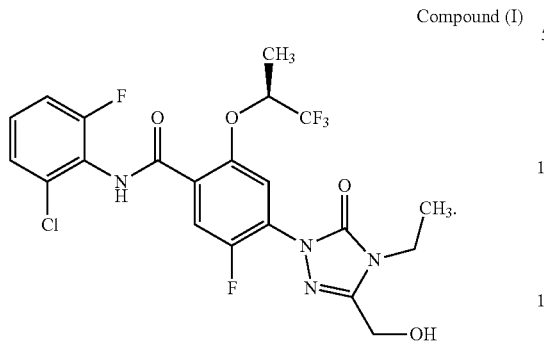

Compound (I)

In accordance with an embodiment of the first or the second aspect, and any embodiment disclosed herein the present invention provides a method of preparing Compound (I), said method comprising the step of allowing an intermediate compound of formula (A7):

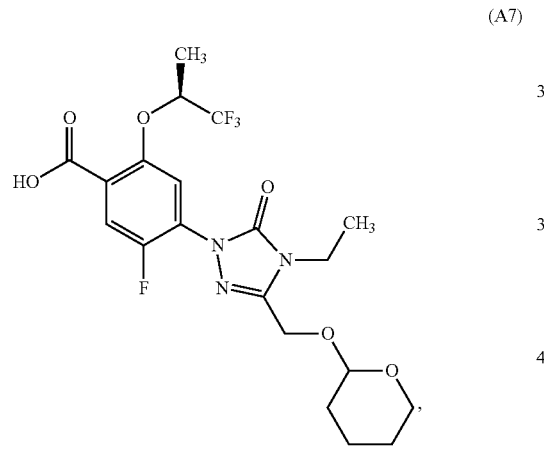

(A7)

to react with a compound of formula (xxx7):

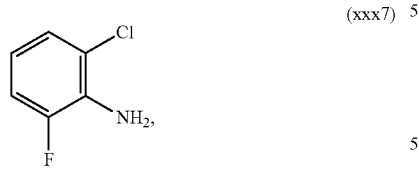

(xxx7)

optionally in a solvent, by addition of a suitable base, optionally under activation of the carboxylic acid group or by generation of an intermediate acid chloride using a suitable reagent such as e.g. COMU, 1-Chloro-N,N,2-trimethyl-1-propenylamine, phosphoryl chloride, optionally isolating said acid chloride, optionally adding one or more reagents for cleaving the protecting group thereby giving Compound (I):

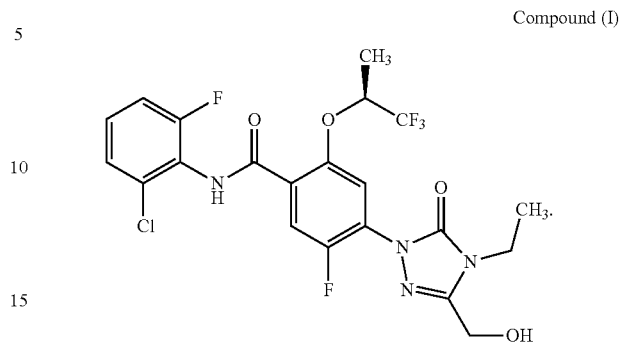

Compound (I)

In a further embodiment, the present invention provides a method of preparing Compound (I) as defined supra, said method comprising the step of allowing an intermediate compound of formula (A7):

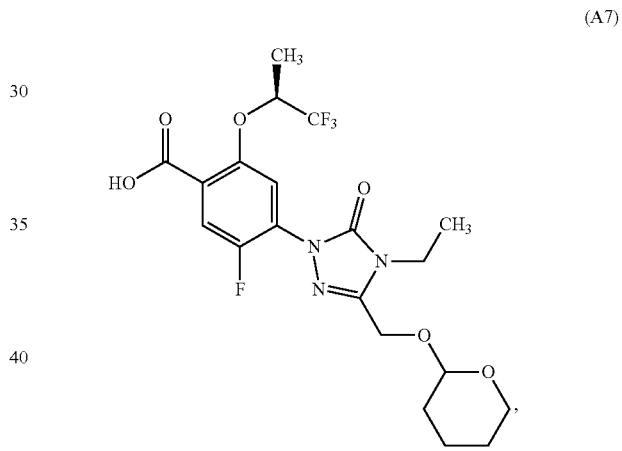

(A7)

to react with a compound of formula (xxx7):

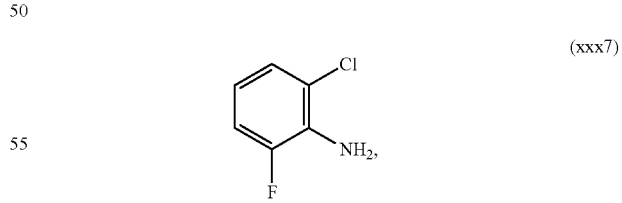

(xxx7)

optionally in a solvent, by addition of a suitable base, optionally under activation of the carboxylic acid group or by generation of an intermediate acid chloride using a suitable agent, such as e.g. 1-Chloro-N,N,2-trimethyl-1-propenylamine, phosphoryl chloride, optionally isolating said acid chloride, optionally isolating compound (A9), thereby giving Compound (I):

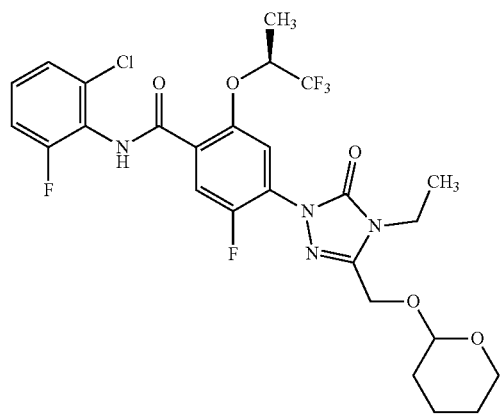
(A9)

and optionally adding one or more reagents for cleaving the protecting group under acidic conditions, e.g. by addition of a strong protic acid, such as e.g. sulfonic acids, acetic acid, sulfuric acid, phosphoric acid, hydrochloric acid, preferably hydrochloric acid, thereby providing Compound (I):

In accordance with an embodiment of the first or the second aspect, the present invention provides a method of preparing Compound (I) as defined supra, said method comprising the step of allowing an intermediate compound of formula (A7)

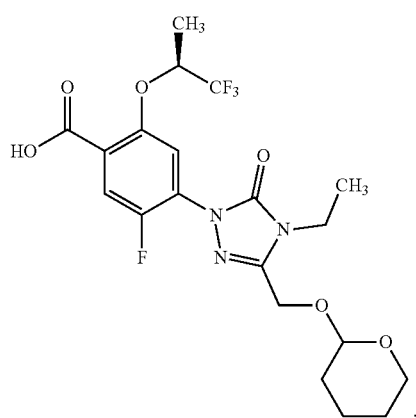
(A7)

to react with a compound of formula (xxx7):

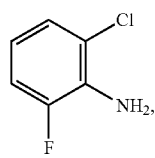
(xxx7)

optionally in a solvent, by addition of a suitable base, optionally under activation of the carboxylic acid group or by generation of an intermediate acid chloride using a suitable agent, such as e.g. 1-Chloro-N,N,2-trimethyl-1-propenylamine, phosphoryl chloride, optionally isolating said acid chloride, optionally isolating compound (A9),

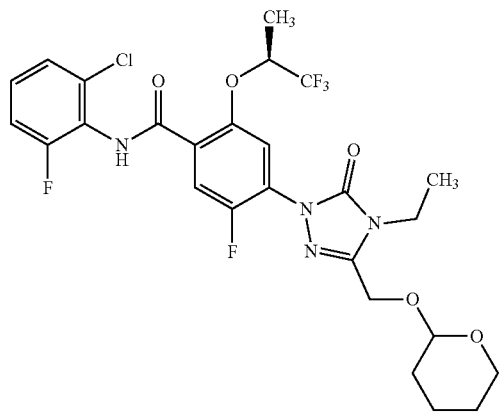
(A9)

and optionally adding one or more reagents for cleaving the protecting group under acidic conditions, e.g. by addition of a strong protic acid, such as e.g. sulfonic acids, acetic acid, sulfuric acid, phosphoric acid, hydrochloric acid, preferably hydrochloric acid, thereby providing Compound (I):

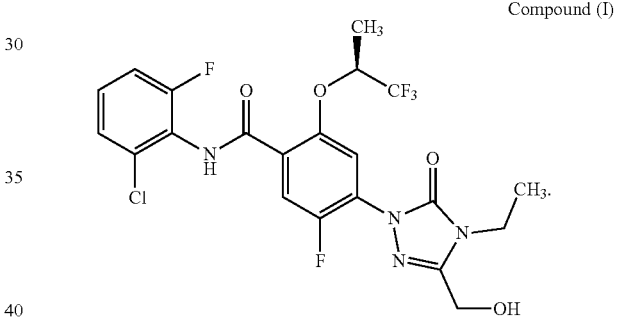
Compound (I)

In accordance with an embodiment of the first or the second aspect and any embodiment disclosed herein, the present invention provides a method of preparing Compound (I) as defined supra, said method comprising the step of allowing an intermediate compound of formula (A7):

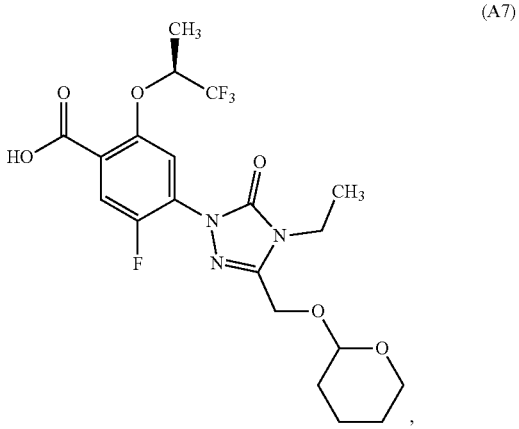 [SMILES: CCn1c(COC2CCCCO2)nn(-c2cc(O[C@@H](C)C(F)(F)F)c(C(=O)O)cc2F)c1=O]
(A7)

to react with a compound of formula (xxx7):

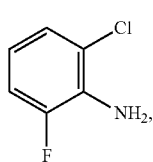
(xxx7)

optionally in a solvent, by addition of a suitable base, optionally under activation of the carboxylic acid group or by generation of an intermediate acid chloride using a suitable agent, such as e.g. 1-Chloro-N,N,2-trimethyl-1-propenylamine, phosphoryl chloride, optionally isolating said acid chloride, optionally isolating compound (A9),

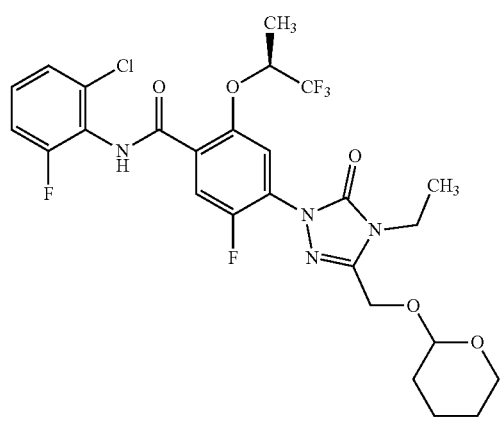
(A9)

and optionally adding one or more reagents for cleaving the protecting group under acidic conditions, e.g. by addition of a strong protic acid, such as e.g. sulfonic acids, acetic acid, sulfuric acid, phosphoric acid, hydrochloric acid, preferably hydrochloric acid,
thereby providing Compound (I):

In another embodiment, the present invention provides a method of preparing Compound (I) as defined supra, said method comprising the step of allowing an intermediate compound of formula (A7):

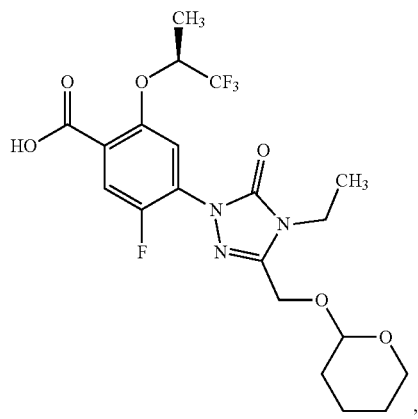
(A7)

to react with a compound of formula (xxx7):

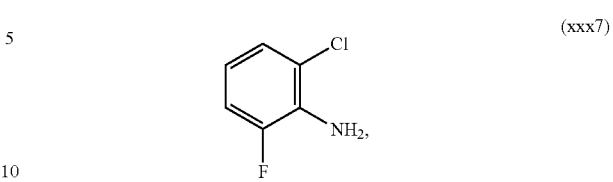
(xxx7)

optionally in a solvent, by addition of a suitable base, optionally under activation of the carboxylic acid group or generation of an intermediate acid chloride using a suitable agent, such as e.g. 1-Chloro-N,N,2-trimethyl-1-propenylamine, phosphoryl chloride, optionally isolating said acid chloride, optionally adding one or more reagents for cleaving the protecting group under acidic conditions, e.g. by addition of a strong protic acid, such as phosphoric acid, thereby providing Compound (I):

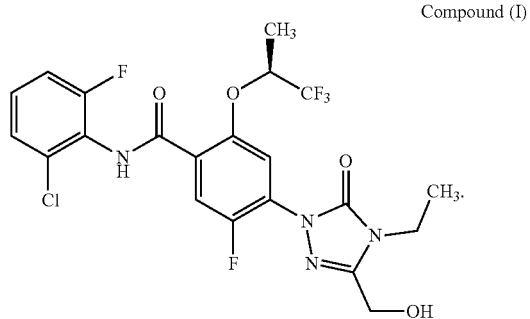 [SMILES: CCn1c(CO)nn(-c2cc(O[C@@H](C)C(F)(F)F)c(C(=O)Nc3c(F)cccc3Cl)cc2F)c1=O]
Compound (I)

In accordance with an embodiment of the first or the second aspect, the present invention provides a method of preparing Compound (I) as defined supra, said method comprising the step of allowing an intermediate compound of formula (A7)

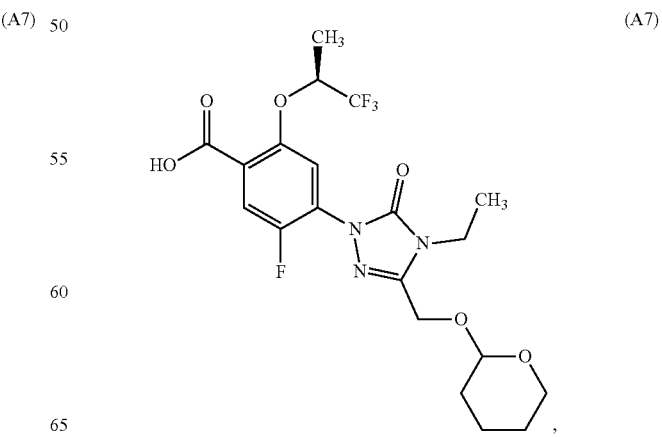
(A7)

to react with a compound of formula (xxx7):

(xxx7)

optionally in a solvent, by addition of a suitable base, optionally under activation of the carboxylic acid group or generation of an intermediate acid chloride using a suitable agent, such as e.g. 1-Chloro-N,N,2-trimethyl-1-propenylamine, phosphoryl chloride, optionally isolating said acid chloride, optionally adding one or more reagents for cleaving the protecting group under acidic conditions, e.g. by addition of a strong protic acid, such as phosphoric acid, thereby providing Compound (I):

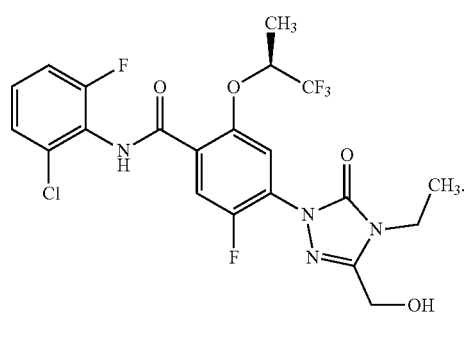
Compound (I)

In accordance with an embodiment of the first or the second aspect and any other embodiment disclosed herein, the present invention provides a method of preparing Compound (I) as defined supra, said method comprising the step of allowing an intermediate compound of formula (A7):

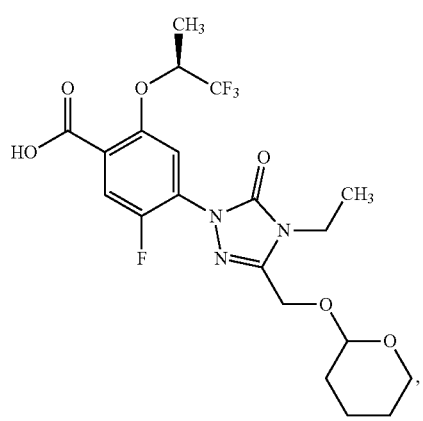
(A7)

to react with a compound of formula (xxx7):

(xxx7)

optionally in a solvent, by addition of a suitable base, optionally under activation of the carboxylic acid group or generation of an intermediate acid chloride using a suitable agent, such as e.g. 1-Chloro-N,N,2-trimethyl-1-propenylamine, phosphoryl chloride, optionally isolating said acid chloride, optionally adding one or more reagents for cleaving the protecting group under acidic conditions, e.g. by addition of a strong protic acid, such as phosphoric acid, thereby providing Compound (I):

In a further embodiment, the present invention provides a method of preparing Compound (I) as defined supra, said method comprising the step of allowing an intermediate compound of formula (A7):

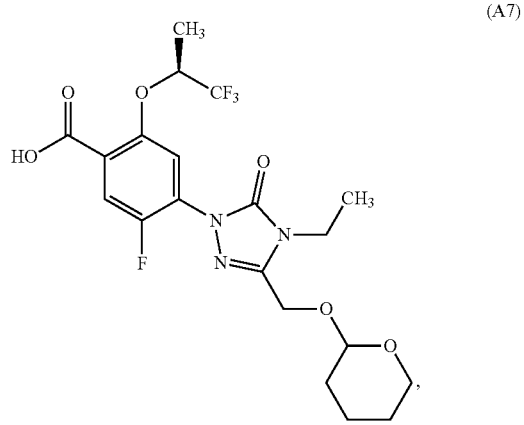
(A7)

to react with a compound of formula (xxx7):

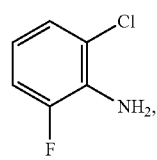
(xxx7)

optionally in a solvent, by addition of a suitable base, optionally under activation of the carboxylic acid group or generation of an intermediate acid chloride using a suitable agent, such as e.g. 1-Chloro-N,N,2-trimethyl-1-propenylamine, phosphoryl chloride, optionally adding one or more reagents for cleaving the protecting group under acidic conditions, e.g. by addition of a strong protic acid, such as phosphoric acid, thereby providing Compound (I):

Compound (I)

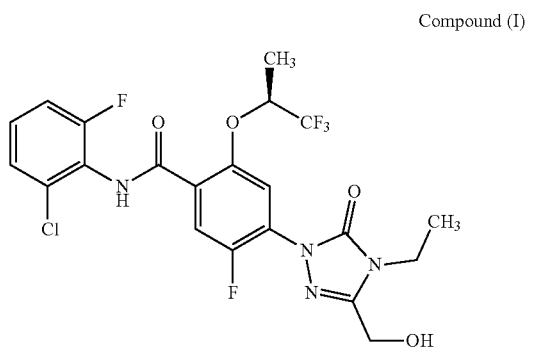 [SMILES: CCn1c(CO)nn(-c2cc(O[C@@H](C)C(F)(F)F)c(C(=O)Nc3c(F)cccc3Cl)cc2F)c1=O]

optionally further comprising one or more purification steps selected from e.g. chromatography, crystallization, recrystallization.

In accordance with an embodiment of the first or the second aspect, the present invention provides a method of preparing Compound (I) as defined supra, said method comprising the step of allowing an intermediate compound of formula (A7):

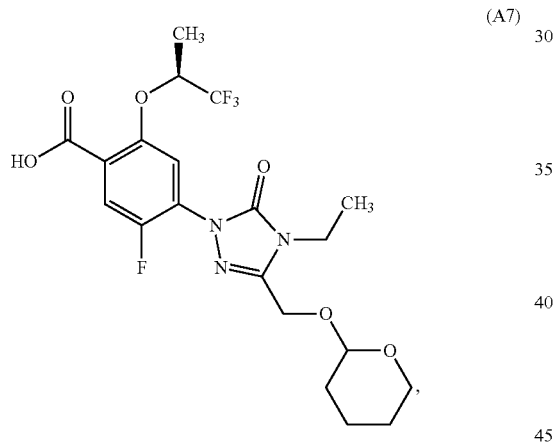

to react with a compound of formula (xxx7):

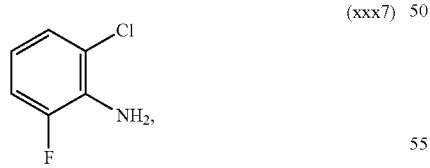

optionally in a solvent, by addition of a suitable base, optionally under activation of the carboxylic acid group or generation of an intermediate acid chloride using a suitable agent, such as e.g. 1-Chloro-N,N,2-trimethyl-1-propenylamine, phosphoryl chloride, optionally adding one or more reagents for cleaving the protecting group under acidic conditions, e.g. by addition of a strong protic acid, such as phosphoric acid, thereby providing Compound (I):

optionally further comprising one or more purification steps selected from e.g. chromatography, crystallization, recrystallization.

In accordance with an embodiment of the first or the second aspect and any embodiments disclosed herein, the present invention provides a method of preparing Compound (I) as defined supra, said method comprising the step of allowing an intermediate compound of formula (A7):

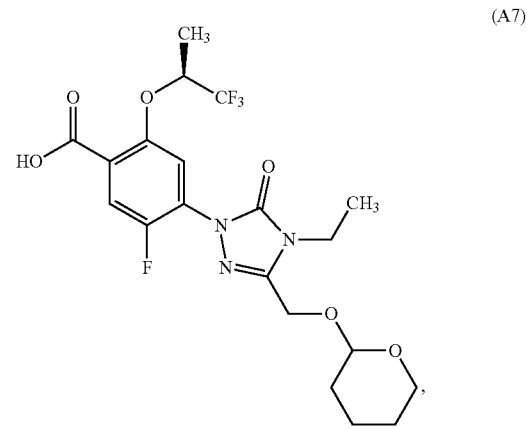

to react with a compound of formula (xxx7):

optionally in a solvent, by addition of a suitable base, optionally under activation of the carboxylic acid group or generation of an intermediate acid chloride using a suitable agent, such as e.g. 1-Chloro-N,N,2-trimethyl-1-propenylamine, phosphoryl chloride, optionally adding one or more reagents for cleaving the protecting group under acidic conditions, e.g. by addition of a strong protic acid, such as phosphoric acid, thereby providing Compound (I):

Compound (I)

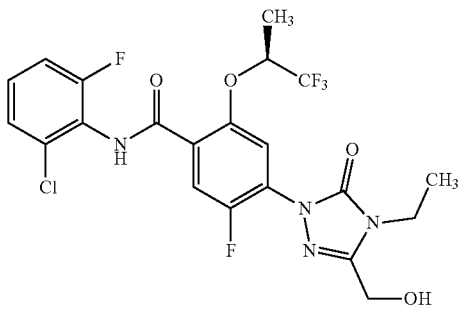

optionally further comprising one or more purification steps selected from e.g. chromatography, crystallization, recrystallization.

In another embodiment, the present invention provides a method of preparing Compound (I) said method comprising the step of allowing an intermediate compound of formula (A7):

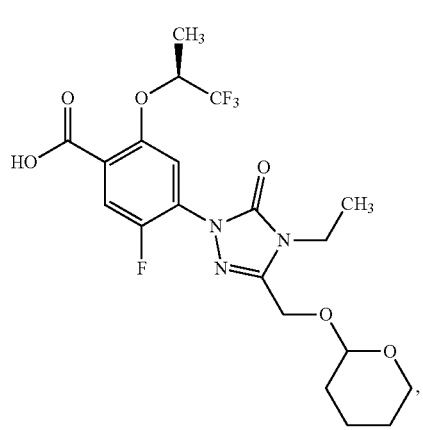
(A7)

to react with a compound of formula (xxx7):

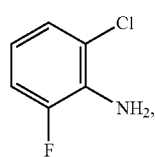
(xxx7)

optionally in a solvent, by addition of a suitable base, optionally under activation of the carboxylic acid group or by generation of an intermediate acid chloride using a suitable agent, such as e.g. 1-Chloro-N,N,2-trimethyl-1-propenylamine, phosphoryl chloride, optionally isolating said acid chloride, optionally adding one or more reagents for cleaving the protecting group under acidic conditions, e.g. by addition of an an organic acid, more specifically by addition of phosphoric acid, thereby providing Compound (I):

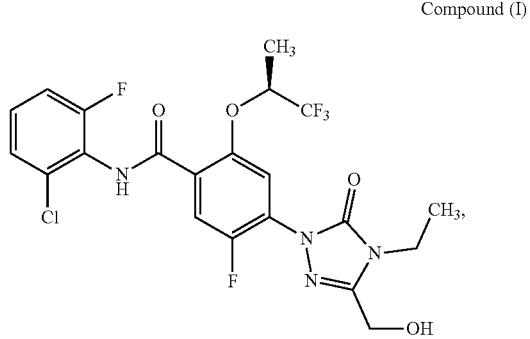 [SMILES: CCn1c(CO)nn(-c2cc(O[C@@H](C)C(F)(F)F)c(C(=O)Nc3c(F)cccc3Cl)cc2F)c1=O]
Compound (I)

then optionally converting said Compound (I) into, an N-oxide or salt or a salt of an N-oxide using the corresponding (i) solvents and/or (ii) bases or acids and optionally further comprising one or more purification steps selected from e.g. crystallization, recrystallization, chromatography.

In accordance with an embodiment of the first or the second aspect, the present invention provides a method of preparing Compound (I) said method comprising the step of allowing an intermediate compound of formula (A7):

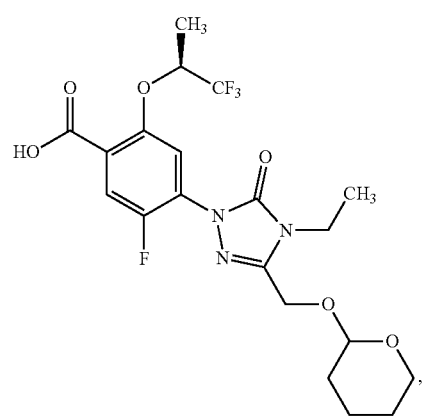
(A7)

to react with a compound of formula (xxx7):

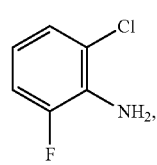
(xxx7)

optionally in a solvent, by addition of a suitable base, optionally under activation of the carboxylic acid group or by generation of an intermediate acid chloride using a suitable agent, such as e.g. 1-Chloro-N,N,2-trimethyl-1-propenylamine, phosphoryl chloride, optionally isolating said acid chloride, optionally adding one or more reagents for cleaving the protecting group under acidic conditions, e.g. by addition of an an organic acid, more specifically by addition of phosphoric acid, thereby providing Compound (I):

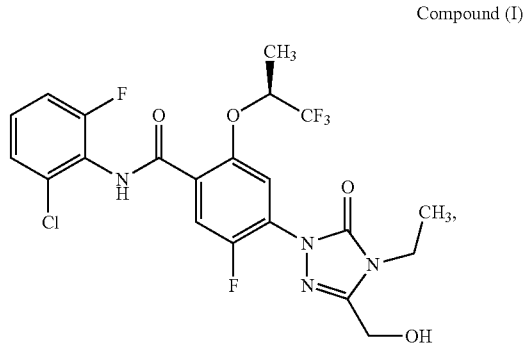 [SMILES: CCn1c(CO)nn(-c2cc(O[C@@H](C)C(F)(F)F)c(C(=O)Nc3c(F)cccc3Cl)cc2F)c1=O]

Compound (I)

then optionally converting said Compound (I) into, an N-oxide or salt or a salt of an N-oxide using the corresponding (i) solvents and/or (ii) bases or acids and optionally further comprising one or more purification steps selected from e.g. crystallization, recrystallization, chromatography.

In accordance with an embodiment of the first or the second aspect and any embodiments disclosed herein, the present invention provides a method of preparing Compound (I) said method comprising the step of allowing an intermediate compound of formula (A7):

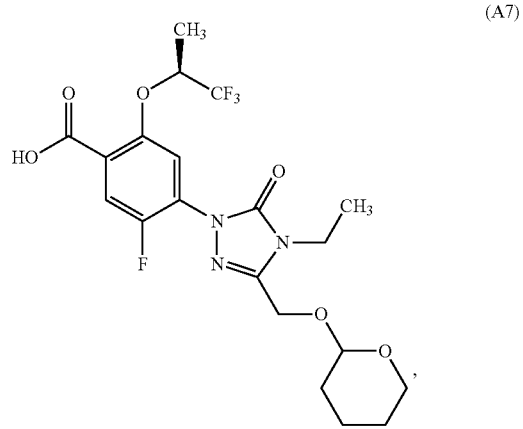 [SMILES: CCn1c(COC2CCCCO2)nn(-c2cc(O[C@@H](C)C(F)(F)F)c(C(=O)O)cc2F)c1=O]

(A7)

to react with a compound of formula (xxx7):

(xxx7)

optionally in a solvent, by addition of a suitable base, optionally under activation of the carboxylic acid group or by generation of an intermediate acid chloride using a suitable agent, such as e.g. 1-Chloro-N,N,2-trimethyl-1-propenylamine, phosphoryl chloride, optionally isolating said acid chloride, optionally adding one or more reagents for cleaving the protecting group under acidic conditions, e.g. by addition of an an organic acid, more specifically by addition of phosphoric acid, thereby providing Compound (I):

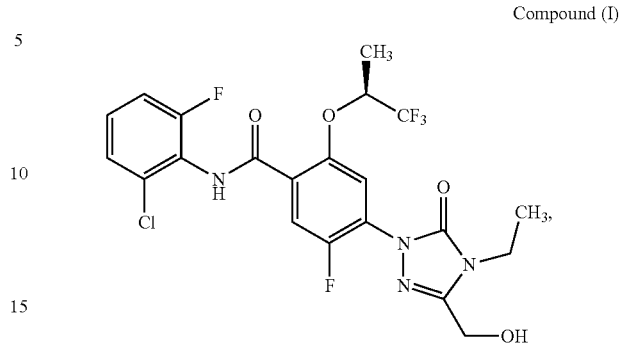

Compound (I)

then optionally converting said Compound (I) into, an N-oxide or salt or a salt of an N-oxide using the corresponding (i) solvents and/or (ii) bases or acids and optionally further comprising one or more purification steps selected from e.g. crystallization, recrystallization, chromatography.

In another embodiment, the present invention provides a method of preparing Compound (I) said method comprising the step of converting said Compound (I) into, an N-oxide or salt or a salt of an N-oxide using the corresponding (i) solvents and/or (ii) bases or acids In another embodiment, the present invention provides a method of preparing Compound (I) said method comprising the step of converting said Compound (I) into a salt using the corresponding (i) solvents and/or (ii) bases or acids Compound (I) can be converted to any salt, preferably pharmaceutically acceptable salt, as described herein, by any method which is known to the person skilled in the art. Similarly, any salt of a Compound (I) can be converted into the free compound, by any method which is known to the person skilled in the art.

Further, it is possible Compound (I) to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

A suitable pharmaceutically acceptable salt of Compound (I) may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthaline disulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of Compound (I) which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for an acid addition salt of Compound (I) to be prepared by reaction of Compound (I) with the appropriate inorganic or organic acid via any of a number of known methods. Alternatively, alkali and alkaline earth metal salts of an acidic part of Compound (I) may be prepared by reacting Compound (I) with the appropriate base via a variety of known methods.

The present invention includes all possible salts Compounds (I) as single salt, or as any mixture of said salts, in any ratio.

In another embodiment, the present invention provides a method of preparing Compound (I) as defined supra, said method comprising the step of allowing an intermediate compound of formula (A7):

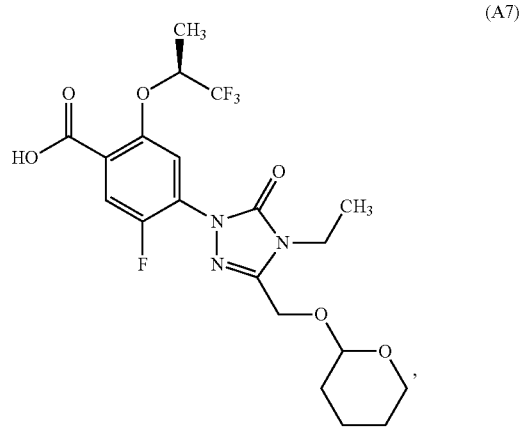 [SMILES: CCn1c(COC2CCCCO2)nn(-c2cc(O[C@@H](C)C(F)(F)F)c(C(=O)O)cc2F)c1=O]

(A7)

to react with a compound of formula (xxx7):

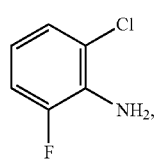

(xxx7)

optionally in a solvent, by addition of a suitable base, optionally under activation of the carboxylic acid group or generation of an intermediate acid chloride using a suitable agent, such as e.g. 1-chloro-N,N,2-trimethyl-1-propenylamine, phosphoryl chloride, optionally isolating said acid chloride, and adding one or more reagents for cleaving the protecting group under acidic conditions, e.g. by addition of a strong protic acid, more specifically by addition of phosphoric acid, thereby giving Compound (I):

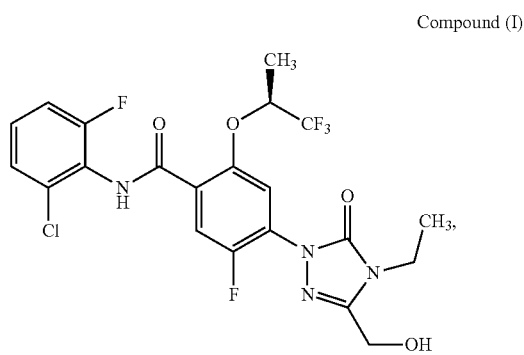 [SMILES: CCn1c(CO)nn(-c2cc(O[C@@H](C)C(F)(F)F)c(C(=O)Nc3c(F)cccc3Cl)cc2F)c1=O]

Compound (I)

then optionally converting said Compound (I) into, an N-oxide or salt or a salt of an N-oxide using the corresponding (i) solvents and/or (ii) bases or acids and optionally further comprising one or more purification steps selected from e.g., crystallization, recrystallization and chromatography and optionally micronizing the product obtained.

In accordance with an embodiment of the first or the second aspect, the present invention provides a method of preparing Compound (I) as defined supra, said method comprising the step of allowing an intermediate compound of formula (A7)

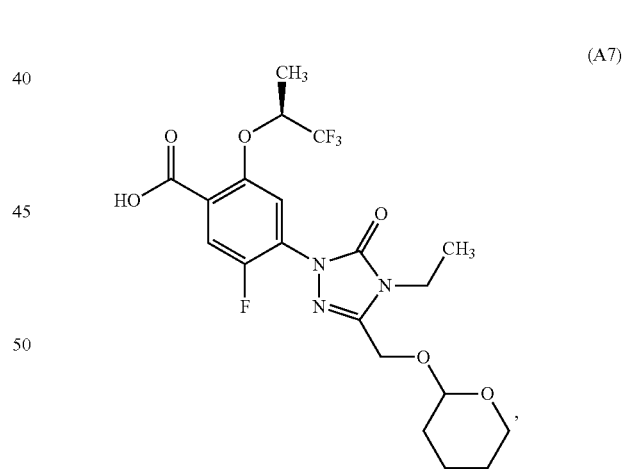

(A7)

to react with a compound of formula (xxx7):

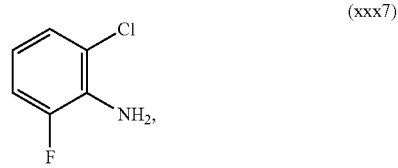

(xxx7)

optionally in a solvent, by addition of a suitable base, optionally under activation of the carboxylic acid group or generation of an intermediate acid chloride using a suitable agent, such as e.g. 1-chloro-N,N,2-trimethyl-1-propenylamine, phosphoryl chloride, optionally isolating said acid chloride, and adding one or more reagents for cleaving the protecting group under acidic conditions, e.g. by addition of a strong protic acid, more specifically by addition of phosphoric acid, thereby giving Compound (I):

Compound (I)

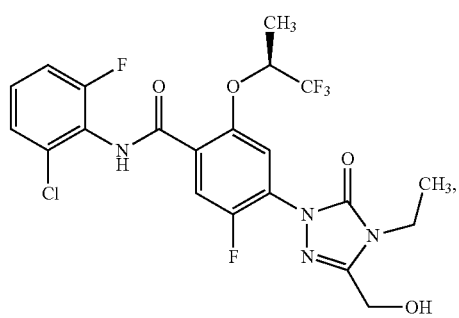

then optionally converting said Compound (I) into, an N-oxide or salt or a salt of an N-oxide using the corresponding (i) solvents and/or (ii) bases or acids and optionally further comprising one or more purification steps selected from e.g., crystallization, recrystallization and chromatography and optionally micronizing the product obtained.

In accordance with an embodiment of the first or the second aspect and any embodiments disclosed herein, the present invention provides a method of preparing Compound (I) as defined supra, said method comprising the step of allowing an intermediate compound of formula (A7):

(A7)

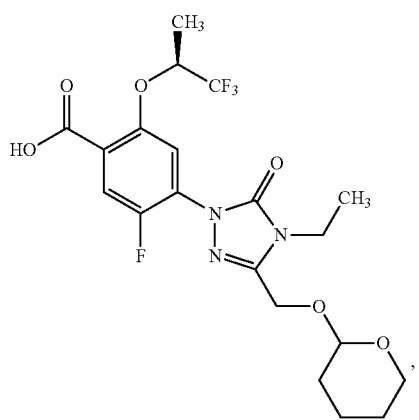

to react with a compound of formula (xxx7):

(xxx7)

optionally in a solvent, by addition of a suitable base, optionally under activation of the carboxylic acid group or generation of an intermediate acid chloride using a suitable agent, such as e.g. 1-chloro-N,N,2-trimethyl-1-propenylamine, phosphoryl chloride, optionally isolating said acid chloride, and adding one or more reagents for cleaving the protecting group under acidic conditions, e.g. by addition of a strong protic acid, more specifically by addition of phosphoric acid, thereby giving Compound (I):

Compound (I)

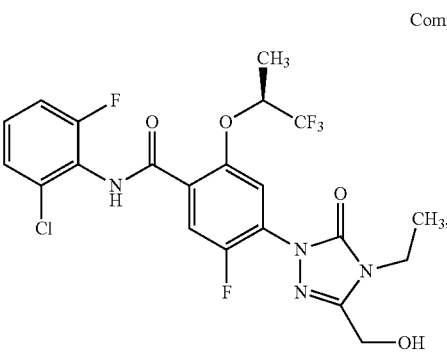

then optionally converting said Compound (I) into, an N-oxide or salt or a salt of an N-oxide using the corresponding (i) solvents and/or (ii) bases or acids and optionally further comprising one or more purification steps selected from e.g., crystallization, recrystallization and chromatography and optionally micronizing the product obtained.

In another embodiment, the present invention provides a method of preparing Compound (I) as defined infra, said method comprising the step of micronizing Compound (I).

In one embodiment of the first or the second aspects as mentioned herein the suitable base is pyridine.

In a further embodiment, the present invention provides a method of preparing Compound (I) as defined supra, said method comprising the step of allowing an intermediate compound of formula (A7):

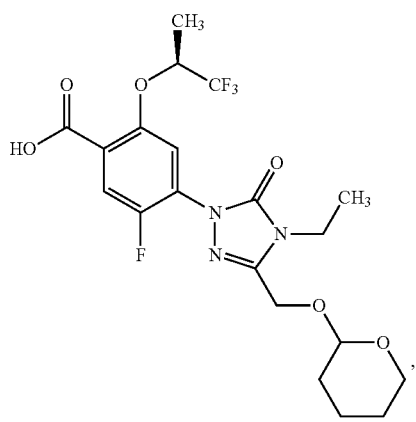

(A7)

to react with a compound of formula (xxx7):

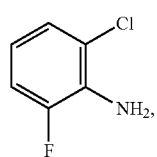

(xxx7)

in CH₃CN, by addition of pyridine, and phosphoryl chloride and cleavage of the protecting group under acidic conditions by using phosphoric acid in an alcohol, e.g. methanol, ethanol, or 2-propanol, preferably methanol, thereby giving Compound (I):

Compound (I)

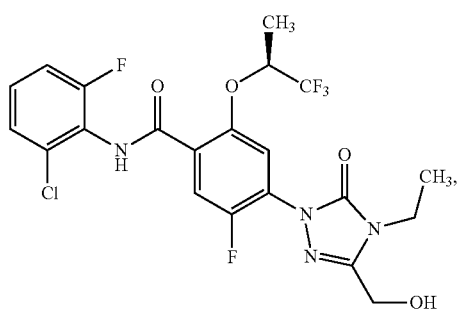

and optionally further comprising one or more purification steps selected from crystallization and recrystallization and optionally micronizing the product obtained.

In accordance with an embodiment of first or the second the second aspect, the present invention provides a method of preparing Compound (I) as defined supra, said method comprising the step of allowing an intermediate compound of formula (A7):

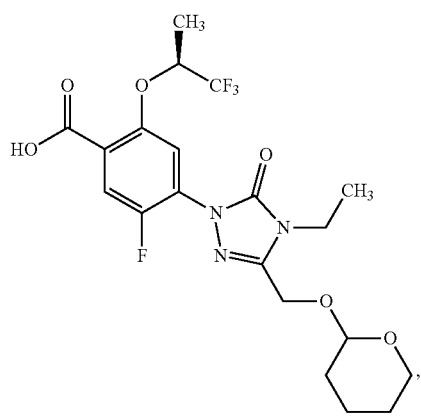

(A7)

to react with a compound of formula (xxx7):

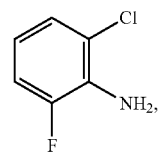

(xxx7)

in CH₃CN, by addition of pyridine, and phosphoryl chloride and cleavage of the protecting group under acidic conditions by using phosphoric acid in an alcohol, e.g. methanol, ethanol, or 2-propanol, preferably methanol, thereby giving Compound (I):

Compound (I)

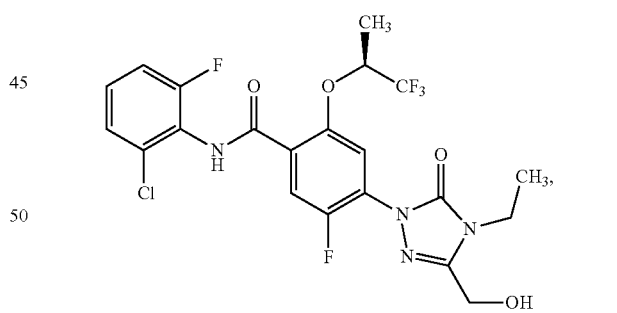

and optionally further comprising one or more purification steps selected from crystallization and recrystallization and optionally micronizing the product obtained.

In accordance with an embodiment of first or the second the second aspect and any embodiments disclosed herein, the present invention provides a method of preparing Compound (I) as defined supra, said method comprising the step of allowing an intermediate compound of formula (A7):

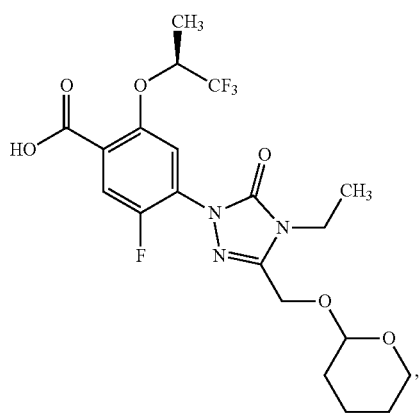

(A7)

to react with a compound of formula (xxx7):

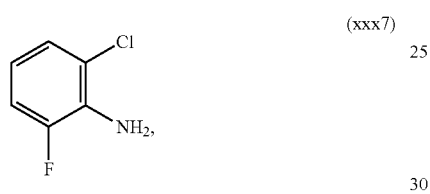

(xxx7)

in CH₃CN, by addition of pyridine, and phosphoryl chloride and cleavage of the protecting group under acidic conditions by using phosphoric acid in an alcohol, e.g. methanol, ethanol, or 2-propanol, preferably methanol, thereby giving Compound (I):

Compound (I)

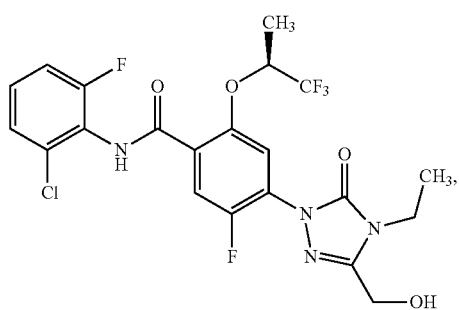

and optionally further comprising one or more purification steps selected from crystallization and recrystallization and optionally micronizing the product obtained.

In another embodiment, the present invention provides a method of preparing Compound (I) as defined supra, said method comprising the step of allowing an intermediate compound of formula (A7):

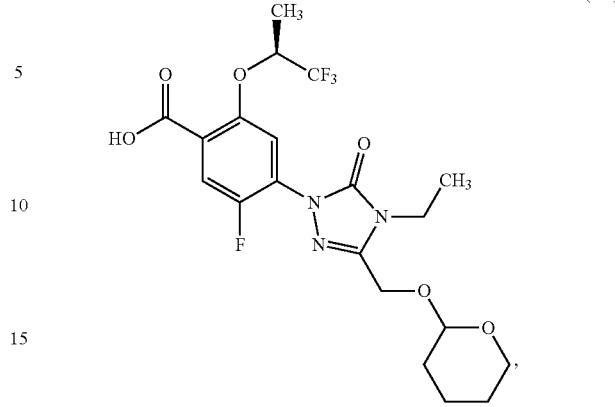

(A7)

to react with a compound of formula (xxx7):

(xxx7)

in CH₃CN, by addition of pyridine, and phosphoryl chloride and cleavage of the protecting group under acidic conditions by using phosphoric acid in an alcohol, e.g. methanol, ethanol, or 2-propanol, preferably methanol, thereby giving Compound (I):

Compound (I)

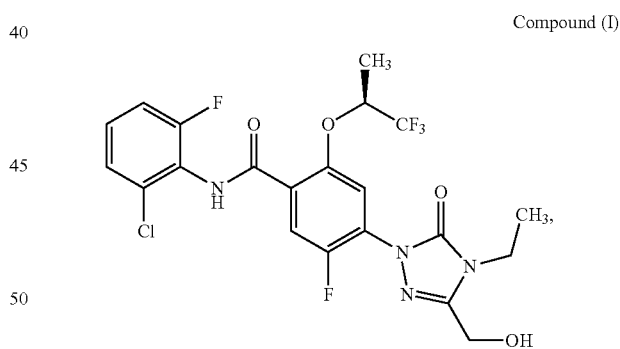

then optionally converting said Compound (I) into, an N-oxide or salt or a salt of an N-oxide using the corresponding (i) solvents and/or (ii) bases or acids and optionally further comprising one or more purification steps selected from e.g., crystallization, recrystallization and chromatography and optionally micronizing the product obtained.

In accordance with an embodiment of the first or the second aspect, the present invention provides a method of preparing Compound (I) as defined supra, said method comprising the step of allowing an intermediate compound of formula (A7)

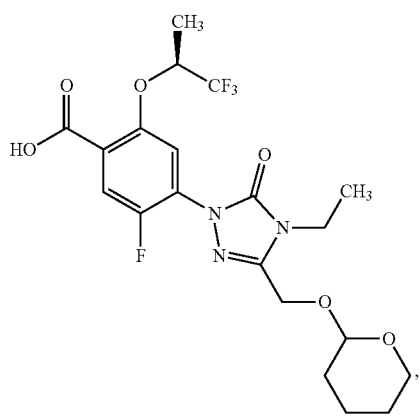

to react with a compound of formula (xxx7):

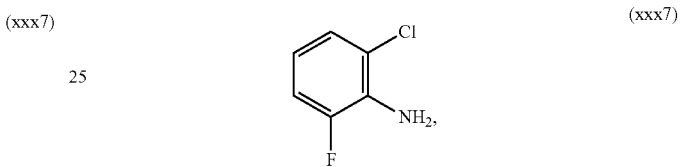

in CH₃CN, by addition of pyridine, and phosphoryl chloride and cleavage of the protecting group under acidic conditions by using phosphoric acid in an alcohol, e.g. methanol, ethanol, or 2-propanol, preferably methanol, thereby giving Compound (I):

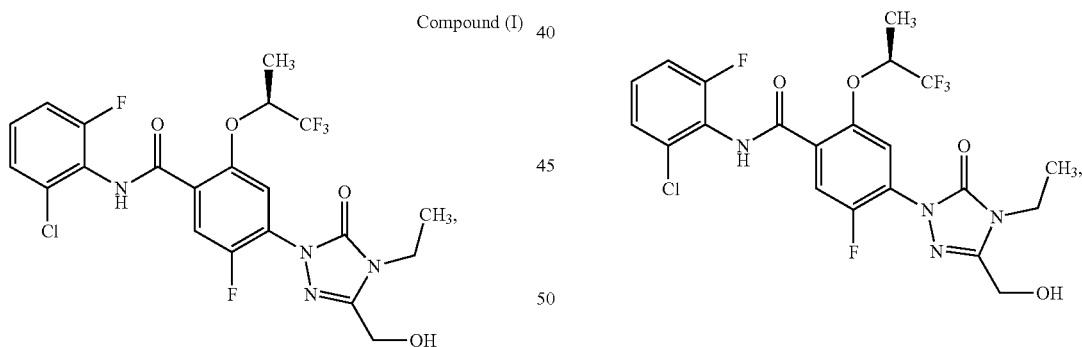

then optionally converting said Compound (I) into, an N-oxide or salt or a salt of an N-oxide using the corresponding (i) solvents and/or (ii) bases or acids and optionally further comprising one or more purification steps selected from e.g., crystallization, recrystallization and chromatography and optionally micronizing the product obtained.

In accordance with an embodiment of the first or the second aspect and any embodiments disclosed herein, the present invention provides a method of preparing Compound (I) as defined supra, said method comprising acid chloride formation or carboxylic acid activation in situ.

A further embodiment of any of the aspects and embodiments as defined herein is that the solvent used is a polar solvent, such as e.g. DMSO, CH₃CN, preferably CH₃CN, during formation of the acid chloride.

A further embodiment of any of the aspects and embodiments as defined herein is that an alcohol, such as methanol or ethanol, preferably ethanol is used to obtain purified Compound (I).

A further embodiment of the aspects and embodiments as defined herein is that the reaction of (A7) to (A8) to (A9) to Compound (I) is done in one reaction vessel without isolation of neither (A8) nor (A9).

A further embodiment of the aspects and embodiments as defined herein is that the reaction of (A7) to (A8) to (A9) to Compound (I) is done in one reaction vessel without isolation of neither (A8) nor (A9) and (A8) or similarly activated carboxylic acid are generated in situ.

In another embodiment of any of the aspects and embodiments as defined herein the reaction of (A7) to (A8) to (A9) is done in one reaction vessel without isolation of (A8).

In another embodiment of any of the aspects and embodiments as defined herein the reaction of (A7) to (A8) to (A9) is done in one reaction vessel without isolation of (A8) and (A8) or similarly activated carboxylic acid are generated in situ.

An embodiment of the present invention are the methods of preparing Compound (I), said methods comprising the steps as described in the Experimental Section herein.

In accordance with a another aspect, an embodiment of the present invention are intermediate compounds which are useful for the preparation of Compound (I), especially compounds (A4), (A5), (A6), (A7), (A8) and (A9).

As an aspect the invention provides the intermediate compound (A9.1):

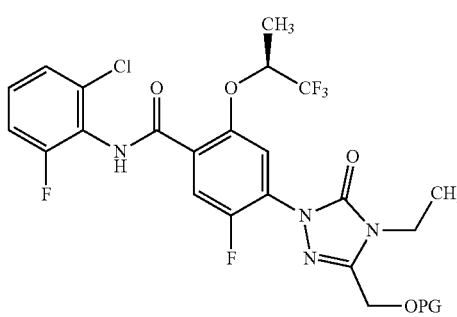

(A9.1)

wherein PG is a protecting group selected from Tetrahydropyranyl (THP), Tetrahydrofuranyl (THF), 1-Ethoxyethyl (EE), tert-Butyl (t-Bu), tert-Butoxymethyl, Methoxyethoxymethyl (MEM).

As a particular embodiment the invention provides the intermediate compound (A9):

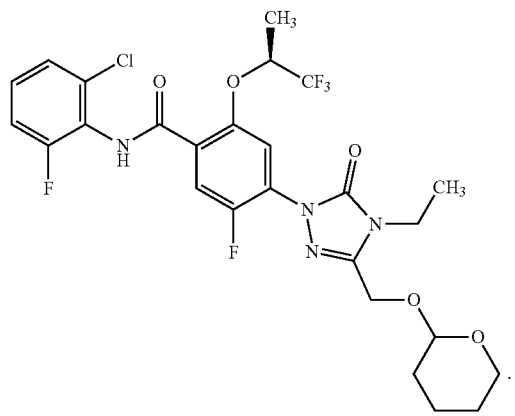

(A9)

As a further aspect the invention provides the intermediate compound (A7.1):

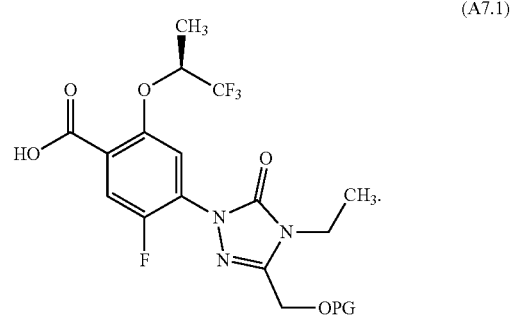

(A7.1)

wherein PG is a protecting group selected from. Tetrahydropyranyl (THP), Tetrahydrofuranyl (THF), 1-Ethoxyethyl (EE), tert-Butyl (t-Bu), tert-Butoxymethyl, Methoxyethoxymethyl (MEM).

As a further particular embodiment the invention provides the intermediate compound (A7):

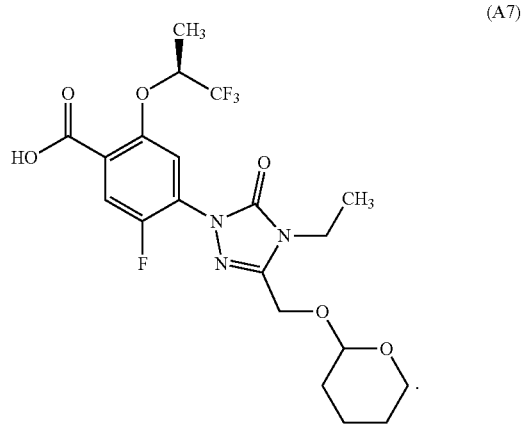 [SMILES: CCn1c(COC2CCCCO2)nn(-c2cc(O[C@@H](C)C(F)(F)F)c(C(=O)O)cc2F)c1=O]

(A7)

As a further aspect the invention provides the intermediate compound (A6.1):

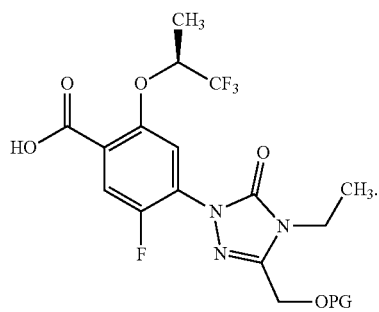

(A6.1)

wherein PG is a protecting group selected from Tetrahydropyranyl (THP), Tetrahydrofuranyl (THF), 1-Ethoxyethyl (EE), tert-Butyl (t-Bu), tert-Butoxymethyl, Methoxyethoxymethyl (MEM).

As a further particular embodiment the invention provides the intermediate compound (A6):

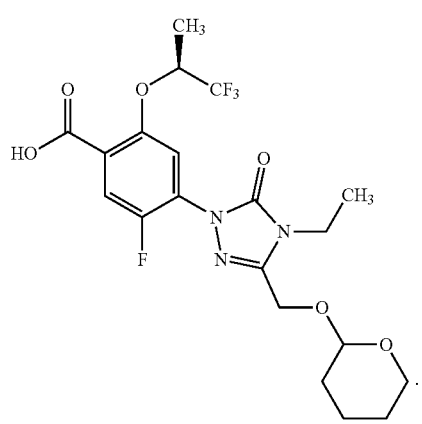

(A6)

As a further aspect the invention provides the intermediate compound (A5.1):

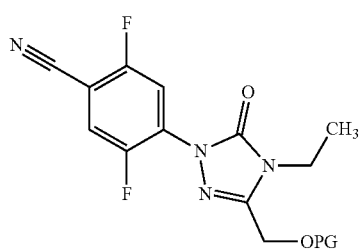

(A5.1)

wherein PG is a protecting group selected from Tetrahydropyranyl (THP), Tetrahydrofuranyl (THF), 1-Ethoxyethyl (EE), tert-Butyl (t-Bu), tert-Butoxymethyl, Methoxyethoxymethyl (MEM).

As a further particular embodiment the invention provides the intermediate compound (A5):

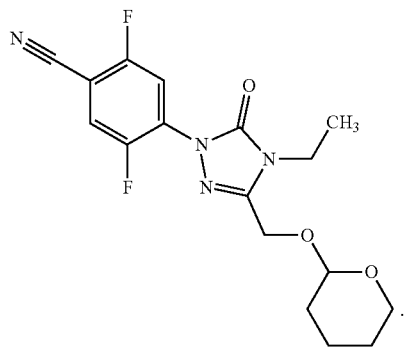

(A5)

In accordance with a further aspect, the present invention provides the use of said intermediate compounds for the preparation of Compound (I) as defined supra.

As a yet further embodiment the present invention provides the intermediate compounds which are disclosed in the Example Section of this text, infra.

The present invention provides any sub-combination within any embodiment or aspect of the present invention of the process as defined herein.

A further aspect of the invention is the crystalline form of Compound (I), N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, which is the crystalline form A.

A further aspect of the invention is crystalline form A of Compound (I).

Said crystalline form of Compound (I) is obtained by the process as described herein.

Thus another aspect of the invention is Compound (I) obtainable by the process as described infra.

In accordance with an embodiment of the third aspect and any embodiment disclosed herein, the invention provides a crystalline form A of Compound (I)

Compound (I)

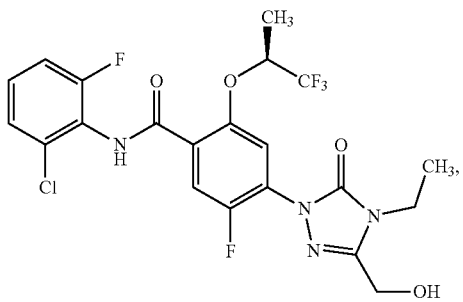

A further aspect of the invention is crystalline form A of Compound (I) characterized by its IR bands as indicated in the experimental section.

A further aspect of the invention is Compound (I) in its micronized form.

A yet further aspect the invention is Compound (I) having a particle size of 0.1 μm-100 μm (X10-X90).

An embodiment of the preceding aspect of the invention is Compound (I) having a particle size of 0.3 μm-20 μm (X10-X90).

An embodiment of the invention are micronized particles of Compound (I) within a size range of (X10-X90): 0.6-3.8 μm An embodiment of the invention are micronized particles of Compound (I) within a size range of (X10-X90): 0.6-3 µm The crystalline form A of Compound (I) shows beneficial properties over its amorphous form with regard to:
drug formulation ability
mechanical formulation stability In general different forms of a compound can be distinguished by X-ray powder diffraction, differential scanning calorimetry (DSC), IR-, Raman-, NIR-, FIR- and 13C-solid-state-NMR-spectroscopy.

The crystalline form A of Compound (I) can be characterized unambiguously by an Infrared spectrum which displays at least the following bands: 1699, 1688, 1511, preferably at least the following reflections: 1699, 1511, 1453, 1246, 1202 cm-1, more preferably at least the following reflections: 3382, 3265, 1699, 1688, 1511, 1453, 1202 $cm^{-1}$, most preferably at least the following reflections: [3382, 3265, 1699, 1688, 1511, 1453, 1246, 1202, 1095 and 1049 $cm^{-1}$ each quoted as Band maxima ($cm^{-1}$).

The crystalline form A of Compound (I) can also be characterized unambiguously by the Infrared Spectrum as shown in FIG. 1.

In a further embodiment at least the 3 most intense and/or characteristic bands of the Infrared spectrum of crystalline form A of compound (I) are observed at: 1699, 1688, 1511.

In a further embodiment at least the 5 most intense and/or characteristic bands of crystalline form A of compound (I) are observed at: 1699, 1688, 1511, 1453, 1202.

In a further embodiment at least the 7 most intense and/or characteristic bands of crystalline form A of compound (I) are observed at: 3382, 3265, 1699, 1688, 1511, 1453, 1202.

In a further embodiment at least the 10 most intense and/or characteristic bands of crystalline form A of compound (I) are observed at: 3382, 3265, 1699, 1688, 1511, 1453, 1246, 1202, 1095 and 1049 $cm^{-1}$.

A further aspect of the invention is crystalline form A of Compound (I) characterized by its X-ray powder diffractogram measured at 25° C. and with Cu—K alpha 1 as radiation source displaying at least the following reflections, quoted as 2Θ value±0.2°:17.2, 18.3, 19.1, 21.0, 25.2.

A further aspect of the invention is crystalline form A of Compound (I) characterized by its X-ray powder diffractogram measured at 25° C. and with Cu—K alpha 1 as radiation source displaying at least the reflections as indicated in the experimental section.

Figure 2:
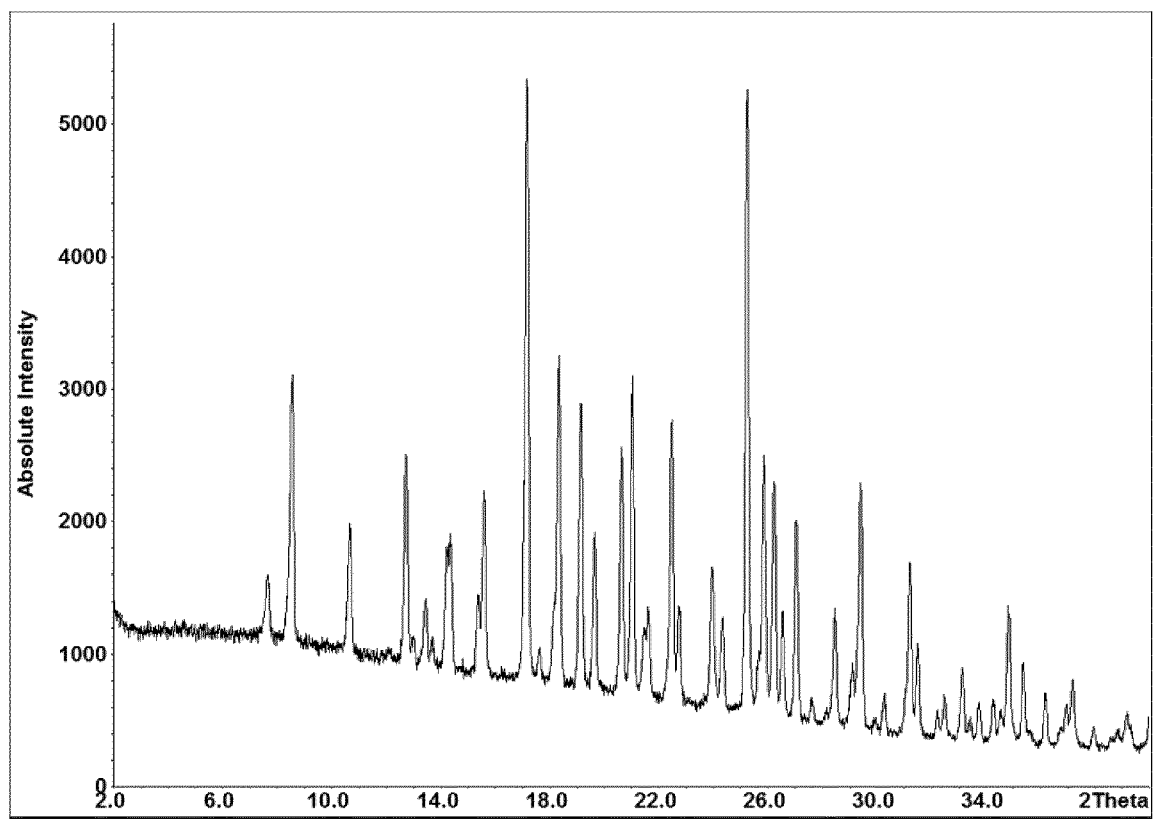

The crystalline form A of the compound of formula (I) can be characterized unambiguously by a X-Ray powder diffractogram (at 25° C. and with Cu—K alpha 1 as radiation source) which displays at least the following reflections: 17.2, 21.0, 25.2, preferably at least the following reflections: 17.2, 18.3, 19.1, 21.0, 22.5 and 25.2, more preferably at least the following reflections: 8.6, 17.2, 18.3, 19.1, 21.0, 22.5, 25.2; most preferably at least the following reflections: 8.6, 17.2, 18.3, 19.1, 20.6, 21.0, 22.5, 25.2, 25.9 and 29.4 each quoted as 2Θ value±0.2°. The crystalline form A of Compound (I) can also be characterized unambiguously by the X-Ray powder diffractogram (at 25° C. and with Cu—K alpha 1 as radiation source) as shown in FIG. 2.

Figure 4:
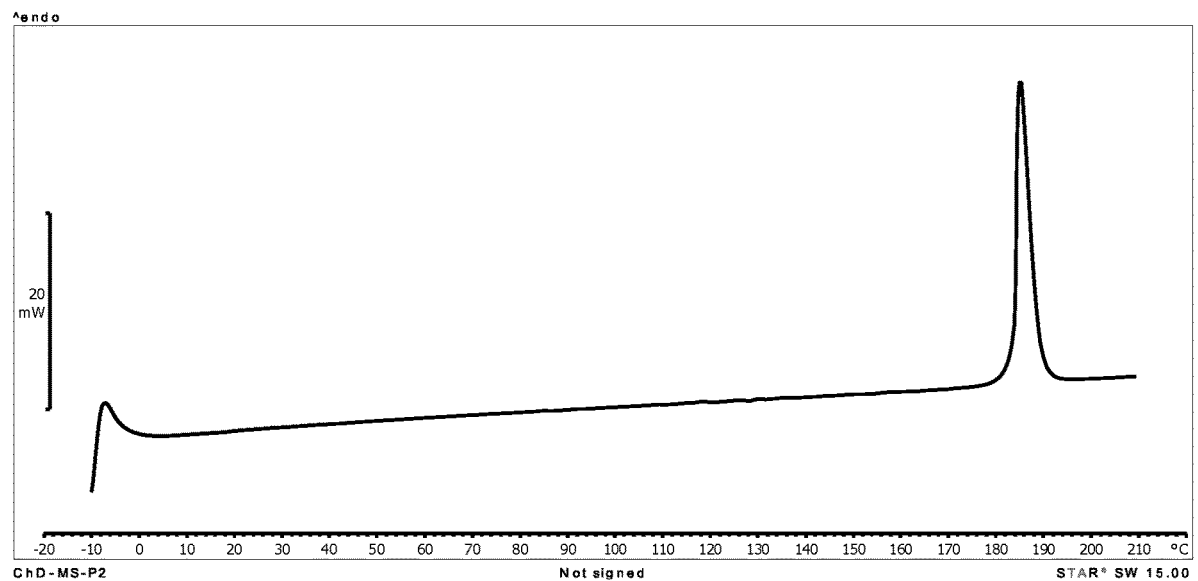

The crystalline form A of Compound (I) can also be characterized unambiguously by the DSC curve of crystalline micronized Compound (I) as shown in FIG. 4.

The crystalline form A of the Compound (I) according to the invention can be used alone or in combination with pharmaceutical acceptable excipients.

The crystalline form A is therefore suitable for use in the pharmaceutical field, in particular suitable for pharmaceutical compositions Thus one embodiment of the invention is the use of crystalline from A for the preparation of a pharmaceutical composition.

Thus a further aspect of the invention is a pharmaceutical composition comprising crystalline form A of Compound (I)

Thus a further aspect of the invention is a pharmaceutical composition comprising crystalline form A of Compound (I) and optionally comprising further pharmaceutically acceptable excipients.

A yet further aspect of the invention is the use of crystalline form A of Compound (I) for the preparation of a pharmaceutical composition.

Another aspect of the invention is the a pharmaceutical composition mentioned herein for use in the treatment of a hyperproliferative disease, such as cancer.

Another aspect of the invention is the use of a pharmaceutical composition mentioned herein for the preparation of a medicament for the treatment of a hyperproliferative disease, such as cancer.

A yet further aspect of the invention is the use of a pharmaceutical composition comprising crystalline form A of Compound (I) and optionally comprising further pharmaceutically acceptable excipients for the treatment of cancer, wherein the cancer disease is selected from cancers of breast; brain; digestive tract; eye; head and neck; haematological malignancies including leukemias, lymphomas, multiple myelomas; liver; parathyroid and their distant metastases; respiratory tract; reproductive organs; urinary tract; sarcomas; skin; thyroid.

A preferred embodiment of the present invention is a pharmaceutical composition comprising crystalline form A of the Compound (I) mainly and optionally further pharmaceutically acceptable excipients not further comprising significant fractions of another form of the Compound (I).

It is possible for Compound (I) to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for Compound (I) to be administered in suitable administration forms.

For oral administration, it is possible to formulate the compounds according to the invention to dosage forms known in the art that deliver Compound (I) rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixture agitandae), lipophilic suspensions, emulsions, ointments, creams, transdermal therapeutic systems (such as, for example, patches), milk, pastes, foams, dusting powders, implants or stents.

Compound (I) can be incorporated into the stated administration forms. This can be effected in a manner known per se by mixing with pharmaceutically suitable (acceptable) excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides, fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The crystalline form A of the Compound (I), according to the invention may have useful pharmacological properties and may be employed for the prevention and treatment of disorders in humans and animals, more specifically for the treatment of hyperproliferative diseases such as cancer.

The crystalline forms of Compound (I) can be used for the treatment of hyperproliferative disorders, especially cancer.

In some embodiments, the present invention further relates to a method for the treatment and/or prophylaxis of diseases, in particular hyperproliferative diseases, particularly cancer, using an effective amount of crystalline form A of Compound (I) according to the invention.

In some embodiments, the present invention further relates to a method for the treatment and/or prophylaxis of a hyperproliferative disease, such as cancer using an effective amount of crystalline form A of Compound (I) according to the invention.

Hyperproliferative disorders (disease) include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include sarcomas, and haematological malignancies including but not limited to leukemias, lymphomas, multiple myelomas.

One aspect of the invention is the use of crystalline form A of Compound (I) either as obtained by chemical reaction as described herein and optionally crystallization and/or recrystallization and/or in its micronized form for the treatment of cancer.

One aspect of the invention is crystalline form A of Compound (I) either as obtained by chemical reaction as described herein and optionally crystallization and/or recrystallization and/or in its micronized form for use in the treatment of cancer as well as a method of treatment of cancer diseases comprising administering a specific amount of crystalline form A of Compound (I) either as obtained by chemical reaction as described herein and optionally crystallization and/or recrystallization and/or in its micronized form.

Examples of breast cancers include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypothalmic glioma, glioma, glioblastoma, cerebellar and cerebral astrocytoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell lymphoma DLBCL, double-hit lymphoma and double-expressor lymphoma; anaplastic large cell lymphoma, B-cell lymphoma, cutaneous T-cell lymphoma, Burkitt's lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma and Sezary syndrome.

Sarcomas include, but are not limited to, sarcoma of the soft tissue, gliosarcoma, osteosarcoma, malignant fibrous histiocytoma, lymphosarcoma, and rhabdomyosarcoma.

Leukemias include, but are not limited to acute lymphoblastic leukemia, acute myeloid leukemia, (acute) T-cell leukemia, acute lymphoblastic leukemia, acute lymphocytic leukemia (ALL), acute monocytic leukemia (AML), acute promyelocytic leukemia (APL), bisphenotypic B myelomonocytic leukemia, chronic lymphocytic leukemia, chronic myelogenous leukemia, chronic myeloid leukemia (CML), chronic myelomonocytic leukemia (CMML), large granular lymphocytic leukemia, plasma cell leukemia, and also myelodysplastic syndrome (MDS), which can develop into an acute myeloid leukemia.

Inhibition of DHODH can also lead to differentiation of tumor initiating cells in hematological and solid cancers, especially leukemias.

The present invention also provides methods of treating angiogenic disorders including diseases associated with excessive and/or abnormal angiogenesis.

Inappropriate and ectopic expression of angiogenesis can be deleterious to an organism. A number of pathological conditions are associated with the growth of extraneous blood vessels. These include, for example, diabetic retinopathy, ischemic retinal-vein occlusion, and retinopathy of prematurity [Aiello et al., New Engl. J. Med., 1994, 331, 1480; Peer et al., Lab. Invest., 1995, 72, 638], age-related macular degeneration (AMD) [Lopez et al., Invest. Opthtalmol. Vis. Sci., 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of general formula (I) of the present invention can be utilized to treat and/or prevent any of the aforementioned angiogenesis disorders, for example by inhibiting and/or reducing blood vessel formation; by inhibiting, blocking, reducing, decreasing, etc. endothelial cell proliferation, or other types involved in angiogenesis, as well as causing cell death or apoptosis of such cell types.

Another aspect of the invention is a method for controlling cancer (e.g., through treatment, prophylaxis, etc.) in a subject (e.g., human, rat, etc.) by administering an effective amount of crystalline form A of Compound (I) either as obtained by chemical reaction as described herein and optionally crystallization or recrystallization or in its micronized form, or a pharmaceutically acceptable salt thereof, to the subject.

In some embodiments, the subject may be administered a medicament, comprising crystalline form A of Compound (I) either as obtained by chemical reaction as described herein and optionally crystallization or recrystallization or in its micronized form and one or more pharmaceutically acceptable excipients.

In some embodiments, the subject may be administered a medicament, comprising crystalline form A of Compound (I) either as obtained by chemical reaction as described herein and optionally crystallization or recrystallization or in its micronized form and one or more pharmaceutically acceptable carriers, excipients and/or diluents.

In some embodiments, the method of treatment and/or prophylaxis of a hyperproliferative disorder in a subject may comprise administering to the subject an effective amount of crystalline form A of Compound (I) either as obtained by chemical reaction as described herein and optionally crystallization or recrystallization or in its micronized form.

In one embodiment the hyperproliferative disorder may be, for example, cancer, the cancer types as defined supra, more particularly leukemia, lymphoma, solid tumors, such as e.g. brain cancer, colorectal carcinoma, lung cancer, ovarian cancer, pancreatic cancer, renal cancer, even more particularly e.g. acute myeloid leukemia, colorectal carcinoma, leukemia, lung cancer, lymphoma, multiple myeloma, ovarian cancer, pancreatic cancer and renal cell carcinoma.

In one embodiment the hyperproliferative disorder may be, for example, cancer, the cancer types are selected from acute myeloid leukemia, breast cancer, colorectal carcinoma, gastric cancer, gliosarcoma, head & neck cancer, hepatocellular carcinoma, leukemia, lung cancer, lymphoma, multiple myeloma, neuroblastoma, ovarian cancer, pancreatic cancer, prostate cancer, renal cell carcinoma, and sarcoma.

In one embodiment the hyperproliferative disorder may be, for example, cancer, more particularly lymphoma, wherein the lymphoma is selected from the group AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell DLBCL, double-hit lymphoma and double-expressor lymphoma; anaplastic large cell lymphoma, B-cell lymphoma, cutaneous T-cell lymphoma, Burkitt lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma.

In one embodiment the hyperproliferative disorder may be, for example, cancer, more particularly leukemia, wherein the leukemia is selected from the group acute lymphoblastic leukemia, acute myeloid leukemia, (acute) T-cell leukemia, acute lymphoblastic leukemia, acute lymphocytic leukemia, acute monocytic leukemia, acute promyelocytic leukemia, bisphenotypic B myelomonocytic leukemia, chronic lymphocytic leukemia, chronic myelogenous leukemia, chronic myeloid leukemia, chronic myelomonocytic leukemia, large granular lymphocytic leukemia, plasma cell leukemia, and also myelodysplastic syndrome, which can develop into an acute myeloid leukemia.

In some embodiments, the method of treatment and/or prophylaxis of a hyperproliferative disorder in a subject may comprise administering to the subject an effective amount of crystalline form A of Compound (I) either as obtained by chemical reaction as described herein and optionally crystallization or recrystallization or in its micronized form. The hyperproliferative disorder may be, for example, cancer (e.g., lung cancer, acute myeloid leukemia, acute promyelocytic leukemia (APL), mixed-lineage leukemia (MLL), chronic myeloid leukemia (CML), myelodysplastic syndrome (MDS), lymphoma, glioblastoma, prostate cancer, or any other cancer indication as defined herein).

In another aspect, the present invention provides the use of crystalline form A of Compound (I) either as obtained by chemical reaction as described herein and optionally crystallization or recrystallization or in its micronized form, or a pharmaceutically acceptable salt thereof, for the preparation of a medicament for the treatment or prophylaxis of a disease.

In another aspect, the present invention provides the use of crystalline form A of Compound (I) either as obtained by chemical reaction as described herein and optionally crystallization or recrystallization or in its micronized form, or a pharmaceutically acceptable salt thereof, for the treatment of cancer, which cancer is selected from acute myeloid leukemia, colorectal carcinoma, leukemia, lung cancer, lymphoma, multiple myeloma, ovarian cancer, pancreatic cancer and renal cell carcinoma.

In another aspect the invention provides methods of treatment of cancer comprising administering crystalline form A of Compound (I) either as obtained by chemical reaction as described herein and optionally crystallization or recrystallization or in its micronized form or a pharmaceutically acceptable salt, polymorph, metabolite, hydrate, solvate or ester thereof, where the cancer is selected from acute myeloid leukemia, colorectal carcinoma, leukemia, lung cancer, lymphoma, multiple myeloma, ovarian cancer, pancreatic cancer and renal cell carcinoma.

In another aspect, the present invention provides the use of crystalline form A of Compound (I) either as obtained by chemical reaction as described herein and optionally crystallization or recrystallization or in its micronized form, or a pharmaceutically acceptable salt thereof, for the treatment of cancer, which cancer is selected from acute myeloid leukemia, breast cancer, brain cancer, colorectal carcinoma, gastric cancer, gliosarcoma, head & neck cancer, hepatocellular carcinoma, leukemia, lung cancer, lymphoma, multiple myeloma, neuroblastoma, ovarian cancer, pancreatic cancer, prostate cancer, renal cell carcinoma, and sarcoma.

In another aspect the invention provides methods for the treatment of cancer comprising administering crystalline form A of Compound (I) either as obtained by chemical reaction as described herein and optionally crystallization or recrystallization or in its micronized form or a pharmaceutically acceptable salt thereof, where the cancer is selected from acute myeloid leukemia, brain cancer, breast cancer, colorectal carcinoma, gastric cancer, gliosarcoma, head & neck cancer, hepatocellular carcinoma, leukemia, lung cancer, lymphoma, multiple myeloma, neuroblastoma, ovarian cancer, pancreatic cancer, prostate cancer, renal cell carcinoma, and sarcoma.

In another aspect, the present invention provides the use of crystalline form A of Compound (I) either as obtained by chemical reaction as described herein and optionally crystallization or recrystallization or in its micronized form, or a pharmaceutically acceptable salt thereof, for the treatment of cancer, which cancer is selected from acute T-cell lymphoblastic leukemia, acute promyelocytic leukemia, acute myeloid leukemia, anaplastic large cell lymphoma, biphenotypic B myelomonocytic leukemia, B-cell lymphoma, breast cancer, Burkitt lymphoma, chronic myeloid leukemia, colorectal carcinoma, gastric cancer, gliosarcoma, head & neck cancer, hepatocellular carcinoma, lung cancer, multiple myeloma, neuroblastoma, ovarian cancer, pancreatic cancer, prostate cancer, renal cell carcinoma, sarcoma and T-cell lymphoma.

In another aspect the invention provides methods of treatment of cancer comprising administering crystalline form A of Compound (I) either as obtained by chemical reaction as described herein and optionally crystallization or recrystallization or in its micronized form or a pharmaceutically acceptable salt thereof, where the cancer is selected from acute T-cell lymphoblastic leukemia, acute promyelocytic leukemia, acute myeloid leukemia, anaplastic large cell lymphoma, biphenotypic B myelomonocytic leukemia, B-cell lymphoma, brain cancer, breast cancer, Burkitt lymphoma, chronic myeloid leukemia, colorectal carcinoma, gastric cancer, gliosarcoma, head & neck cancer, hepatocellular carcinoma, lung cancer, multiple myeloma, neuroblastoma, ovarian cancer, pancreatic cancer, prostate cancer, renal cell carcinoma, sarcoma and T-cell lymphoma.

In another aspect, the present invention provides the use of crystalline form A of Compound (I) either as obtained by chemical reaction as described herein and optionally crystallization or recrystallization or in its micronized form, or a pharmaceutically acceptable salt thereof, for the treatment of cancer, which cancer is selected from lung cancer, leukemia, acute myeloid leukemia, gliosarcoma, colorectal carcinoma, head & neck cancer, hepatocellular carcinoma, multiple myeloma, lymphoma, breast cancer, neuroblastoma, ovarian cancer, gastric cancer, pancreatic cancer, prostate cancer, renal cell carcinoma, and sarcoma.

In another aspect, the present invention provides the use of crystalline form A of Compound (I) either as obtained by chemical reaction as described herein and optionally crystallization or recrystallization or in its micronized form, or a pharmaceutically acceptable salt thereof, for the treatment of cancer, which cancer is selected from leukemias, lymphomas, sarcomas and solid tumors.

In another aspect the invention provides methods for the treatment of cancer comprising administering crystalline form A of Compound (I) either as obtained by chemical reaction as described herein and optionally crystallization or recrystallization or in its micronized form or a pharmaceutically acceptable salt thereof, wherein the cancer is selected from leukemias, lymphomas, sarcomas and solid tumors.

In another aspect, the present invention provides methods for use of crystalline form A of Compound (I) either as obtained by chemical reaction as described herein and optionally crystallization or recrystallization or in its micronized form or a pharmaceutically acceptable salt thereof, for the treatment of cancer and methods of treating cancer, which cancer is selected from colorectal cancer, leukemia and lymphoma. In another aspect the invention provides methods for the treatment of cancer comprising administering crystalline form A of Compound (I) either as obtained by chemical reaction as described herein and optionally crystallization or recrystallization or in its micronized form or a pharmaceutically acceptable salt thereof, wherein the cancer is selected from colorectal cancer, leukemia and lymphoma.

In another aspect, the present invention provides the use of crystalline form A of Compound (I) either as obtained by chemical reaction as described herein and optionally crystallization or recrystallization or in its micronized form, or a pharmaceutically acceptable salt thereof, for the treatment of cancer and methods of treating cancer, which cancer is selected from colorectal cancer, leukemia and lymphoma.

In another aspect the invention provides methods of treatment of cancer comprising administering crystalline form A of Compound (I) either as obtained by chemical reaction as described herein and optionally crystallization or recrystallization or in its micronized form or a pharmaceutically acceptable salt thereof, wherein the cancer is selected from colorectal cancer, leukemia and lymphoma.

In another aspect, the present invention provides the use of crystalline form A of Compound (I) either as obtained by chemical reaction as described herein and optionally crystallization or recrystallization or in its micronized form, or a pharmaceutically acceptable salt thereof, for the treatment of one or more cancer types and methods of treating one or more cancer types, where cancer is selected from ALL, AML, APL, CMML, DLBCL, MDS, MCL, T-NHL, colorectal cancer, melanoma and ovarian cancer.

In another aspect the invention provides methods for the treatment of cancer comprising administering crystalline form A of Compound (I) either as obtained by chemical reaction as described herein and optionally crystallization or recrystallization or in its micronized form or a pharmaceutically acceptable salt thereof, where the cancer is selected from ALL, AML, APL, CMML, DLBCL, MDS, MCL, T-NHL, colorectal cancer, melanoma and ovarian cancer.

In another aspect, the present invention provides the use of crystalline form A of Compound (I) either as obtained by chemical reaction as described herein and optionally crystallization or recrystallization or in its micronized form, or a pharmaceutically acceptable salt thereof, for the treatment of one or more cancer types, where cancer is selected from leukemias including but not limited to acute lymphoblastic leukemia (ALL), acute myeloid leukemia (AML), acute T-cell leukemia, acute monocytic leukemia, acute promyelocytic leukemia (APL), bisphenotypic B myelomonocytic leukemia, chronic myelogenous leukemia, chronic myeloid leukemia, chronic myelomonocytic leukemia (CMML), large granular lymphocytic leukemia, and myelodysplastic syndrome (MDS), which can develop into an acute myeloid leukemia, lymphomas including but not limited to AIDS-related lymphoma, chronic lymphocytic lymphoma, non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell DLBCL, double-hit lymphoma and double-expressor lymphoma; anaplastic large cell lymphoma, B-cell lymphoma, cutaneous T-cell lymphoma, Burkitt lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma;

sarcomas including but not limited to sarcoma of the soft tissue, gliosarcoma, osteosarcoma, malignant fibrous histiocytoma, lymphosarcoma, and rhabdomyosarcoma; and solid tumors including but not limited to brain cancer, breast cancer, colorectal carcinoma, gastric cancer, gliosarcoma, head & neck cancer, hepatocellular carcinoma, lung cancer, multiple myeloma, neuroblastoma, ovarian cancer, pancreatic cancer, prostate cancer, renal cell carcinoma and sarcoma.

In another aspect the invention provides method for the treatment of cancer comprising administering an effective amount of crystalline form A of Compound (I) either as obtained by chemical reaction as described herein and optionally crystallization or recrystallization or in its micronized form where the cancer is selected from leukemias including but not limited to acute lymphoblastic leukemia (ALL), acute myeloid leukemia (AML), acute T-cell leukemia, acute monocytic leukemia, acute promyelocytic leukemia, bisphenotypic B myelomonocytic leukemia, chronic myelogenous leukemia, chronic myeloid leukemia, chronic myelomonocytic leukemia (CMML), large granular lymphocytic leukemia, and myelodysplastic syndrome (MDS), which can develop into an acute myeloid leukemia, lymphomas including but not limited to AIDS-related lymphoma, chronic lymphocytic lymphoma, non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell DLBCL, double-hit lymphoma and double-expressor lymphoma; anaplastic large cell lymphoma, B-cell lymphoma, cutaneous T-cell lymphoma, Burkitt lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma;

sarcomas including but not limited to sarcoma of the soft tissue, gliosarcoma, osteosarcoma, malignant fibrous histiocytoma, lymphosarcoma, and rhabdomyosarcoma; and solid tumors including but not limited to brain cancer, breast cancer, colorectal carcinoma, gastric cancer, gliosarcoma, head & neck cancer, hepatocellular carcinoma, lung cancer, multiple myeloma, neuroblastoma, ovarian cancer, pancreatic cancer, prostate cancer, renal cell carcinoma and sarcoma.

In another aspect, the present invention provides a method for inhibiting cell proliferation or viability in a cancer cell, the method comprising contacting the cell with crystalline form A of Compound (I) either as obtained by chemical reaction as described herein and optionally crystallization or recrystallization or in its micronized form herein, thereby inhibiting cell proliferation or viability.

In a further aspect the present invention provides a method for inhibiting Dihydroorotate Dehydrogenase (DHODH) enzymatic activity, the method comprising contacting DHODH crystalline form A of Compound (I) either as obtained by chemical reaction as described herein and optionally crystallization or recrystallization or in its micronized form, thereby inhibiting DHODH enzymatic activity.

In yet a further aspect the present invention provides a method for treating lymphoma in a subject, the method comprising administering to the subject an effective amount of crystalline form A of Compound (I) either as obtained by chemical reaction as described herein and optionally crystallization or recrystallization or in its micronized form, thereby treating the lymphoma.

In yet a further aspect the present invention provides a method for treating lymphoma mentioned above in a subject, wherein the lymphoma is selected from the group AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell DLBCL, double-hit lymphoma and double-expressor lymphoma; anaplastic large cell lymphoma, B-cell lymphoma, cutaneous T-cell lymphoma, Burkitt lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma.

In another aspect, the present invention provides a method for treating leukemia in a subject, the method comprising administering to the subject an effective amount of crystalline form A of Compound (I) either as obtained by chemical reaction as described herein and optionally crystallization or recrystallization or in its micronized form, thereby treating the leukemia.

In yet a further aspect the present invention provides a method for treating leukemia mentioned above, wherein the leukemia is selected from the group acute lymphoblastic leukemia, acute myeloid leukemia, (acute) T-cell leukemia, acute lymphoblastic leukemia, acute lymphocytic leukemia, acute monocytic leukemia, acute promyelocytic leukemia, bisphenotypic B myelomonocytic leukemia, chronic lymphocytic leukemia, chronic myelogenous leukemia, chronic myeloid leukemia, chronic myelomonocytic leukemia, large granular lymphocytic leukemia, plasma cell leukemia, and also myelodysplastic syndrome, which can develop into an acute myeloid leukemia.

A yet further embodiment is the use of the pharmaceutical composition comprising the crystalline form A of Compound (I) for the treatment of hyperproliferative diseases, more particularly cancer.

A yet further embodiment is the use of the pharmaceutical composition comprising the crystalline form of Compound (I) for the treatment of
leukemias including but not limited to acute lymphoblastic leukemia (ALL), acute myeloid leukemia (AML), acute T-cell leukemia, acute monocytic leukemia, acute promyelocytic leukemia, bisphenotypic B myelomonocytic leukemia, chronic myelogenous leukemia, chronic myeloid leukemia, chronic myelomonocytic leukemia (CMML), large granular lymphocytic leukemia, and myelodysplastic syndrome (MDS), which can develop into an acute myeloid leukemia,
lymphomas including but not limited to AIDS-related lymphoma, chronic lymphocytic lymphoma, non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell DLBCL, double-hit lymphoma and double-expressor lymphoma; anaplastic large cell lymphoma, B-cell lymphoma, cutaneous T-cell lymphoma, Burkitt lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma;
sarcomas including but not limited to sarcoma of the soft tissue, gliosarcoma, osteosarcoma, malignant fibrous histiocytoma, lymphosarcoma, and rhabdomyosarcoma;
and
solid tumors including but not limited to brain cancer, breast cancer, colorectal carcinoma, gastric cancer, gliosarcoma, head & neck cancer, hepatocellular carcinoma, lung cancer, multiple myeloma, neuroblastoma, ovarian cancer, pancreatic cancer, prostate cancer, renal cell carcinoma and sarcoma.

A yet further embodiment is the use of the pharmaceutical composition comprising the crystalline form of Compound (I) having a particle size of 0.1 µm-100 µm, preferably 0.1 µm-50 µm, more preferably 0.3 µm-20 µm for the treatment of cancer.

A yet further embodiment is the use of the pharmaceutical composition comprising the crystalline form of Compound (I) having a particle size of 0.3 µm-4 µm.

A yet further embodiment is the use of the pharmaceutical composition comprising the crystalline form of Compound (I) having a particle size of 0.6 µm-3.8 µm.

A yet further embodiment is the use of the pharmaceutical composition comprising the crystalline form of Compound (I) having a particle size of 0.6 µm-3 µm.

The crystalline form A of the Compound (I) according to the invention can be used alone or in combination with other active substances if necessary.

Thus one aspect of the invention is the use of crystalline form A of Compound (I) for the preparation of a pharmaceutical composition optionally further comprising pharmaceutically acceptable excipients and further comprising:
one or more further active ingredients in particular anti-cancer agents.

Thus the present invention further relates to medicinal products containing the crystalline form A of Compound (I) according to the invention and one or more further active substances, e.g. anti-cancer agents, in particular for the treatment and/or prophylaxis of the aforementioned diseases. As suitable other active substances the following can be mentioned:
131I-chTNT, abarelix, abemaciclib, abiraterone, acalabrutinib, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, apalutamide, aprepitant, arcitumomab, arglabin, arsenic trioxide, asparaginase, atezolizumab, avelumab, axicabtagene ciloleucel, axitinib, azacitidine, basiliximab, belotecan, bendamustine, besilesomab, belinostat, bevacizumab, bexarotene, bicalutamide, bisantrene, bleomycin, blinatumomab, bortezomib, bosutinib, buserelin, brentuximab vedotin, brigatinib, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, durvalumab, eculizumab, edrecolomab, elliptinium acetate, elotuzumab, eltrombopag, enasidenib, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, inotuzumab ozogamicin, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, lutetium Lu 177 dotatate, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, midostaurin, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, mvasi, nabilone, nabiximols, nafarelin, naloxone+pentazocine, naltrexone, nartograstim, necitumumab, nedaplatin, nelarabine, neratinib, neridronic acid, netupitant/palonosetron, nivolumab, pentetreotide, nilotinib, nilutamide, nimorazole, nimotuzumab, nimustine, nintedanib, niraparib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, ribociclib, risedronic acid, rhenium-186 etidronate, rituximab, rolapitant, romidepsin, romiplostim, romurtide, rucaparib, samarium (153Sm) lexidronam, sargramostim, sarilumab, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tisagenlecleucel, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Another aspect of the invention are kits comprising Compound (I) in crystalline form A optionally in micronized form together with further anti-cancer agents.

EXPERIMENTAL SECTION

NMR peak forms are stated as they appear in the spectra, possible higher order effects have not been considered.

Chemical names were generated using the ACD/Name software from ACD/Labs. In some cases generally accepted names of commercially available reagents were used in place of ACD/Name generated names.

The following table 1 lists the abbreviations used in this paragraph and in the Examples section as far as they are not explained within the text body. Other abbreviations have their meanings customary per se to the skilled person.

TABLE 1

Abbreviations
The following table lists the abbreviations used herein.

| | |
|---|---|
| Ac | acetyl |
| aq. | aqueous (solution) |
| br. | broad ($^1$H-NMR signal) |
| Bu | butyl |
| cat. | catalytic |
| conc. | concentrated |
| COMU ® | (1-Cyano-2-ethoxy-2-oxoethylidenaminooxy) dimethylamino-morpholino-carbenium-hexafluorophosphat |
| d | doublet ($^1$H-NMR signal) |
| DCI | direct chemical ionization (MS) |
| DCM | dichloromethane |
| DIPEA | N,N-diisopropylethylamine |
| DMF | N,N-dimethylformamide |
| DMSO | dimethylsulfoxide |
| DSC | Differentiation Scanning Calorimetry |
| EI | electron impact ionization (MS) |
| eq. | equivalent(s) |
| ESI | electro-spray ionization (MS) |
| Et | ethyl |

TABLE 1-continued

Abbreviations
The following table lists the abbreviations used herein.

| | |
|---|---|
| EtOAc | ethyl acetate |
| GCMS | gas chromatography-coupled mass spectroscopy |
| h | hour(s) |
| Hal | halogen |
| ¹H-NMR | proton nuclear magnetic resonance spectroscopy |
| HPLC | high performance liquid chromatography |
| iPr | isopropyl |
| LCMS | liquid chromatography-coupled mass spectroscopy |
| Me | methyl |
| MeOH | methanol |
| min | minute(s) |
| MS | mass spectroscopy |
| m/z | mass-to-charge ratio (MS) |
| n-Bu | n-butyl |
| of th. | of theory (chemical yield) |
| Ph | phenyl |
| q | quartet (¹H-NMR signal) |
| quant. | Quantitative (yield) |
| RP | reverse phase (HPLC) |
| rt | room temperature |
| $R_t$ | retention time (HPLC) |
| s | singlet (¹H-NMR signal) |
| sat. | saturated (solution) |
| t | triplet (¹H-NMR signal) |
| tert | tertiary |
| TGA | Thermogravimetric Analysis |
| THF | tetrahydrofuran |
| TLC | thin layer chromatography |

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or DCM/methanol. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Particle size distributions were obtained from Laser light diffraction measurements of particle size. X followed by a number is the notation used for the particle diameter corresponding to a certain percentage of the cumulative undersize distribution (on a volume basis). Thus, for example, [y μm] X90 is the particle diameter y below which 90% of the particle population lies. Basis for the calculation is the instrumental set-up as disclosed in examples 9-1 and 9-2.

LCMS (Method 1): HSST3
Instrument: Waters ACQUITY SQD UPLC system; column: Waters Acquity UPLC HSS T3 1.8 μm 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; flow rate: 0.40 ml/min; UV detection: 208-400 nm.

LCMS (Method 3): MCW-FT-MS-M1
Instrument: Thermo Scientific FT-MS UHPLC+ system; Thermo Scientific UltiMate 3000; column: Waters, HSST3, 2.1×75 mm, C18 1.8 μm; eluent A: 1 l water+0.01% formic acid; eluent B: 1 l acetonitrile+0.01% formic acid; gradient: 0.0 min 10% B→2.5 min 95% B→3.5 min 95% B; oven: 50° C.; flow rate: 0.90 ml/min; UV detection: 210 nm/Optimum Integration Path 210-300 nm GCMS (Method 1): DSQ-II
Instrument: Thermo Scientific DSQII, Thermo Scientific Trace GC Ultra system; column: Restek RTX-35MS, 15 m×200 μm×0.33 μm; constant helium flow: 1.20 ml/min; oven: 60° C.; inlet: 220° C.; gradient: 60° C., 30° C./min→300° C. (hold time 3.33 min).

HPLC Method 1:
System: High performance liquid chromatograph equipped with gradient pumps, UV detector & attached with data recorder and integrator software; column: Zorbax Poroshell 120-SB C18 (50*4.6 mm, 2.7 μm); flow: 2.5 mL/min; column temperature: 45° C.; injection volume 3 μL, detection 210 nm, run time: 30 min; mobile phase A: 6.8 g KH2PO4 and 3.8 g H3PO4 (85%) in 5 L mili-Q water; mobile phase B: acetonitrile; gradient programme (T/% B): 0/5, 4/80, 5/80.

Experimental Section—Examples

Example 1

2-Tetrahydropyran-2-yloxyacetohydrazide (A1)

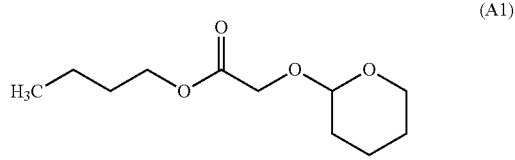

(A1)

450 g (3.40 mol) Butyl-hydroxyacetate (xxx1) was initially charged to 2250 ml dichloromethane. 4-Toluolsulfonic acid monohydrate 5.5 g (0.03 mol) was added at 20° C. 3,4-Dihydro-2H-pyran (309 g, 3.68 mol) (xxx2) was added over a period of 30 min at an internal temperature below 35° C. The mixture was subsequently cooled to 22° C. and stirred further for 16 h.

1125 ml saturated aqueous sodium hydrogen carbonate were added, the organic phase was separated and initially evaporated under reduced pressure at 50° C. bath temperature/3 mbar to receive 751 g of a dark orange oil. Further distillation for removal of impurities (80° C. bath temperature/0.25 mbar) gave 659 g (A1) as distillation residue as a dark orange oil in 89% yield.

The crude product was directly converted to the next stage.

$^1$H NMR (400 MHz, DMSO-d$_6$) δ ppm 0.89 (t, J=7.40 Hz, 3H) 1.33 (dq, J=14.93, 7.41 Hz, 2H) 1.39-1.79 (m, 10H) 3.38-3.47 (m, 1H) 3.74 (ddd, J=11.34, 8.41, 3.36 Hz, 1H) 4.00-4.20 (m, 2H) 4.66 (t, J=3.24 Hz, 1H)

GCMS (method 1): R$_f$=4.63 min; MS m/z=215 (M−H)$^+$, 105, 101, 85

Example 2

4-Ethyl-3-(tetrahydropyran-2-yloxymethyl)-1H-1,2,4-triazol-5-one (A4)

(A4)

Stage 1:

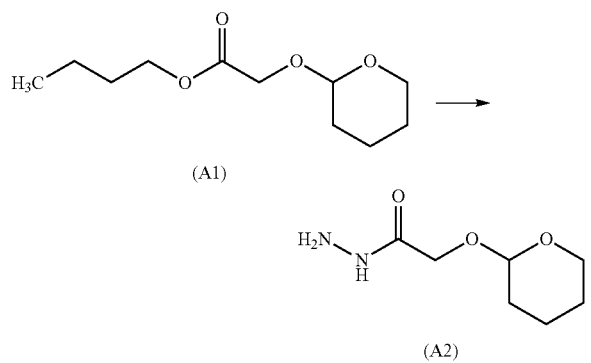

(A1)

(A2)

375 g (1.734 mol) intermediate (A1) was charged to a reactor at 20° C., 104.2 g (2.081 mol) hydrazine hydrate was added and the mixture was heated to 57° C. internal temperature for 3 h (slight reflux). The mixture was subsequently cooled to 22° C.

The crude intermediate (A2) was directly used in the next stage

Intermediate (A2) was previously described in DE 2156472 (Ciba Geigy 1971).

Stage 2:

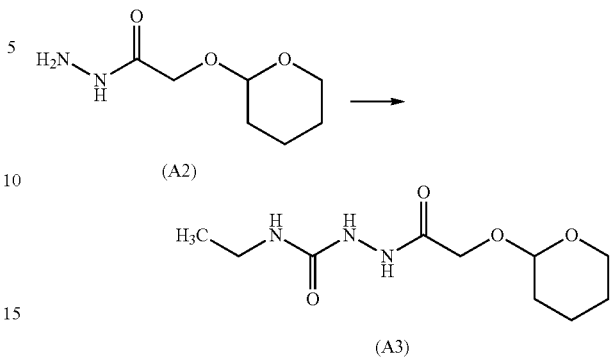

(A2)

(A3)

Water (906 ml) was added to intermediate (A2), and the mixture was cooled to 10° C. Ethyl isocyanate (172.6 g, 2.428 mol) was added at 10-15° C. internal temperature over 50 min. The mixture was subsequently warmed to 20° C. within 30 min.

The crude reaction mixture of intermediate (A3) was directly used in the next stage.

Stage 3:

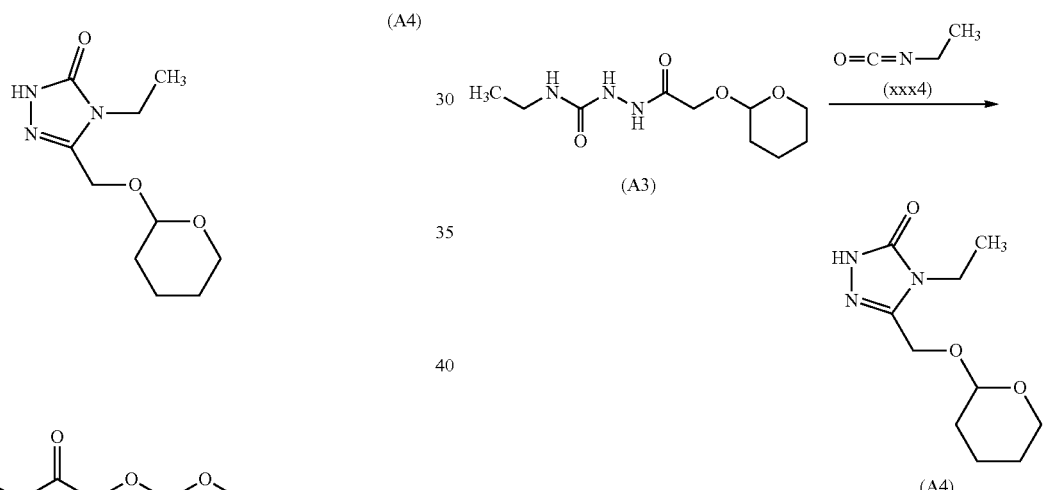

(A3)

(xxx4)

(A4)

50% aqueous sodium hydroxide (34.7 g, 0.434 mol) was added to the crude reaction mixture of intermediate (A3) over 5 min at 20-25° C. The reaction mixture was heated to 79° C. internal temperature for 16 h, then cooled to 20-25° C.

1N hydrochloric acid (ca. 315 mL) was added to adjust to pH 7.3. Dichloromethane (3020 ml) was added, and the suspension was stirred for 15 min. The cloudy organic phase was separated (ca. 2800 ml).

The cloudy aqueous phase was filtered, the filter residue was washed two times with dichloromethane (100 mL each), the filtrate was combined and the resulting second organic phase was separated (1000 ml).

The combined organic phases (ca. 3800 ml) were dried over sodium sulfate, the solids were filtered and the filtrate was evaporated under reduced pressure at 70° C. bath temperature/20 mbar to receive 370.6 g oily distillation residue.

The bath temperature was reduced to 50° C., diisopropyl ether (500 mL) was added to give a clear solution. The mixture was slowly cooled to 20-25° C. and the resulting suspension was stirred over night at 22° C.

The solid product was isolated by filtration, washed three times with cold (0-5° C.) diisopropyl ether (100 mL), (294.8 g wet weight) and dried at 35° C. in vacuo to give 225.7 g (A4) as off-white solid in 57% yield.

$^1$H NMR (400 MHz, DMSO-d$_6$) δ ppm 0.84-0.89 (m, 3H) 1.25-1.43 (m, 4H) 3.32-3.41 (m, 2H) 4.30 (t, J=5.20 Hz, 1H)

HPLC (method 1): R$_t$=1.47 min

LCMS (method 1): R$_t$=0.55 min: MS (ESIpos): m/z=228 (M+H)$^+$

Example 3

4-[4-Ethyl-5-oxo-3-(tetrahydropyran-2-yloxymethyl)-1,2,4-triazol-1-yl]-2,5-difluorobenzonitrile (A5)

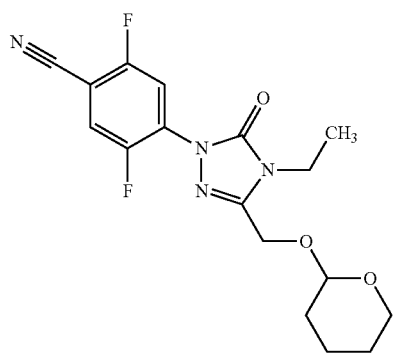

(A5)

Intermediate (A4) (250 g, 1.10 mol) and 2,4,5-trifluorobenzonitrile (xxx5) (190 g, 1.21 mol) were stirred in acetonitrile (2500 mL) and potassium phosphate (467 g, 2.20 mol) was added. The mixture was stirred at 70-73° C. for 20 h, then allowed to cool to room temperature. Water (1200 mL) was added, and the mixture was stirred for 15 min. The organic phase was separated, washed with 10% aqueous sodium chloride (1200 mL) and evaporated under reduced pressure at 40° C. bath temperature to receive 414 g of a brown viscous oil. The residue was dissolved in anhydrous ethanol (915 mL) at 40° C., then cooled to 25° C. to initiate crystallization. Water (1250 mL) was added and the suspension was stirred at 22° C. After stirring for 16 h, the solids were isolated, washed two times with ethanol/water (3:4 v/v, 245 mL) and dried at 40° C. in vacuo to give (A5) (367 g, 1.01 mol, 91% yield) as off-white solid.

$^1$H NMR (400 MHz, DMSO-d$_6$) δ ppm 1.27 (t, J=7.09 Hz, 3H) 1.51 (br d, J=7.46 Hz, 4H) 1.69 (br d, J=9.05 Hz, 2H) 3.48-3.57 (m, 1H) 3.72-3.81 (m, 3H) 4.50 (d, J=12.84 Hz, 1H) 4.66 (d, J=12.96 Hz, 1H) 4.78 (br s, 1H) 7.88 (dd, J=9.29, 5.75 Hz, 1H) 8.22 (dd, J=9.66, 5.38 Hz, 1H)

LCMS (method 3): R$_t$=1.83 min: MS (ESIpos): m/z=365 (M+H)$^+$

Example 4

4-[4-Ethyl-5-oxo-3-(tetrahydropyran-2-yloxymethyl)-1,2,4-triazol-1-yl]-5-fluoro-2-[(1S)-2,2,2-trifluoro-1-methyl-ethoxy]benzonitrile (A6)

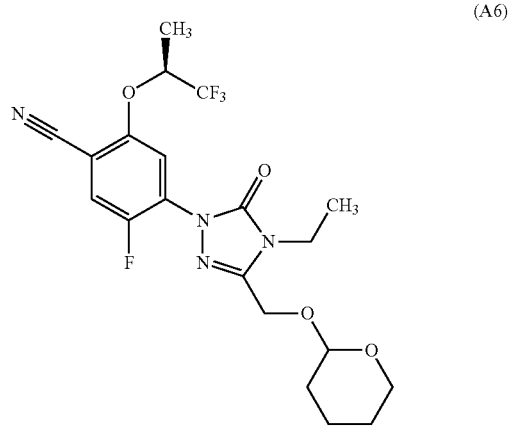 [SMILES: CCn1c(COC2CCCCO2)nn(-c2cc(O[C@@H](C)C(F)(F)F)c(C#N)cc2F)c1=O]

(A6)

Intermediate (A5) (250 g, 686 mmol) was stirred in acetonitrile (1250 mL). (S)-1,1,1-trifluoro-2-propanol (117 mL, 1.03 mol) was added followed by potassium phosphate (291 g, 1.37 mol). The mixture was stirred at 73° C. for 24 h, then cooled to 22° C. Water (750 mL) was added and the mixture was stirred for 15 min.

The organic phase was separated, washed with 10% aqueous sodium chloride (750 mL), and evaporated in vacuum at 50° C. to give the crude product (A6) (320 g, 686 mmol) as viscous yellow oil in quantitative yield.

The crude product was directly used in the next stage.

$^1$H NMR (400 MHz, DMSO-d$_6$) δ ppm 1.28 (t, J=7.15 Hz, 3H) 1.45-1.57 (m, 7H) 1.69 (br d, J=8.56 Hz, 2H) 3.48-3.57 (m, 1H) 3.78 (q, J=6.93 Hz, 3H) 4.51 (d, J=12.84 Hz, 1H) 4.68 (d, J=12.84 Hz, 1H) 4.79 (br s, 1H) 5.48 (spt, J=6.26 Hz, 1H) 7.75 (d, J=5.99 Hz, 1H) 8.08 (d, J=9.90 Hz, 1H)

LCMS (method 1): R$_t$=1.07 min: MS (ESIpos): m/z=459 (M+H)$^+$

Example 5

4-[4-Ethyl-5-oxo-3-(tetrahydropyran-2-yloxymethyl)-1,2,4-triazol-1-yl]-5-fluoro-2-[(1S)-2,2,2-trifluoro-1-methyl-ethoxy]benzoic Acid (A7)

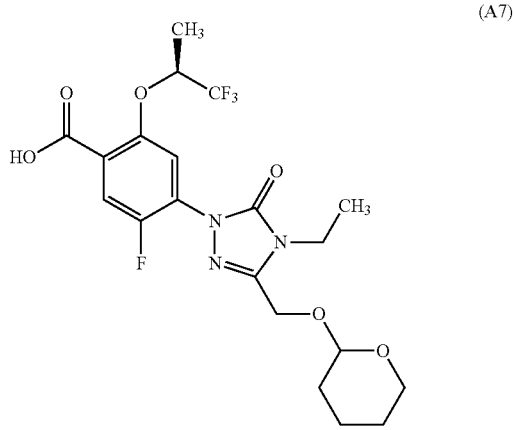 [SMILES: CCn1c(COC2CCCCO2)nn(-c2cc(O[C@@H](C)C(F)(F)F)c(C(=O)O)cc2F)c1=O]

(A7)

The crude product (A6) from the preceding stage (320 g, 686 mmol) was dissolved in ethanol (960 mL). Aqueous sodium hydroxide (2N, 1048 mL) was added and the mixture was stirred at 70° C. for 28 h. After cooling to 22° C., the mixture was acidified (pH 4) by addition of 2N hydrochloric acid (1245 mL). tert-Butyl methyl ether (1600 mL) was added, and the mixture was stirred for 15 min. The organic phase was separated, the aqueous phase was re-extracted with tert-butyl methyl ether (640 mL). The combined organic phases were dried over sodium sulfate, filtered and evaporated in vacuum (stage-wise up to 50° C./20 mbar) to give a solidifying oil (328 g).

The distillation residue was dissolved in diisopropyl ether (656 mL) at 60° C., then slowly cooled to 22° C. and stirred for 16 h. Tetrahydrofuran (49 mL) was added and the suspension was cooled to 0-5° C.

After stirring for 1 h, the solids were isolated, washed two times with cold diisopropyl ether/tetrahydrofuran (20:1 v/v, 120 mL) and dried at 35° C. in vacuo to give (A7) (210 g, 0.44 mol, 63% yield) as off-white solid.

$^1$H NMR (400 MHz, DMSO-d$_6$) δ ppm 1.21-1.33 (m, 3H) 1.37-1.45 (m, 3H) 1.45-1.61 (m, 4H) 1.69 (br d, J=8.93 Hz, 2H) 3.45-3.57 (m, 1H) 3.77 (q, J=7.01 Hz, 3H) 4.39-4.70 (m, 2H) 4.79 (br s, 1H) 5.25 (dt, J=12.84, 6.42 Hz, 1H) 7.55 (d, J=6.11 Hz, 1H) 7.67 (d, J=10.27 Hz, 1H) 13.04-13.60 (m, 1H)

HPLC (method 1): R$_t$=2.82 min

LCMS (method 3): R$_t$=1.76 min; MS (ESIpos): m/z=478 (M+H)$^+$

Example 6

4-[4-Ethyl-5-oxo-3-(tetrahydropyran-2-yloxymethyl)-1,2,4-triazol-1-yl]-5-fluoro-2-[(1S)-2,2,2-trifluoro-1-methyl-ethoxy]benzoyl chloride (A8) and N-(2-chloro-6-fluoro-phenyl)-4-[4-ethyl-5-oxo-3-(tetrahydropyran-2-yloxymethyl)-1,2,4-triazol-1-yl]-5-fluoro-2-[(1S)-2,2,2-trifluoro-1-methyl-ethoxy] benzamide (A9)

-continued

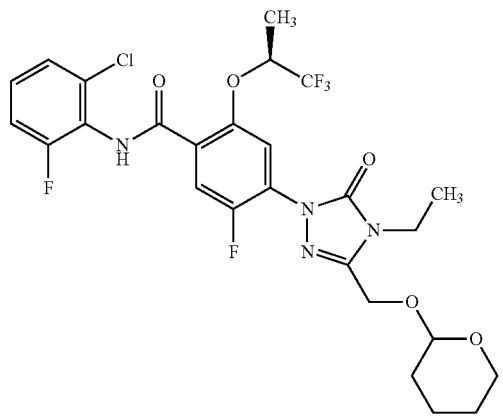

(A9)

Compound (A8) was obtained as an intermediate of the process as described below under Method A and Method B without being isolated nor purified and introduced directly in the following reaction step to obtain compound (A9).

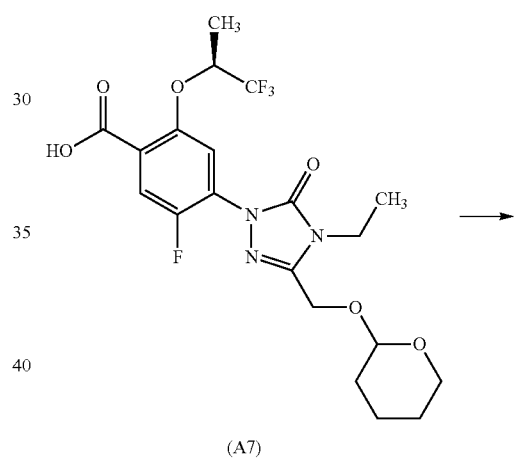

(A7)

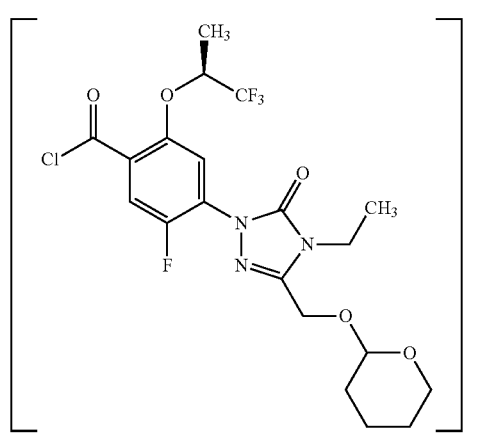

(A8)
and

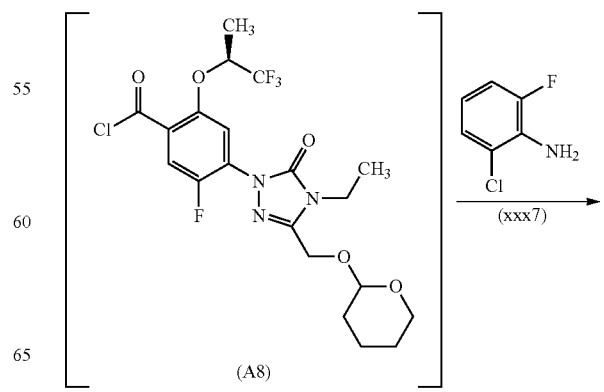

(A8)
(xxx7)

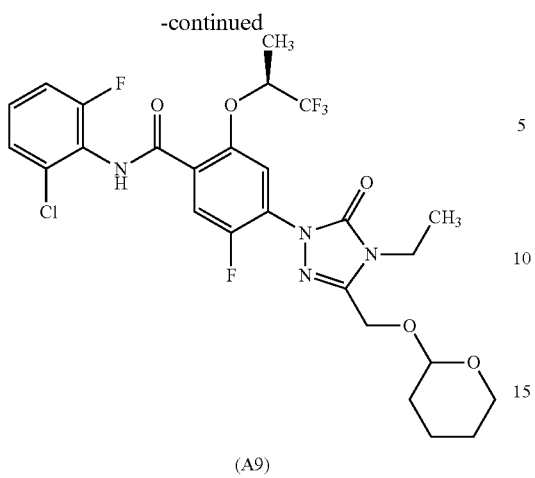

(A9)

Method A:

Intermediate (A7) (71 g, 148 mmol) as obtained from example 5 was dissolved in dichloromethane (355 mL) at 22° C. Ghosez's reagent (1-Chloro-N,N,2-trimethyl-1-propenylamine) was added (25 mL, 186 mmol, CAS-no. 26189-59-3, obtained from Sigma-Aldrich, product code 498270) and the mixture containing not isolated intermediate (A8) was stirred for 30 min.

In a second reaction vessel, 2-chloro-6-fluoroaniline (32.5 g, 223 mmol, CAS-no. 363-51-9 obtained from Combiblocks, catalogue product code OS-7812; alternatively a preparation of 2-chloro-6-fluoroaniline is described in U.S. Pat. No. 4,089,958, example XVIII) was dissolved in dichloromethane (370 mL). Pyridine was added (120 mL, 149 mol) and the mixture was cooled to 0-5° C. The contents of the first vessel was added slowly (ca. 30 min) to the second vessel and the resulting mixture was stirred for 1 h. After heating to 22° C. water (737 mL) was added and the mixture was vigorously stirred over 15 min. The organic phase was separated, consecutively washed with water (737 mL) and 10% aqueous sodium chloride (737 mL), dried over sodium sulfate, filtered and evaporated in vacuum. The residue was placed on silica gel (250 g), the silica bed was eluted with dichloromethane (1500 mL) and the filtrate evaporated in vacuum to give the crude product (A9) (139.7 g [155%], 148 mmol calc. for 100% yield) also oily residue.

The crude product was directly converted in the next step (Example 7, method A).

HPLC (method 1): $R_t$=3.64 min (68% area)

Method B:

To a stirred solution of (A7) (20.0 g, 41.9 mmol) as obtained from example 5 in dichloromethane (180 mL) was added pyridine (10.2 mL, 126 mmol) and 2-chloro-6-fluoroaniline (9.15 g, 62.8 mmol, CAS-no. 363-51-9 obtained from Combiblocks, product code OS-7812; alternatively a preparation of 2-chloro-6-fluoroaniline is described in U.S. Pat. No. 4,089,958, example XVIII) at 22° C. (1-Cyano-2-ethoxy-2-oxoethylidenaminooxy)dimethylamino-morpholino-carbenium hexafluorophosphate (COMU®, 22.4 g, 52.3 mmol, CAS-no. 1075198-30-9, Sigma-Aldrich product code 712191) was added and the mixture was heated to 40° C. for 92 h.

After cooling to 22° C., water (150 mL) was added and the mixture was vigorously stirred over 15 min. The organic phase was separated, consecutively washed two times with water (150 mL) and 10% aqueous sodium chloride (150 mL) and evaporated in vacuum to give the crude product (A9) (41.1 g [162%], 41.9 mmol calc. for 100% yield) also oily residue.

HPLC (method 1): $R_t$=3.63 min (62% area)

The crude product can be directly converted in the next step without further purification (Example 7, method A).

$^1$H NMR (600 MHz, DMSO-$d_6$) δ ppm 1.24-1.37 (m, 3H) 1.39-1.58 (m, 7H) 1.64-1.79 (m, 2H) 3.46-3.58 (m, 1H) 3.72-3.90 (m, 3H) 4.42-4.57 (m, 1H) 4.62-4.73 (m, 1H) 4.77-4.85 (m, 1H) 5.20-5.46 (m, 1H) 7.27-7.48 (m, 3H) 7.54-7.69 (m, 2H) 10.03 (s, 1H)

LCMS (method 1): $R_t$=1.17 min: MS (ESIpos): m/z=605 (M+H)$^+$

Example 7

N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, Compound (I)

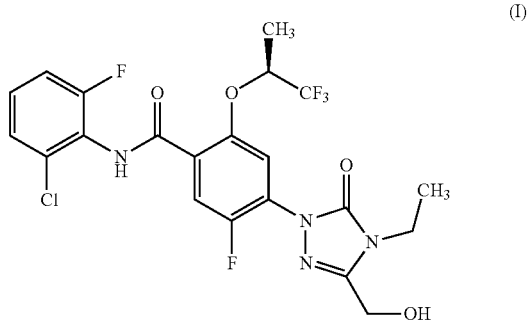 [SMILES: CCn1c(CO)nn(-c2cc(O[C@@H](C)C(F)(F)F)c(C(=O)Nc3c(F)cccc3Cl)cc2F)c1=O]

(I)

Method A

The crude oily residue from example 6 (A9), method A) (139.7 g, 148 mmol calc. for 100% yield) was dissolved in anhydrous ethanol (450 mL), 85% phosphoric acid (50 mL) was added and the mixture was heated at 57° C. bath temperature for 16 h. The resulting biphasic suspension was cooled to 22° C. Hydrochloric acid (1N, 140 mL), diisopropyl ether (700 mL), water (280 mL) and saturated aqueous sodium chloride (140 mL) were added and the mixture was vigorously stirred for 15 min. The mixture was filtered, the filter cake was washed two times with diisopropyl ether (150 mL), and the filtrate was stirred with 10% aqueous sodium chlorid (560 mL) at 22° C. The resulting suspension was filtered and the filter cake was washed two times with diisopropyl ether (150 mL). The isolated solid was suspended in 2-butanone (100 mL), heated to 60° C., the hot suspension was filtered and the filter cake was washed with 2-butanone (30 mL). The filtrate was evaporated in vacuum to give (1) as solid product (24.0 g, 46.1 mmol) in 31% yield.

HPLC (method 1): $R_t$=2.81 min (96% area)

Method B:

a) To a stirred suspension of (A7) as obtained from example 5 (60.0 g, 126 mmol) in acetonitrile (180 mL) was added pyridine (35.6 mL, 440 mmol) and 2-chloro-6-fluoroaniline (27.4 g, 188 mmol, CAS-no. 363-51-9 obtained from Combiblocks, product code OS-7812; alternatively a preparation of 2-chloro-6-fluoroaniline is described in U.S. Pat. No. 4,089,958, example XVIII) at 22° C. The cloudy solution was cooled to 0-5° C. and phosphoryl chloride (21.2 g, 138 mmol) was added over a period of 10 min. The reaction mixture was stirred for 1 h resulting in a clear solution. Methanol (360 mL) and 85% phosphoric acid (12.8 mL, 189 mmol) were added and the mixture was heated to 60° C. for 2 h.

The reaction solvent was partially removed by distillation (95° C. bath, 64-72° C. internal temperature) to give 420 mL distillate. The distillation residue was slowly cooled to 22° C. and stirred for 16 h. The resulting suspension was cooled to 0-5° C. and stirred for additional 2 h. The solid was isolated, washed two times with 2-propanol (30 mL) and dried in vacuum at 50° C. for 16 h to give crude product Compound (I) as a white solid (55 g, 106 mmol) in 84% yield.

HPLC (method 1): $R_t$=2.81 min (>98% area)

b) The reaction product (30.0 g, 57.6 mmol) was further purified by suspension in anhydrous ethanol (450 mL) and heating to 60° C. The resulting clear solution was filtered, the filter cake was washed two times with hot anhydrous ethanol (30 mL) and the filtrate was concentrated by distillation of solvent (270 mL distillate) at 100° C. bath temperature. The solution was cooled to 50° C., seeded (1) (0.3 g), and cooled stepwise to 0-5° C. over 4 h. The precipitated solid was isolated, washed two times with anhydrous ethanol (15 mL) and dried in vacuum at 50° C. for 16 h to give Compound (I) as a white solid (25.7 g, 49.3 mmol) in 86% yield from crude Compound (I).

HPLC (method 1): $R_t$=2.81 min (>99% area)

$^1$H NMR (400 MHz, DMSO-$d_6$) δ ppm 1.29 (t, J=7.15 Hz, 3H) 1.45 (d, J=6.36 Hz, 3H) 3.80 (q, J=7.09 Hz, 2H) 4.44-4.55 (m, 2H) 5.36 (dt, J=12.78, 6.33 Hz, 1H) 5.80 (t, J=5.75 Hz, 1H) 7.30-7.47 (m, 3H) 7.50-7.66 (m, 2H) 10.05 (s, 1H)

LCMS (method 1): $R_t$=0.90 min; MS (ESIpos): m/z=521 (M+H)$^+$

Optionally the product obtained before recrystallization (see example 7B, a)) was micronized in an air jet mill (see example 9-1)

Example 8

In analogy to example 7, Method B a) and b), two experiments were conducted each starting from

| amount | compound |
|---|---|
| 335 g | (A7) |
| 784 g | acetonitrile |
| 193 g | pyridine |
| 153 g | 2-chloro-6-fluoroaniline |
| 118 g | phosphorylchloride |
| 1588 g | methanol |
| 121 g | phosphoric acid, 85% |
| 265 g | 2-propanol |
| 3316 g | ethanol (for crystallization) |
| 438 g | ethanol (for initial washings) |
| 2 g | Compound (I), crystalline form A for seeding |
| 112 g | ethanol (for final washings) |

The product Compound (I) batches obtained from these two experiments were combined (527 g) and were micronized using the method disclosed in Example 9-2 to give 485 g micronized material.

Example 9—Micronization

Example 9-1

24.4 g of crude compound (I) obtained from example 7, Method B, a) were combined with other charges of compound (I) obtained by example 7, method A or B and recrystallized using the method as described under example 7, method B, b).

The product obtained after recrystallization was micronized in an air jet mill.

a) Used Device:

| Used Device | Mill | 50 mm spiral jet mill (Bayer design) |
|---|---|---|
| | Dosing device (Type) | vibrating chute |
| | Grinding chamber lining (material) | stainless steel (SST) |
| | Injector motive nozzle (diameter) | 0.9 mm SST |
| | Grinding nozzle (diameter) | 0.6 mm SST |
| | Collecting nozzle (diameter) | 2.5 mm SST |
| | Outlet opening (diameter) | 12 mm SST | b) Grinding Parameters

| Grinding Parameter | | Actual value |
|---|---|---|
| Injector air pressure | [bar] | 4.5 |
| Grinding air pressure | [bar] | 4 |
| Product throughput | [g/min] | 5.4 |
| Differential pressure filter, end | [mbar] | 50 |
| Total grinding time | [min] | 21 | c) The Micronized Product Obtained has the Following Properties:

Particle Size distribution (X10/X50/X90): 0.6/1.4/3.8 μm.

The Instrumental Set-Up for Particle Size Analysis:

Laser diffraction pattern analyzer (Sympatec HELOS, H1970 & RODOS, R3:0.5/0.9 . . . 175 μm), 100 mm focal length, Dry dispersion (RODOS) at 4 bar, Mathematical model (LD 5.9.0.0)—Sympatec Code, basis Fraunhofer Diffraction Thus one embodiment of the invention are micronized particles of Compound (I) within a size range of 0.6 μm-3.8 μm (X10-X90).

Thus one embodiment of the invention are micronized particles of Compound (I) within a size range of (X10/X50/X90): 0.6/1.4/3.8 μm The product as obtained is characterized by a specific fingerprint of impurities. Such fingerprint comprises

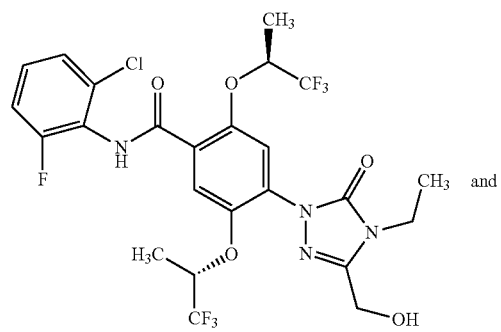

and

-continued

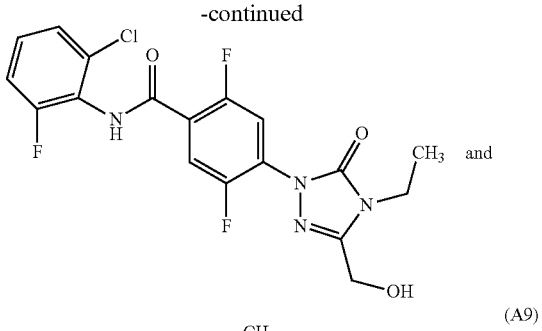

(A9)

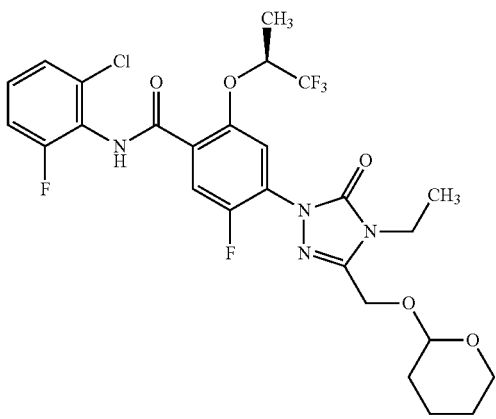

Example 9-2

The product obtained from example 8 after recrystallization (527 g combined) was micronized in a spiral jet mill to give 485 g micronized material (92% yield):
a) Device

| Used Device | Mill | 50 mm spiral jet mill (Bayer design) |
|---|---|---|
| | Grinding chamber lining (material) | PTFE |
| | Injector motive nozzle (diameter) | 0.9 mm |
| | Grinding nozzle (diameter) | 0.75 mm, |
| | Collecting nozzle (diameter) | 2.5 mm PTFE |
| | Outlet opening (diameter) | 12 mm PTFE | b) Grinding Parameters

| Grinding Parameter | | Actual value |
|---|---|---|
| Grinding air pressure | [bar] | 5 |
| Product throughput | [kg/h] | 0.9 |
| Total grinding time | [min] | 35 | c) The Micronized Product Obtained has the Following Properties:

Three samples have been taken and analyzed. The following parameters are mean values from the three measurements:

Particle Size distribution (X10/X50/X90): 0.6/1/3 µm

Thus one embodiment of the invention are micronized particles of Compound (I) within a range of 0.6/1/3 µm (X10/X50/X90).

The Instrumental Set-Up for Particle Size Analysis:

Laser diffraction pattern analyzer (Sympatec HELOS, H1970 & RODOS, R3:0.5/0.9 . . . 175 µm), 100 mm focal length, Dry dispersion (RODOS) at 4 bar, Mathematical model (LD 5.9.0.0)—Sympatec Code, basis Fraunhofer Diffraction Thus one embodiment of the invention are micronized particles of Compound (I) within a range of 0.6 µm-3 µm.

Example 10

Figure 1A:
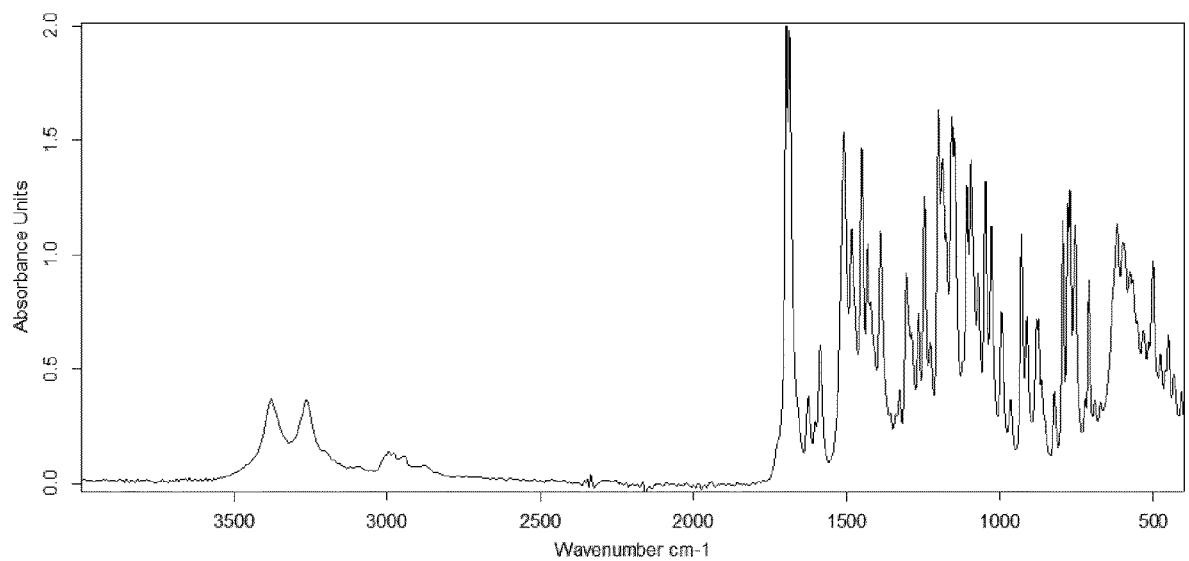

Infrared spectroscopy of crystalline micronized Compound (I) obtained from example 9-1 see FIG. 1A or for 9-2, see FIG. 1 respectively.

TABLE 1

Values of the band maxima of the IR spectrum of Compound (I) as shown in FIG. 1 are listed in table 1. The most intense bands are observed at 1699, 1511, 1453, 1246 and 1202 cm$^{-1}$.
The 3, 5, 7, and 10 most intense and/or characteristic bands are observed at: 1699, 1688, 1511;
1699, 1688, 1511, 1202;
3382, 3265, 1699, 1688, 1511, 1453, 1202,
3382, 3265, 1699, 1688, 1511, 1453, 1246, 1202, 1095 and 1049 cm-1, respectively.

| Band maxima (cm$^{-1}$) | Band maxima (cm$^{-1}$) |
|---|---|
| 3382 | 1148 |
| 3265 | 1108 |
| 1699 | 1096 |
| 1688 | 1071 |
| 1626 | 1049 |
| 1604 | 1029 |
| 1588 | 996 |
| 1511 | 931 |
| 1486 | 912 |
| 1453 | 883 |
| 1433 | 875 |
| 1421 | 796 |
| 1389 | 781 |
| 1326 | 773 |
| 1306 | 755 |
| 1287 | 711 |
| 1266 | 619 |
| 1246 | 599 |
| 1226 | 502 |
| 1202 | |
| 1189 | |
| 1174 | |
| 1158 | |

The Instrumental set-up for the IR measurement of Compound (I) in order to obtain the bands listed in table 1 and the IR spectrum as a graph as disclosed in FIG. 1 is the following:

Sample preparation: The sample of the product obtained by example 9-2 is prepared as a KBr disc by taking a spatula tip of the substance which is mixed and homogenized with a ca. 200-400 fold amount of dry potassium bromide powder in an agate mortar. The mixture is prepared by means of a press to produce a disk with uniform transparency.

Apparatus: FT-IR Spectrometer (Bruker Vertex 80v)
Scans: 32
Resolution: 2 cm$^{-1}$
Technique: transmission The Instrumental set-up for the IR measurement of Compound (I) in order to obtain the bands listed in table 1 and the IR spectrum as a graph as disclosed in FIG. 1A is the following: Instrumental set-up for the IR measurement of a sample of the product of example 9-1,
Sample preparation: None
Apparatus: FT-IR Spectrometer (Bruker alpha with ATR attachment)
Scans: 24
Resolution: 4 cm-1
Technique: attenuated total reflectance

Example 11

X-Ray Powder Diffraction of Crystalline Micronized Compound (I) Obtained in Example 9-2 (FIG. 2)

TABLE 2

Values of the diffraction peaks of the diffractogram of Compound (I) as shown in FIG. 2, wherein the more intense diffraction peaks are observed at 17.2, 18.3, 19.1, 21.0, 22.5 and 25.2.

| Diffraction angle (2θ, °) | Diffraction angle (2θ, °) | Diffraction angle (2θ, °) |
|---|---|---|
| 7.7  | 25.2 | 35.4 |
| 8.6  | 25.7 | 36.2 |
| 10.7 | 25.9 | 36.7 |
| 12.7 | 26.2 | 36.9 |
| 13.4 | 26.5 | 37.2 |
| 14.2 | 27.0 | 37.9 |
| 14.4 | 27.6 | 39.2 |
| 15.4 | 28.1 |      |
| 15.6 | 28.5 |      |
| 17.2 | 29.1 |      |
| 17.6 | 29.4 |      |
| 18.2 | 29.9 |      |
| 18.3 | 30.3 |      |
| 19.1 | 31.2 |      |
| 19.7 | 31.5 |      |
| 20.6 | 32.2 |      |
| 21.0 | 32.5 |      |
| 21.5 | 33.1 |      |
| 21.6 | 33.4 |      |
| 22.5 | 33.7 |      |
| 22.7 | 34.3 |      |
| 24.0 | 34.6 |      |
| 24.3 | 34.8 |      |

The instrumental set-up for obtaining the diffractogram is:

Sample preparation: The powder is prepared as a thin layer between two films of Compound (I) obtained in example 9-2.

Apparatus: X-ray powder diffractometer (STOE STADI P)

Generator: 40 kV/40 mA

Detector: linear position sensitive detector

Radiation: germanium-monochromatized $CuK_{\alpha 1}$-radiation

Technique: transmission

Scanning range: $2° \leq 2\theta \leq 40°$

Stepwidth: 0.5°

Measuring time: 15 sec/step

Example 12

Thermograms of Crystalline Micronized Compound (I)

Figure 3:
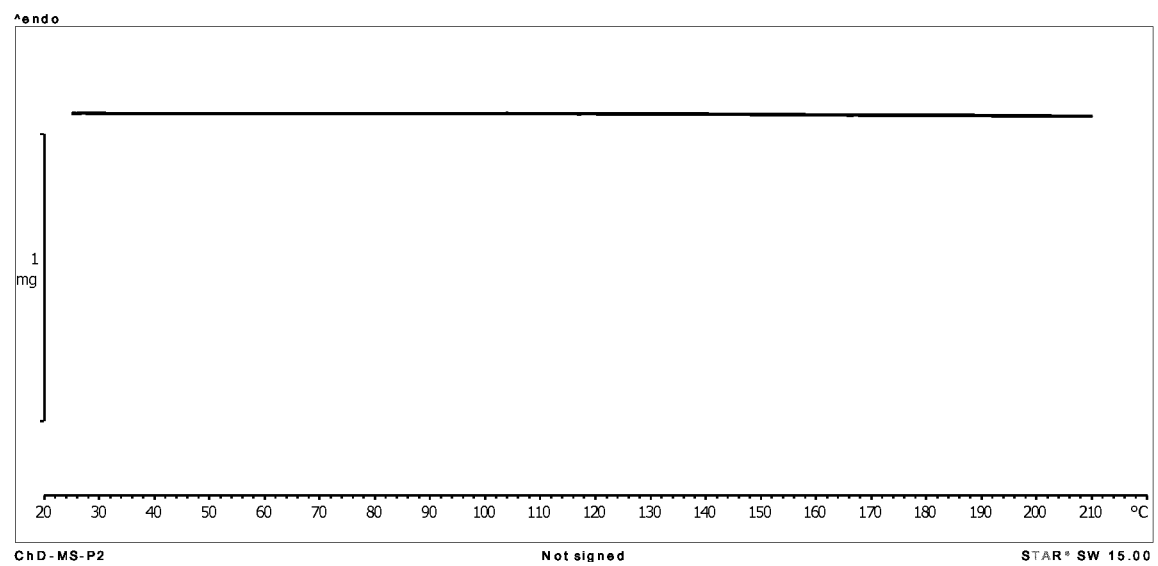

The thermogravimetric Analysis (TGA) Curve of Compound (I) obtained in example 9-2 is disclosed in FIG. 3.

The Instrumental set-up for obtaining a TGA curve is the following:

Sample preparation: The powder is crimped in a 100 µl aluminum pan and lid. The lid is pierced directly prior to the start of the experiment.

Apparatus: Thermogravimetric Analyser (Mettler Toledo TGA/DSC1)

Temperature range: 25-210° C.

Heating rate: 10 K·min$^{-1}$

Gas: Nitrogen

Gas flow: 50 ml·min$^{-1}$

Example 13

Differentiation Scanning Calorimetry (DSC) Curve of Compound (I) obtained in example 9-2 is shown in FIG. 4.

Instrumental Set-Up to Obtain a DSC Curve:

Sample preparation: The powder is crimped in a 400 µl aluminum pan and with a pierced lid.

Apparatus: Differential Scanning Calorimeter (Mettler Toledo DSC822e)

Temperature range: −10-210° C.

Heating rate: 20 K·min$^{-1}$

Gas: Nitrogen

Gas flow: 50 ml·min$^{-1}$

Example 14

Preparation of Amorphous Form

Compound (I) (200 mg, 0.38 mmol) was dissolved in pyridine (1.5 mL). The solution was filtered (0.2 µm ReZist® Filter, Whatman) and transferred to a second Vial. The solvent was evaporated at 115° C. using a heat gun or can alternatively be obtained by evaporation in vacuum at 85° C./5 mbar to give the amorphous form of Compound (I) as solidified oil or foam. Analytics of amorphous form of Compound (I): Examples 15-17

Example 15

Infrared Spectroscopy of Amorphous Compound (I)

TABLE 3

Figure 5:
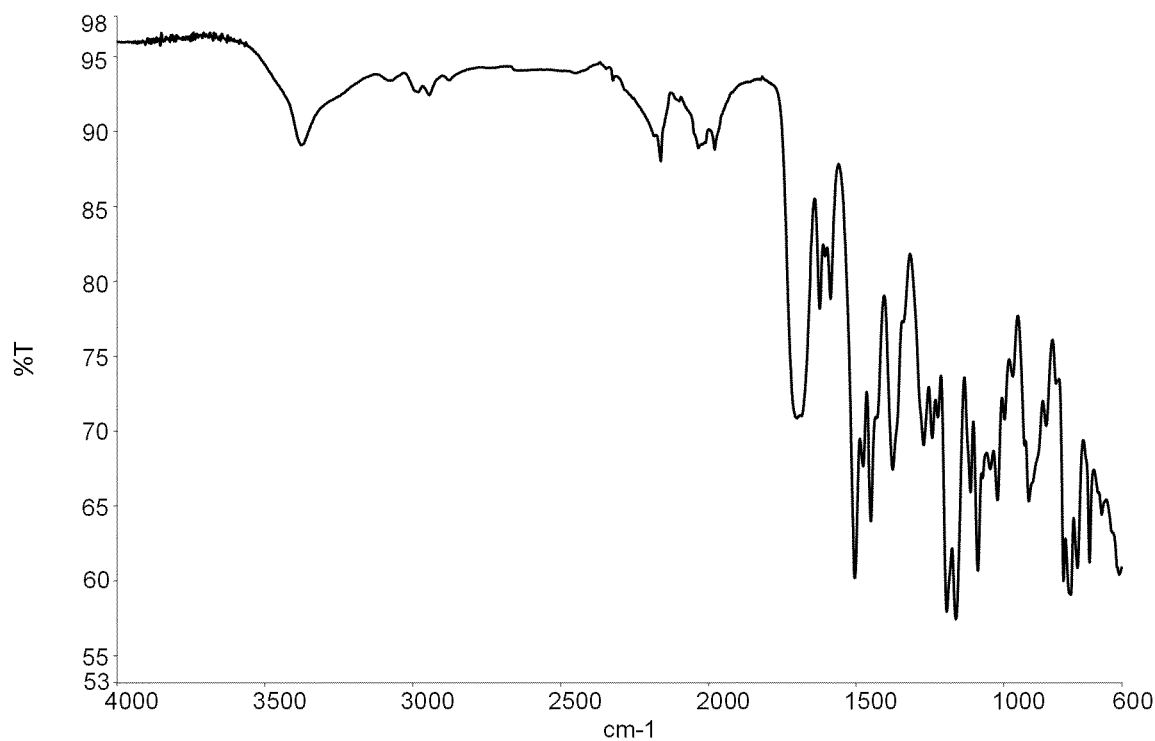

2θ Values of the band maxima of the IR spectrum of Compound (I) as shown in FIG. 5 are listed in table 3.

| X (cm − 1) | Y (%T) |
|---|---|
| 3378 | 89.1 |
| 2945 | 92.5 |
| 2162 | 88.0 |
| 2034. | 88.9 |
| 1979. | 88.8 |
| 1698 | 70.8 |
| 1622 | 78.2 |
| 1585 | 78.8 |
| 1503 | 60.2 |
| 1475 | 67.6 |
| 1448 | 64.0 |
| 1375 | 67.4 |
| 1270 | 69.1 |
| 1241 | 69.5 |
| 1222 | 70.9 |
| 1192 | 57.9 |
| 1161 | 57.4 |
| 1111 | 65.9 |
| 1087 | 60.7 |
| 1045 | 67.5 |
| 1020 | 65.4 |
| 996  | 70.8 |
| 969  | 73.7 |
| 914  | 65.3 |
| 856  | 70.4 |
| 797  | 60.0 |
| 772  | 59.1 |
| 750  | 60.8 |
| 709  | 61.2 |
| 667  | 64.4 |
| 608  | 60.4 |
| 577  | 59.5 |
| 554  | 56.5 |
| 538  | 56.8 |
| 530  | 54.2 |

The Instrumental set-up for the IR measurement of amorphous Compound (I) in order to obtain the bands listed in table 3 and the IR spectrum as a graph as disclosed in FIG. 5 is the following:

Sample preparation: A small amount of Compound (I) was manually milled by using a mortar and pestle.
Apparatus: Thermo Scientific Nicolet iS10
Scans: 64
Resolution: 2 cm-1
Technique: FTIR Example 16

Figure 6:
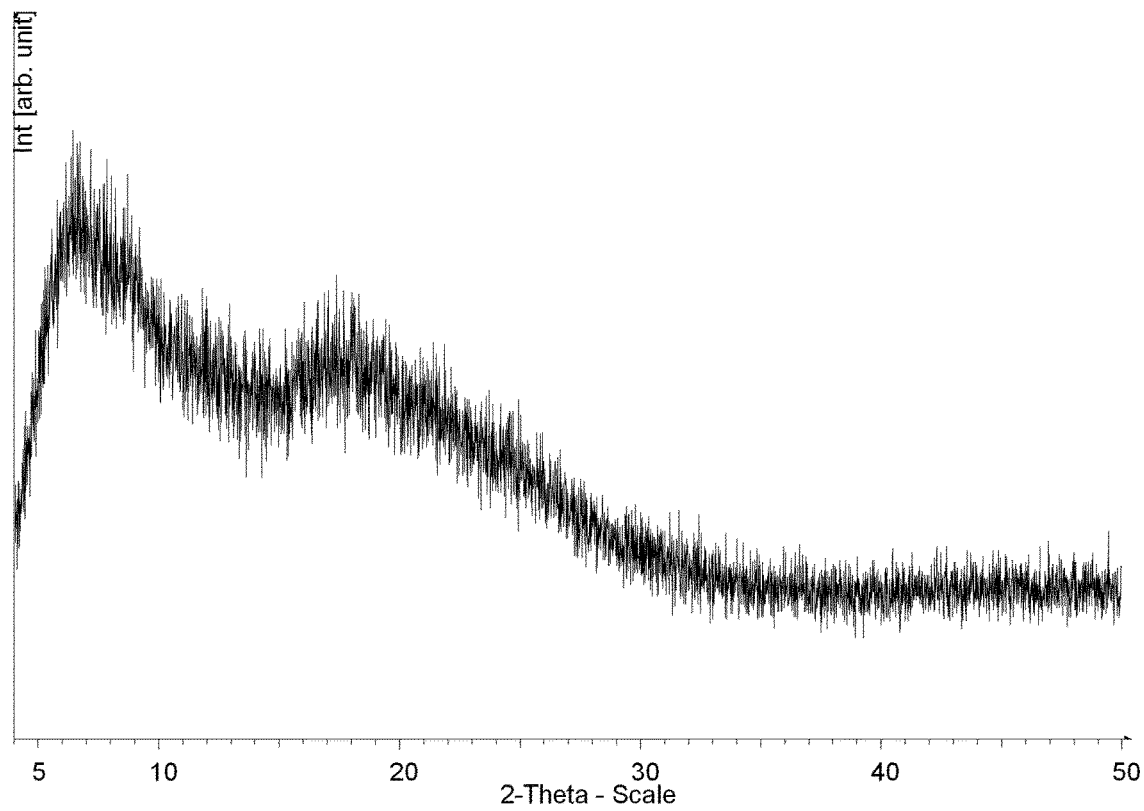

X-Ray Powder Diffraction of Amorphous Compound (I)
FIG. 6 shows the X-ray powder diffractogram of the amorphous phase.

The instrumental set-up for obtaining the diffractogram is:
Sample preparation: A small amount of Compound (I) obtained in example 9-2 was manually milled by using a mortar and pestle, a standard glass capillary is used (diameter=0.7 mm)
Apparatus: D8 Bruker Advance Diffractometer
Generator: 40 kV and 40 mA
Detector: LynxEye
Radiation: Cu—Kα1=1.54059 Å
Technique: transmission
Scanning range: 4-50°
Stepwidth: 0.009°
Measuring time: 2 hours Example 17

Figure 7:
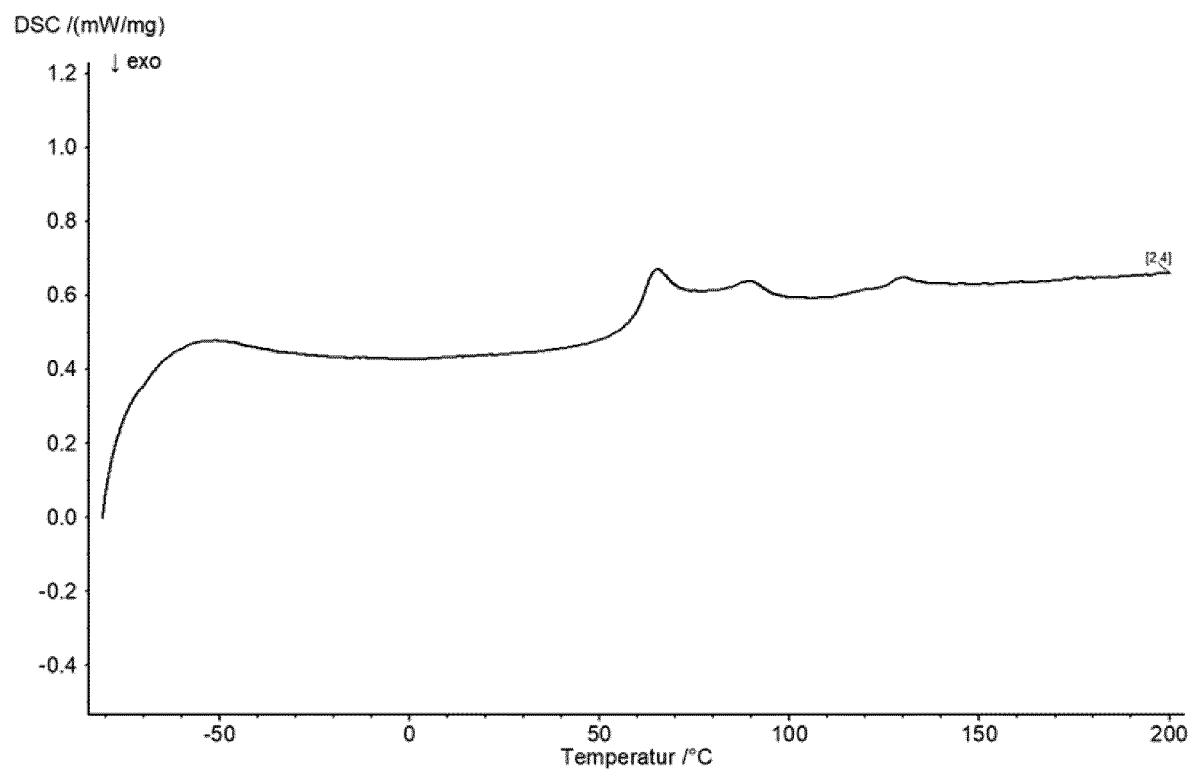

Differentiation Scanning Calorimetry (DSC) curve of amorphous Compound (I) obtained from example 14 is shown in FIG. 7.
Instrumental Set-Up to Obtain a DSC Curve:
Sample preparation: The sample of Compound (I) obtained in example 14 Sealed aluminum pan with one pinhole
Apparatus: Netzsch Phoenix DSC 204 F1
Temperature range: −20° C.→200° C.
Heating rate: 10° C./min
Gas: $N_2$
Gas flow: 20 mL/min

The invention claimed is:

1. A method of preparing Compound (I) comprising the step of allowing an intermediate compound of formula (A7.1):

(A7.1)

wherein PG is a protecting group selected from a tetrahydropyranyl group (THP), a tetrahydrofuranyl group (THF), a 1-ethoxyethyl group (EE), a tert-butyl group (t-Bu), a tert-butoxymethyl group and a methoxyethoxymethyl group (MEM), to react with a compound of formula (xxx7):

(xxx7)

optionally in a suitable aprotic solvent, by addition of a suitable base, optionally under activation of the carboxylic acid group or by generation of an intermediate acid chloride using a suitable reagent, and either adding one or more reagents for cleaving the protecting group or isolating compound (A9.1)

(A9.1)

and subsequently adding a reagent for cleaving the protecting group, thereby providing Compound (I)

Compound (I)

2. The method of preparing Compound (I) according to claim 1 comprising the step of allowing an intermediate compound of formula (A7):

(A7)

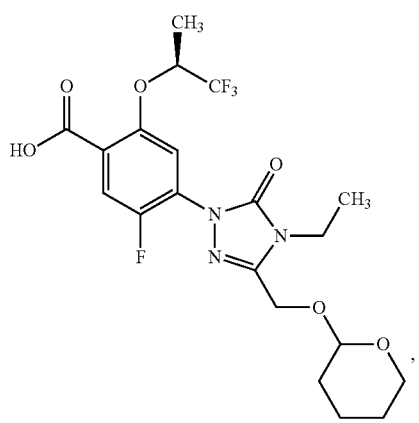

to react with a compound of formula (xxx7):

(xxx7)

optionally in a suitable aprotic solvent by addition of a suitable base, optionally under activation of the carboxylic acid group or by generation of an intermediate acid chloride using a suitable reagent, and either adding one or more reagents for cleaving the protecting group or isolating compound (A9)

(A9)

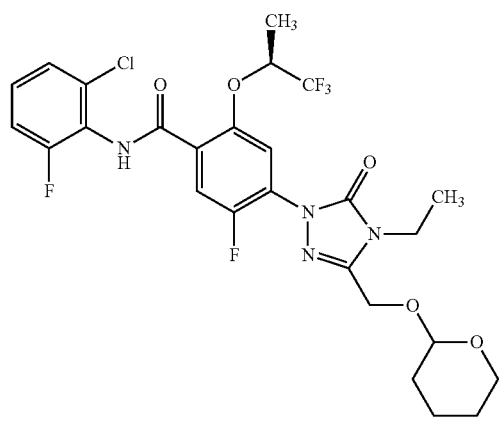

and subsequently adding one or more reagents for cleaving the protecting group, thereby providing Compound (I):

Compound (I)

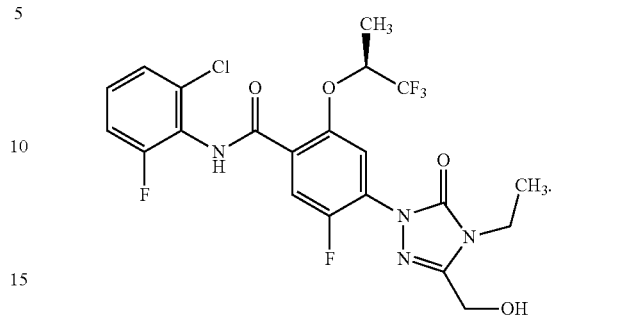

3. The method of claim 1, wherein said suitable base in the reaction of compound A7.1 with the compound of formula (xxx7) is pyridine and/or
   PG is a tetrahydropyranyl and said reagent for cleaving the protecting group causes acidic conditions.

4. The method according to claim 3, wherein said acidic conditions are accomplished by addition of phosphoric acid and methanol.

5. The method of claim 2, wherein said suitable base in the reaction of compound A7.1 with the compound of formula (xxx7) is pyridine and/or said one or more reagents for cleaving the protecting group cause acidic conditions.

6. The method according to claim 1 comprising generation of said intermediate acid chloride.

7. The method according to claim 6 wherein the reagent for generating the intermediate acid chloride is phosphoryl chloride.

8. The method according to claim 1, wherein the intermediate compound of formula (A7.1) is allowed to react with a compound of formula (xxx7) under activation of the carboxylic acid group or by generation of an intermediate acid chloride, wherein the intermediate acid chloride or the activated acid produced from the activation of the carboxylic acid group is generated in situ.

9. The method of claim 2 comprising isolating compound (A9) and subsequently cleaving the protecting group.

10. The method of claim 2 comprising a one-pot process from compound (A7)

(A7)

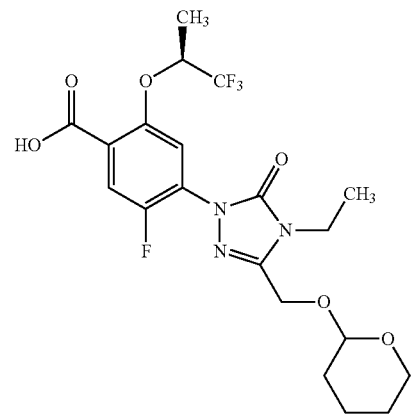

Compound (I)

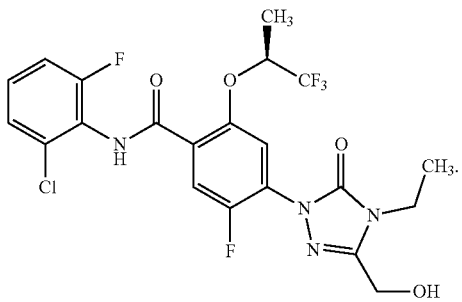

11. The method according to claim 1 further comprising
a step for isolation of Compound (I) and/or
a step for purification of Compound (I) and/or
a micronization step.

12. The method according to claim 2, further comprising reacting a compound of formula (A4)

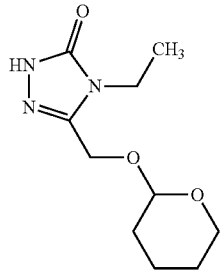
(A4)

optionally in a polar aprotic solvent with 2,4,5-trifluorobenzonitrile (xxx5)

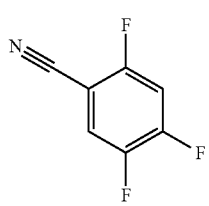
(xxx5)

thereby giving a compound of formula (A5)

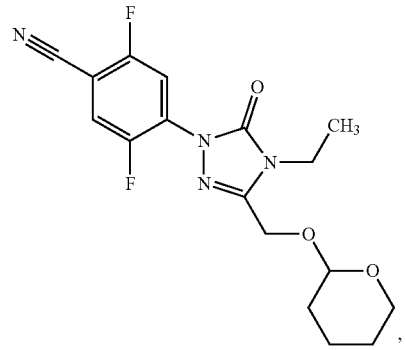
(A5)

and/or
a step of reacting compound (A5) with a compound (xxx6)

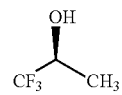
(xxx6)

optionally in a polar aprotic solvent comprising an alkaline metal phosphate, thereby giving a compound of formula (A6)

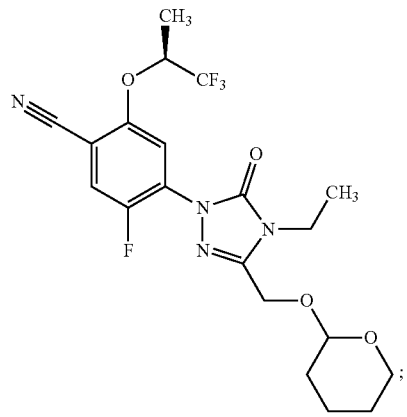
(A6)

and/or
a step of converting a compound of formula (A6) to a compound of formula (A7)

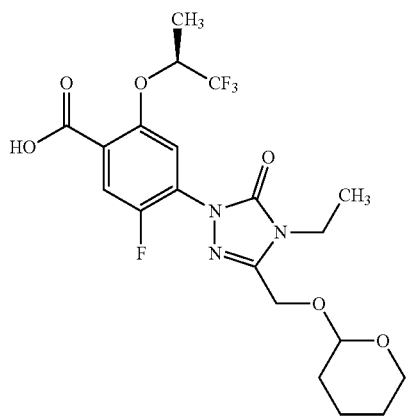
(A7)

wherein each reaction step is optionally in a polar protic solvent comprising an aqueous alkaline metal hydroxide or alkaline earth metal hydroxide solution and optionally further comprising isolating compound (A7).

13. The method according to claim 2, further comprising a step of reacting a compound (A5)

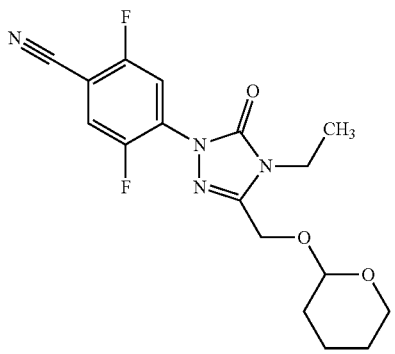
(A5)

with a compound (xxx6)

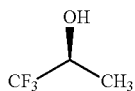
(xxx6)

optionally in a polar aprotic solvent comprising an alkaline metal phosphate, thereby giving a compound of formula (A6)

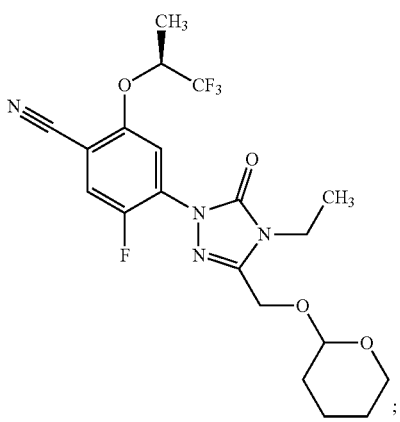
(A6)
;

and a step of converting a compound of formula (A6) to a compound of formula (A7)

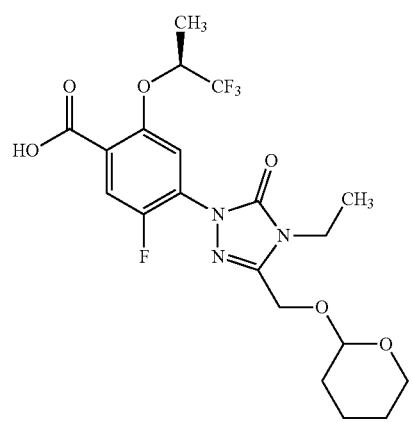
(A7)

wherein each reaction step is optionally in a polar protic solvent comprising an aqueous alkaline metal hydroxide or alkaline earth metal hydroxide solution.

14. The method according to claim 2, further comprising a step of reacting a compound of formula (A4)

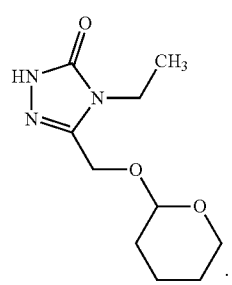
(A4)

optionally in a polar aprotic solvent with 2,4,5-trifluorobenzonitrile (xxx5)

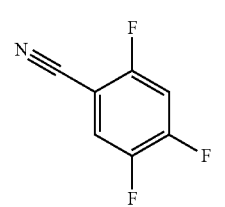
(xxx5)

thereby giving a compound of formula (A5)

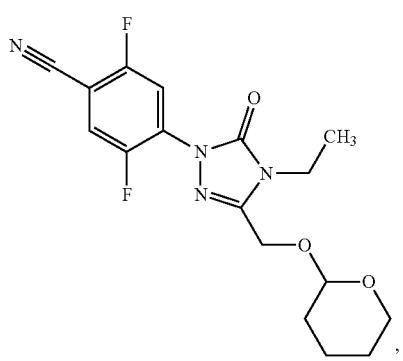
(A5)

and/or
a step of reacting compound (A5) with a compound (xxx6)

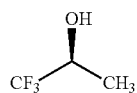
(xxx6)

optionally in a polar aprotic solvent and by addition of an alkaline metal phosphate, thereby giving a compound of formula (A6)

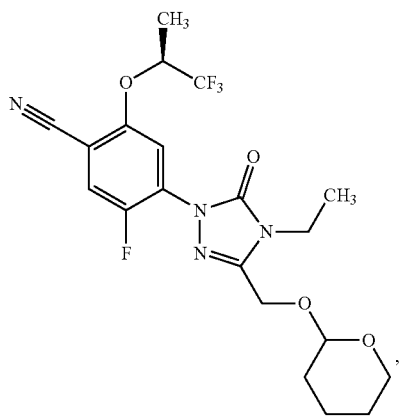
(A6)

and
a step of converting a compound of formula (A6) to a compound of formula (A7)

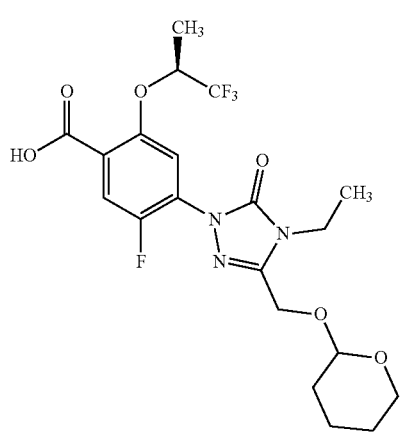
(A7)

wherein each reaction step is optionally in a polar protic solvent comprising an aqueous alkaline metal hydroxide or alkaline earth metal hydroxide solution.

15. An intermediate compound selected from the group consisting of:

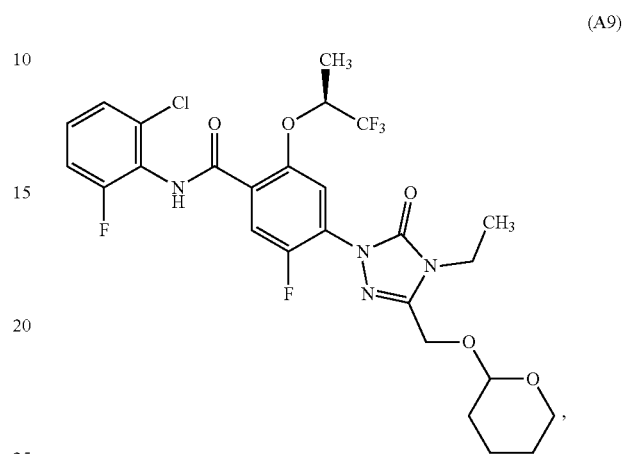
(A9), (A7), (A6)

(A5)

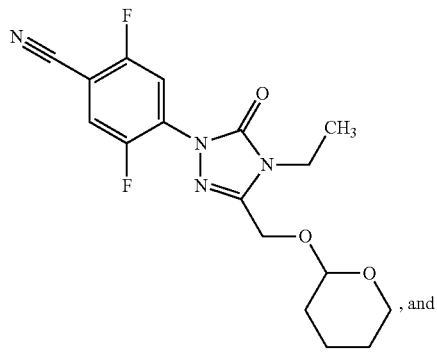

, and (A4)

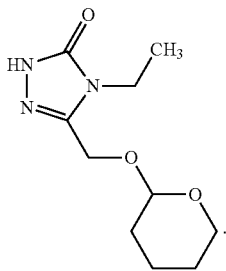

16. A crystalline form A of Compound (I)

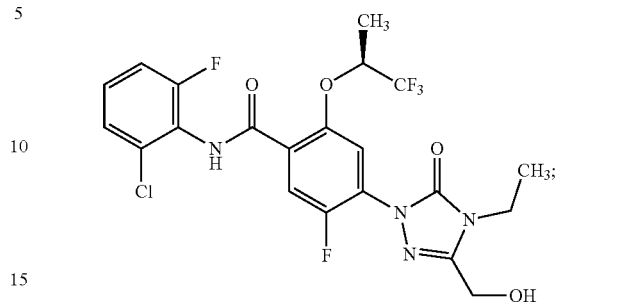

Compound (I)

wherein Crystalline form A of Compound (I) is characterized by a X-ray powder diffractogram measured at 25° C. and with Cu—K alpha 1 as radiation source displaying at least the following reflections, quoted as 2Θ value ±0.2°: 17.2, 18.3, 19.1, 21.0, 25.2.

17. A pharmaceutical composition comprising crystalline form A of Compound (I) according to claim 16 and optionally comprising a pharmaceutically acceptable excipient.

18. A method for the preparation of a pharmaceutical composition comprising mixing the crystalline form A of Compound (I) of claim 16 with a pharmaceutically acceptable excipient.

19. A method for the treatment of a hyperproliferative disease in a subject comprising administration of the pharmaceutical composition according to claim 17 to the subject.

20. The method according to claim 19, wherein the hyperproliferative disease is selected from cancers of breast; brain; digestive tract; eye; head and neck; haematological malignancies including leukemias, lymphomas, multiple myeolomas; liver; parathyroid and their distant metastases; respiratory tract; reproductive organs; urinary tract; sarcomas; skin; and thyroid.

* * * * *